US010239955B2

(12) United States Patent
Naito et al.

(10) Patent No.: US 10,239,955 B2
(45) Date of Patent: *Mar. 26, 2019

(54) MONOCLONAL ANTIBODY, INHIBITING THE ENZYMATIC ACTIVITY OF VASCULAR ENDOTHELIAL LIPASE

(71) Applicant: SHIONOGI & CO., LTD., Osaka-shi, Osaka (JP)

(72) Inventors: Shoichi Naito, Sapporo (JP); Junji Onoda, Toyonaka (JP); Tasuku Tsukamoto, Toyonaka (JP); Katsutoshi Yamada, Toyonaka (JP); Shoji Yamane, Toyonaka (JP); Yoshito Numata, Sapporo (JP); Kazuhiko Maekawa, Toyonaka (JP); Tatsuya Takahashi, Toyonaka (JP)

(73) Assignee: SHIONOGI & CO., LTD., Osaka-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/611,864

(22) Filed: Jun. 2, 2017

(65) Prior Publication Data
US 2017/0275378 A1    Sep. 28, 2017

Related U.S. Application Data

(62) Division of application No. 14/772,340, filed as application No. PCT/JP2014/056526 on Mar. 12, 2014, now Pat. No. 9,701,757.

(30) Foreign Application Priority Data

Mar. 14, 2013  (JP) ................................. 2013-051995

(51) Int. Cl.
| | |
|---|---|
| *C07K 16/40* | (2006.01) |
| *A61K 39/395* | (2006.01) |
| *A61P 3/06* | (2006.01) |
| *C07K 14/47* | (2006.01) |

(52) U.S. Cl.
CPC .......... *C07K 16/40* (2013.01); *A61K 39/3955* (2013.01); *A61P 3/06* (2018.01); *C07K 14/47* (2013.01); *C07K 2317/33* (2013.01); *C07K 2317/34* (2013.01); *C07K 2317/76* (2013.01); *C07K 2317/92* (2013.01); *C12Y 301/01004* (2013.01)

(58) Field of Classification Search
None
See application file for complete search history.

(56) References Cited

U.S. PATENT DOCUMENTS

2015/0025225 A1    1/2015 Naito et al.

FOREIGN PATENT DOCUMENTS

| WO | WO 99/32611 A1 | 7/1999 |
|---|---|---|
| WO | WO 00/57837 A2 | 10/2000 |
| WO | WO 2013/054830 A1 | 4/2013 |

OTHER PUBLICATIONS

Ferrara et al (2015. mAbs. 7(1): 32-41).*
Sandhu et al. 1992. Critical Reviews in Biotechnology. 12(5/6): 437-462.*
Basu et al., "Measurement of the phospholipase activity of endothelial lipase in mouse plasma", Journal of Lipid Research, 2013, vol. 54, pp. 282-289.
Broedl et al., "Endothelial Lipase: A Modulator of Lipoprotein Metabolism Upregulated by Inflammation", TCM, 2004, vol. 14. No. 5, pp. 202-206.
Casset et al., "A peptide mimetic of an anti-CD4 monoclonal antibody by rational design", Biochemical and Biophysical Research Communications, 2003, vol. 307, pp. 198-205.
Chen et al. "Selection and Analysis of an Optimized Anti-VEGF Antibody: Crystal Structure of an Affinity-matured Fab in Complex with Antigen", Journal of Molecular Biology, 1999, vol. 293, pp. 865-881.
De Pascalis et al., "Grafting of "Abbreviated" Complementarity-Determining Regions Containing Specificity-Determining Residues Essential for Ligand Contact to Engineer a Less Immunogenic Humanized Monoclonal Antibody", The Journal of Immunology, 2002, vol. 169, pp. 3076-3084.
English translation of International Preliminary Report on Patentability and Written Opinion dated Sep. 24, 2015, in PCT International Application No. PCT/JP2014/056526.
Griffon et al., "Identification of the Active Form of Endothelial Lipase, a Homodimer in a Head-to-Tail Conformation", The Journal of Biological Chemistry, Aug. 28, 2009, vol. 284, No. 35, pp. 23322-23330.
Holm et al., "Functional mapping and single chain construction of the anti-cytokeratin 8 monoclonal antibody TS1", Molecular Immunology, 2007, vol. 44, pp. 1075-1084.
International Search Report issued in PCT/JP2014/056526, dated Jun. 10, 2014.
Ishida et al., Endothelial Lipase Modulates Susceptibility to Atherosclerosis in Apolipoprotein-E-deficient Mice, The Journal of Biological Chemistry, The American Society for Biochemistry and Molecular Biology, Inc., Oct. 22, 2004, vol. 279, No. 43. pp. 45085-45092.
Jaye et al., "A novel endothelial-derived lipase that modulates HDL metabolism", Nature Genetics, Apr. 1999, vol. 21, pp. 424-428.
Jin et al., "Inhibition of endothelial lipase causes increased HDL cholesterol levels in vivo", The Journal of Clinical Investigation, Feb. 2003, vol. 111, No. 3, pp. 357-362.
Kojima et al., "Pitavastatin decreases the expression of endothelial lipase both in vitro and in vivo", Cardiovascular Research, 2010, vol. 87, pp. 385-393.

(Continued)

*Primary Examiner* — Zachary C Howard
(74) *Attorney, Agent, or Firm* — Birch, Stewart, Kolasch & Birch, LLP

(57) ABSTRACT

Provided is a monoclonal antibody or a fragment thereof that selectively inhibits the enzymatic activity of vascular endothelial lipase and pharmaceutical compositions containing the same as an active ingredient useful for the treatment of arteriosclerosis or metabolic syndrome.

9 Claims, 24 Drawing Sheets

Specification includes a Sequence Listing.

(56) References Cited

OTHER PUBLICATIONS

MacCallum et al., "Antibody-antigen Interactions: Contact Analysis and Binding Site Topography", Journal of Molecular Biology, 1996, vol. 262, pp. 732-745.
Razzaghi et al., "Genetic and Structure-Function Studies of Missense Mutations in Human Endothelial Lipase", PLOS One, Mar. 2013, vol. 8, Issue No. 3, e55716.
Rudikoff et al., "Single amino acid substitution altering antigen-binding specificity", Proc. Natl Acad. Sci. USA, Immunology, Mar. 1982, vol. 79, pp. 1979-1983.
Vajdos et al., "Comprehensive Functional Maps of the Antigen-binding Site of an Anti-Erb82 Antibody Obtained with Shotgun Scanning Mutagenesis", Journal of Molecular Biology, 2002, vol. 320, pp. 415-428.
Wu et al., "Humanization of a Murine Monoclonal Antibody by Simultaneous Optimization of Framework and CDR Residues", Journal of Molecular Biology, 1999, vol. 294, pp. 151-162.
Yokoyama et al., "Kekkan Naihi Lipase ga Shishitsu Taisha Oyobi Kandomyaku Shikkan e Oyobosu Eikyo ni Kansuru Kenkyu", HEISEI., 16 Nendo Sokatsu Buntan Kenkyu Hokokusho, 2005, pp. 25-26.
Yokoyama et al.,"Study on Impact of Endothelial Lipase on Lipid Metabolism and Coronary Artery Disease," Health Labour Sciences Research Grant Program for Comprehensive Research on Aging and Health, (Mar. 2005), pp. 25-26 (with English translation).
Edmondson et al., "Loss-of-function variants in endothelial lipase are a cause of elevated HDL cholesterol in humans," The Journal of Clinical Investigation (Apr. 2009), vol. 119, No. 4, p. 1042-1050.
Extended European Search Report dated Jan. 19, 2017, in European Patent Application No. 14763470.3.
Griffon et al., "Substrate specificity of lipoprotein lipase and endothelial lipase: studes of lid chimeras," J. Lipid Res. (2006), vol. 47, 1803-1811.
Hirata et al., "Cloning of a Unique Lipase from Endothelial Cells Extends the Lipase Gene Family," The Journal of Biological Chemistry (May 14, 1999), vol. 274, No. 20, pp. 14170-14175.
Ishida et al., "ELISA System for Human Endothelial Lipase," Clinical Chemistry (2012), vol. 58, No. 12, pp. 1656-1664.
Ishida et al., "Endothelial lipase is a major determinant of HDL level," J. Clin. Invest. (2003), vol. 111, pp. 347-355.
Ishida et al., "Molecular cloning of nonsecreted endothelial cell-derived lipase isoforms," Genomics (2004), vol. 83, pp. 24-33.
Jin et al., "Endothelial Cells Secrete Triglyceride Lipase and Phospholipase Activities in Response to Cytokines as a Result of Endothelial Lipase," Circ. Res. (2003), vol. 92, pp. 644-650.
Supplemental Partial European Search Report completed Sep. 6, 2016, in European Patent Application No. 14 76 3470.
Van Tilbeurgh et al., "Lipoprotein Lipase—Molecular model based on the pancreatic lipase X-ray structure: consequences for heparin binding and catalysis," The Journal of Biological Chemistry (Feb. 11, 1994), vol. 269, No. 6, pp. 4626-4633.
Yasuda et al., "Update on the Role of Endothelial Lipase in High-Density Lipoprotein Metabolism, Reverse Cholesterol Transport, and Atherosclerosis," Circ. J. (2010), vol. 74, pp. 2263-2270.

\* cited by examiner

Figure 3K
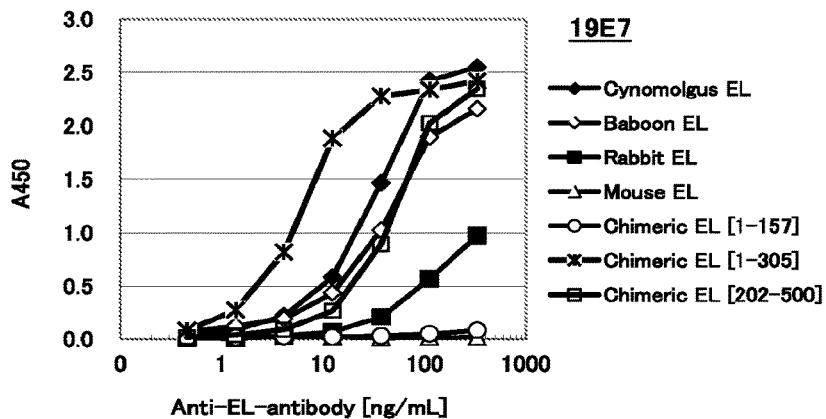
Figure 3L
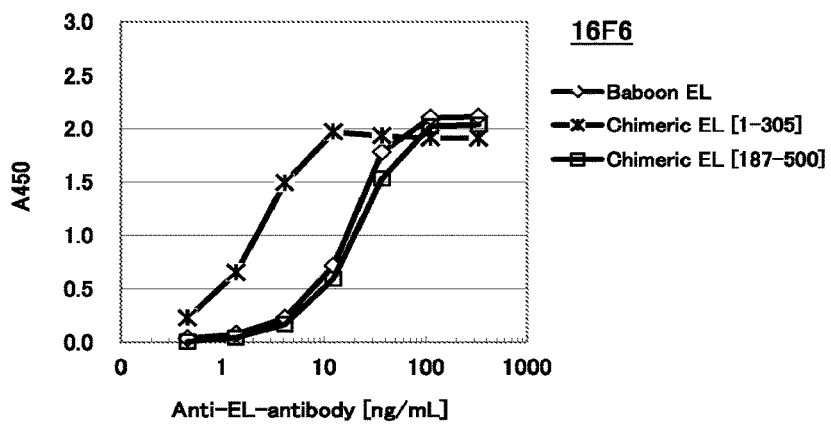
Figure 4A
Heavy chain of 55A1
                                            CDR1                            CDR2
QIHLVQSGPELKKPGETVKISCKASGYTFTNYGMNWVKQAPGKGLKWMGWINTYSGVPTYAGDF
KGRFAFSLETSASTAYLQINNLKNEDTATYFCARRGYYGRRYFDVWGTGTTVTVSS
                                    CDR3
Light chain of 55A1
                                      CDR1                            CDR2
DIVLTQSPASLAVSLGQRATISCKASQSVDYDVDSYMHWYQQKPGQPPKLLIYAASNLASGI
PARFSGGGSGTDFTLNIHPVEEEDVATYYCQQTIEDPPTFGGGTKLEIK
                                CDR3

Figure4B

Heavy chain of 7D4

CDR1         CDR2

QIQLVQSGPELKKPGETVKISCKASGYTFT<u>NYGMN</u>WVKQAPGKDLKWMG<u>WINTYSGVPTYADDF</u>
<u>KG</u>RFAFSLETSASTAYLQINNLKNEDTATYFCAR<u>FSYYGRHYFDY</u>WGQGTTLTVSS
                   CDR3

Light chain of 7D4

CDR1          CDR2

DIVLTQSPASLAVSLGQRATISC<u>KASQSVDYDGDSYMN</u>WYQQKPGQPPQLLIY<u>AASNLGSGI</u>
PARFSGSGSGTDFTLNIHPVEEEDAATYYC<u>HQSTDDPPWT</u>FGGGTKLEIK
              CDR3

Figure4C

Heavy chain of 14A1

CDR1         CDR2

QIQLVQSGPELKKPGETVKISCKASGYTFT<u>NYGMN</u>WVKQAPGKGLKWMG<u>WINTYSGVPTYADDF</u>
<u>KG</u>RFAFSLETSASTAYLQINNFKNEDTATYFCAR<u>FSYYGRHYFDY</u>WGQGTALTASS
                   CDR3

Light chain of 14A1

CDR1          CDR2

DIVLTQSPASLAVSLGQRATISC<u>KASQSVDYDGDSYMN</u>WYQQKPGQPPKLLIY<u>AASNLKSGI</u>
PARFSGSGSGTDFTLNIHPVEEEDAATYYC<u>QQTTDDPPWT</u>FGGGTKLEIK
              CDR3

Figure4D

Heavy chain of 2D5

CDR1         CDR2

QIQLVQSGPELKKPGETVKISCKASGYTFT<u>NYGMN</u>WVKQAPGKGLKWMG<u>WINTYSGVPTYTDDF</u>
<u>KG</u>RFAFSLETSASTAFLQINNLKNEDTATYFCAR<u>FSYYGRHYFDY</u>WGQGTTLTVSS
                   CDR3

Light chain of 2D5

CDR1          CDR2

DIVLTQSPASLAVSLGQRATISC<u>KASQSVDYDGDSYMH</u>WYQQKPGQPPKLLIY<u>AASNLESGI</u>
PARFSGSGSGTDFTLNIHPVEEEDAATYYC<u>QQTNDDPPWT</u>FGGGTKLEIK
              CDR3

Figure4E

Heavy chain of 53A11

CDR1                          CDR2
EVQLQQSGPELLKPGASVKISCKASGYTFT<u>DYTMH</u>WVKQSHGKSLEWIG<u>GINPYYGGTTYNEKF</u>
<u>K</u>DKATLTVDKSSSTAYMELRSLTSEDSAVYYCAK<u>GDYYGGSYNY</u>WGQGTTLTVSS
                                        CDR3

Light chain of 53A11

CDR1                          CDR2
DIVLTQSLATLSVTPGDSVSLSC<u>RASQDISNSLH</u>WYQQKSHESPRLLIK<u>YASQSIS</u>GIPSRF
SGSGSGTDFTLSINSVETEDFGMYFC<u>QQSNSWPYT</u>FGGGTKLEIK
                              CDR3

Figure4F

Heavy chain of 13B3

CDR1                          CDR2
EVQLQQSGPELLKPGASVKISCKASGYTFT<u>EYTMH</u>WVKQSHGKSLEWIG<u>SINPYYGGTSYNEKF</u>
<u>K</u>DKATLTVDKSSNTAYMEFRSLTSEDCAVYYCAR<u>YGNYVGYFDY</u>WGQGTTLTVSS
                                        CDR3

Light chain of 13B3

CDR1                          CDR2
ENVLTQSPAIMSASLGEKVTMSC<u>RASSSVHYMY</u>WYQQKSDASPKLWIY<u>YTSNLAP</u>GVPDRFS
GSGSGNSYSLTISSMEGEDAATYYC<u>QQFTSSPYT</u>FGGGTKLEIK
                              CDR3

Figure4G

Heavy chain of 23H8

CDR1                          CDR2
EVQLQQSGPELLKPGASVKISCKASGYTFT<u>DNTIH</u>WVKQSHGKSLEWIG<u>HINPYYGGTNNNEKF</u>
<u>K</u>DKATLTVDKSSSTAYMELRSLTSEDSAIYYCAR<u>KGIYYSSPFDY</u>WGQGTTLTVSS
                                        CDR3

Light chain of 23H8

CDR1                          CDR2
DIQMTQTTSSLSASLGDRVTISC<u>RASQDINNYLN</u>WYQQKPDGTVKLLIS<u>YTSKLHS</u>GVPS

RFSGSGSGTDYSLTISNLEREDFATYFC<u>QQGNTLPFT</u>FGSGTNLEIK
                                CDR3

Figure 4H

Heavy chain of 16B3

CDR1                          CDR2
DVKLVESGGGLVQPGGSLKLSCTASGFTFSGYTMSWVRQTPEKRLELVAEISFARDRAFYPDTV
KGRFTISRDNAKNTLYLQMSSLKSEDTAMYYCTRLGGRNHDYWYFDVWGTGTTVTVSS
                                          CDR3

Light chain of 16B3

CDR1                          CDR2
DIVLTQSPTSLAVSPGQRATISCRASESVEYYGTSLMQWYQQKPGQRPQLLIYAASNVESGV
PARFSGSGSGTDFSLNIHPVEEDDIAVYFCQQSWKVPFTFGSGTKLEIK
                                     CDR3

Figure 4I

Heavy chain of 16E7

CDR1                          CDR2
EVKLVESGGGLVQPGGSLKLSCAASGFTFSSYTMSWVRQTPEKRLELVAEISFTRSRAFYPDTV
KGRFTISRDNAKNTLYLQMSSLKSEDTAMYYCARLGGNNYDYWYFDVWGTGTTVTVSS
                                          CDR3

Light chain of 16E7

CDR1                          CDR2
DIVLTQSPTSLAVSLGQRATISCRASESVEYYGTSLMQWYQQKPGQRPKLLIYAASNVESGV
PARFSGSGSGTDFSLNIHPVEEDDIAMYFCQQSWKVPFTFGSGTKLEIK
                                     CDR3

Figure 4J

Heavy chain of 14E1

CDR1                          CDR2
QVQLQQSGAELVKPGASVRLSCKASGYTFTKYTIHWVKQRSGQGLEWIGWFYPGSDSIKYNEKF
KDKATLTADKSSRTVYMELSRLTSEDSAVYFCARHEEYTNSLAYWGQGTLVTVSA
                                     CDR3

Light chain of 14E1

CDR1                          CDR2
DIQMTQTTSSLSASLGDRVTISCRASQDISNYLNWYQQQPDGTVKLLIYYTSRLHSGVPSRF
SGSGSGTDYSLTISNLEQEDIATYFCQQGYTLPWTFGGGTNLEIK
                                CDR3

Figure4K

Heavy chain of 19E7

CDR1                    CDR2

QVQLQQPGSVLVRPGASVKLSCKASGYTFT<u>TYWMH</u>WVKQRPGQGLEWIG<u>EIHPYSGNNNNNEKF</u>
<u>KG</u>KATLTVDTSSSTAYVDLSRLTSEDSAVYYCAR<u>YDSNYVFAY</u>WGQGTLVTVSA
                                    CDR3

Light chain of 19E7

CDR1                CDR2

QIVLTQSPAIMSASPGEGVTITC<u>SASSSVSYMH</u>WFQQKPGTSPKLWIY<u>STSNLAS</u>GVPARFS
GSGSGTSYSLTISRMEAEDAATYYC<u>QQRDSYLT</u>FGSGTKLEVK
                           CDR3

Figure4L

Heavy chain of 16F6
                                    CDR1                 CDR2
QVQLQQSGAELMKPGASVKISCKATGYTFS<u>TYWIA</u>WVKQRPGHGLEWIG<u>EILPGSAKTKYNKKF</u>
<u>KG</u>KATFTADTSSNTAYMQLSSLTSEDSAVYYCAV<u>YDYGADY</u>WGQGTSVTVSS
                                    CDR3

Light chain of 16F6    CDR1                          CDR2
DIVMTQSHKFMSTSVGDRVSITC<u>KASQDVYTAVA</u>WYQQKPGQSPKLLIY<u>SASYRFT</u>GVPDRF
TGSGAGTEFTFTINSVQAEDLAVYYC<u>QQHYSIPRT</u>FGGGTKLEIK
                           CDR3

Figure5A

| | | |
|---|---|---|
| 55A1 | 1:QIHLVQSGPELKKPGETVKISCKASGYTFT<u>NYGMN</u>WVKQAPGKGLKWMG<u>WINTYSGVPTY</u> | 60 |
| 7D4 | 1:QIQLVQSGPELKKPGETVKISCKASGYTFT<u>NYGMN</u>WVKQAPGKDLKWMG<u>WINTYSGVPTY</u> | 60 |
| 14A1 | 1:QIQLVQSGPELKKPGETVKISCKASGYTFT<u>NYGMN</u>WVKQAPGKGLKWMG<u>WINTYSGVPTY</u> | 60 |
| 2D5 | 1:QIQLVQSGPELKKPGETVKISCKASGYTFT<u>NYGMN</u>WVKQAPGKGLKWMG<u>WINTYSGVPTY</u> | 60 |
| 55A1 | 61:<u>AGDFKG</u>RFAFSLETSASTAYLQINNLKNEDTATYFCAR<u>RGYYGRRYFDV</u>WGTGTTVTVSS | 120 |
| 7D4 | 61:<u>ADDFKG</u>RFAFSLETSASTAYLQINNLKNEDTATYFCAR<u>FSYYGRHYFDY</u>WGQGTTLTVSS | 120 |
| 14A1 | 61:<u>ADDFKG</u>RFAFSLETSASTAYLQINNFKNEDTATYFCAR<u>FSYYGRHYFDY</u>WGQGTALTASS | 120 |
| 2D5 | 61:<u>TDDFKG</u>RFAFSLETSASTAFLQINNLKNEDTATYFCAR<u>FSYYGRHYFDY</u>WGQGTTLTVSS | 120 |

Figure5B

```
55A1    1:DIVLTQSPASLAVSLGQRATISCKASQSVDYDVDSYMHWYQQKPGQPPKLLIYAASNLAS  60
7D4     1:DIVLTQSPASLAVSLGQRATISCKASQSVDYDGDSYMNWYQQKPGQPPQLLIYAASNLGS  60
14A1    1:DIVLTQSPASLAVSLGQRATISCKASQSVDYDGDSYMNWYQQKPGQPPKLLIYAASNLKS  60
2D5     1:DIVLTQSPASLAVSLGQRATISCKASQSVDYDGDSYMHWYQQKPGQPPKLLIYAASNLES  60

55A1   61:GIPARFSGGGSGTDFTLNIHPVEEEDVATYYCQQTIEDPP-TFGGGTKLEIK         111
7D4    61:GIPARFSGSGSGTDFTLNIHPVEEEDAATYYCHQSTDDPPWTFGGGTKLEIK         112
14A1   61:GIPARFSGSGSGTDFTLNIHPVEEEDAATYYCQQTTDDPPWTFGGGTKLEIK         112
2D5    61:GIPARFSGSGSGTDFTLNIHPVEEEDAATYYCQQTNDDPPWTFGGGTKLEIK         112
```

Figure5C

```
53A11   1:EVQLQQSGPELLKPGASVKISCKASGYTFTDYTMHWVKQSHGKSLEWIGGINPYYGGTTY  60
13B3    1:EVQLQQSGPELLKPGASVKISCKASGYTFTEYTMHWVKQSHGKSLEWIGSINPYYGGTSY  60
23H8    1:EVQLQQSGPELLKPGASVKISCKASGYTFTDNTIHWVKQSHGKSLEWIGHINPYYGGTNN  60

53A11  61:NEKFKDKATLTVDKSSSTAYMELRSLTSEDSAVYYCAKGD-YYGGSYNYWGQGTTLTVSS 119
13B3   61:NEKFKDKATLTVDKSSNTAYMEFRSLTSEDCAVYYCARYG-NYVGYFDYWGQGTTLTVSS 119
23H8   61:NEKFKDKATLTVDKSSSTAYMELRSLTSEDSAIYYCARKGIYYSSPFDYWGQGTTLTVSS 120
```

Figure5D

```
53A11   1:DIVLTQSLATLSVTPGDSVSLSCRASQDISNSLHWYQQKSHESPRLLIKYASQSISGIPS  60
13B3    1:ENVLTQSPAIMSASLGEKVTMSCRASSSV-HYMYWYQQKSDASPKLWIYYTSNLAPGVPD  59
23H8    1:DIQMTQTTSSLSASLGDRVTISCRASQDINNYLNWYQQKPDGTVKLLISYTSKLHSGVPS  60

53A11  61:RFSGSGSGTDFTLSINSVETEDFGMYFCQQSNSWPYTFGGGTKLEIK              107
13B3   60:RFSGSGSGNSYSLTISSMEGEDAATYYCQQFTSSPYTFGGGTKLEIK              106
23H8   61:RFSGSGSGTDYSLTISNLEREDFATYFCQQGNTLPFTFGSGTNLEIK              107
```

Figure6A

```
16B3    1:DVKLVESGGGLVQPGGSLKLSCTASGFTFSGYTMSWVRQTPEKRLELVAEISFARDRAFY 60
16E7    1:EVKLVESGGGLVQPGGSLKLSCAASGFTFSSYTMSWVRQTPEKRLELVAETSFTRSRAFY 60

16B3   61:PDTVKGRFTISRDNAKNTLYLQMSSLKSEDTAMYYCTRLGGRNHDYWYFDVWGTGTTVTV 120
16E7   61:PDTVKGRFTISRDNAKNTLYLQMSSLKSEDTAMYYCARLGGNNYDYWYFDVWGTGTTVTV 120

```
16B3    1:DIVLTQSPTSLAVSPGQRATISCRASESVEYYGTSLMQWYQQKPGQRPQLLIYAASNVES 60
16E7    1:DIVLTQSPTSLAVSLGQRATISCRASESVEYYGTSLMQWYQQKPGQRPKLLIYAASNVES 60

16B3   61:GVPARFSGSGSGTDFSLNIHPVEEDDIAVYFCQQSWKVPFTFGSGTKLEIK          111
16E7   61:GVPARFSGSGSGTDFSLNIHPVEEDDIAMYFCQQSWKVPFTFGSGTKLEIK          111
```

Figure6C

```
14E1    1:QVQLQQSGAELVKPGASVRLSCKASGYTFTKYTIHWVKQRSGQGLEWIGWFYPGSDSIKY 60
19E7    1:QVQLQQPGSVLVRPGASVKLSCKASGYTFTTYWMHWVKQRPGQGLEWIGEIHPYSGNNNN 60

14E1   61:NEKFKDKATLTADKSSRTVYMELSRLTSEDSAVYFCARHEEYTNSLAYWGQGTLVTVSA  119
19E7   61:NEKFKGKATLTVDTSSTAYVDLSRLTSEDSAVYYCARYDS-NYVFAYWGQGTLVTVSA   118
```

Figure6D

```
14E1    1:DIQMTQTTSSLSASLGDRVTISCRASQDISNYLNWYQQQPDGTVKLLIYYTSRLHSGVPS 60
19E7    1:QIVLTQSPAIMSASPGEGVTITCSASSSVS-YMHWFQQKPGTSPKLWIYSTSNLASGVPA 59

14E1   61:RFSGSGSGTDYSLTISNLEQEDIATYFCQQGYTLPWTFGGGTNLEIK              107
19E7   60:RFSGSGSGTSYSLTISRMEAEDAATYYCQQRDSY-LTFGSGTKLEVK              105
```

MONOCLONAL ANTIBODY, INHIBITING THE ENZYMATIC ACTIVITY OF VASCULAR ENDOTHELIAL LIPASE

CROSS-REFERENCE TO RELATED APPLICATIONS

The present application is a 37 C.F.R. § 1.53(b) divisional of U.S. application Ser. No. 14/772,340 filed Sep. 2, 2015, which is the National Phase of PCT International Application No. PCT/JP2014/056526 filed Mar. 12, 2014, which claims priority on Japanese Patent Application No. 2013-051995 filed Mar. 14, 2013. The entire contents of each of these application is hereby incorporated by reference.

TECHNICAL FIELD

The present invention relates to a monoclonal antibody that inhibits the enzymatic activity of vascular endothelial lipase (hereinafter, referred to also EL) and pharmaceutical compositions containing the same. More specifically, the present invention relates to an antibody that selectively inhibits the enzymatic activity of EL, or a part thereof, and a pharmaceutical composition containing the same.

BACKGROUND ART

EL is a phospholipase that belongs to triglyceride lipase (hereinafter, referred to TG) family (non-patent literature: 1). Human EL consists of 500 amino acids (NCBI Accession number NP_006024.1, SEQ ID NO: 1) and rabbit EL consists of 500 amino acids (NCBI Accession number NO_001182567, SEQ ID NO: 2). Lipoprotein lipase (hereinafter, referred to LPL) and hepatic lipase (hereinafter, referred to HL) is contained by TG family.

The analysis of EL knockout mouse and EL transgenic mouse revealed that EL relates to HDL cholesterol (hereinafter, referred to HDL-c) metabolism by its strong phospholipase activity, and have been a focus as a factor which controls HDL-c level in blood (non-patent literature: 2). It has been well-known that there is a negative correlation between coronary artery disease (hereinafter, referred to CAD) and HDL-c level in blood. HDL-c shows anti-atherogenic effect through antioxidant effect, anti-inflammatory effect and reverse cholesterol transport and so on, low HDL-c emia is recognized as one of the risk factor of CAD. Therefore, EL inhibitor could become a therapeutic agent for CAD through increasing HDL-c in blood. In fact, it was reported that lesion mouse of EL knockout increased HDL-c and decreased atherosclerotic lesions (non-patent literature: 3).

These findings indicate that a selective EL inhibitor is useful as therapeutic agent for abnormality of lipid metabolism and arteriosclerosis.

A selective inhibition of EL is useful as therapeutic agent for abnormality of lipid metabolism and arteriosclerosis, so a production of EL antibodies which inhibit EL activity is one of the important approaches. So far, it has been reported that a rabbit polyclonal antibody which inhibits EL activity was prepared, HDL-c level in mouse blood increased after administrating of the antibody (non-patent literature: 4).

Polyclonal antibodies recognize various regions of EL and do not have a high selectivity against EL. Also, it is impossible to use rabbit anti-EL polyclonal antibodies having high immunogenicity to human as therapeutic agent for chronic diseases because therapeutic agents for chronic diseases such as the abnormality of lipid metabolism and arteriosclerosis related to EL have to be administrated for a long term. Moreover, it is difficult to manipulate immunogenicity of polyclonal antibodies.

By these circumstances, a monoclonal antibody inhibiting selectively the enzymatic activity of EL is awaited.

Non-patent document 1: Nature Genetics., 1999, vol. 21, p. 424
Non-patent document 2: TCM., 2004, vol. 14(5), p. 202-206
Non-patent document 3: The Journal of Biological Chemistry., 2004, vol. 279, No. 43, 22 p. 45085-45092
Non-patent document 4: J. Clin. Invest., 2003, Vol. 111(3), p. 357

SUMMARY OF THE INVENTION

Problem to be Solved by the Invention

An objective of the present invention is to provide an antibody that selectively inhibits enzyme activity of EL, or a an antibody fragment thereof, and a pharmaceutical composition containing the same.

Means for Solving the Problem

As a result of diligent efforts, the present inventors have succeeded in finding a monoclonal antibody that selectively inhibits the enzymatic activity of EL.

To be more specific, the present invention relates to:
(1) A monoclonal antibody that inhibits the enzymatic activity of vascular endothelial lipase or an antibody fragment thereof, wherein it recognizes at least one amino acid at positions of 1 to 157 in an amino acid sequence of SEQ ID NO: 1.
(2) The monoclonal antibody of (1) or the antibody fragment thereof, wherein it recognizes at least one amino acid at positions of 50 to100 in an amino acid sequence of SEQ ID NO: 1.
(3) The monoclonal antibody of (1) or (2) or the antibody fragment thereof, wherein it recognizes at least one amino acid selected from arginine at position 50, glutamic acid at position 60, tyrosine at position 65 and asparagine at position 100 in an amino acid sequence of SEQ ID NO: 1.
(4) The monoclonal antibody of (1) or (2) or the antibody fragment thereof, wherein it recognizes at least tyrosine at position 65 in an amino acid sequence of SEQ ID NO: 1.
(5) The monoclonal antibody of (4) or the antibody fragment thereof, wherein it recognizes at least one amino acid selected from arginine at position 50, asparagine at position 52, arginine at position 54, aspartic acid at position 58, glutamic acid at position 60, histidine at position 61, glycine at position 63 and asparagine at position 100 in an amino acid sequence of SEQ ID NO: 1.
(6) A monoclonal antibody that inhibits the enzymatic activity of vascular endothelial lipase or an antibody fragment thereof, wherein it recognizes at least one amino acid at positions of 202 to 305 in an amino acid sequence of SEQ ID NO: 1.
(7) The monoclonal antibody of (6) or the antibody fragment thereof, wherein it recognizes at least one amino acid at positions of 220 to 273 in an amino acid sequence of SEQ ID NO: 1.
(8) The monoclonal antibody of (6) or (7) or the antibody fragment thereof, wherein it recognizes at least one amino acid selected from histidine at position 220, threonine at position 221, tyrosine at position 222, threonine at position 223, arginine at position 224, phenylalanine at position 226, glycine at position 227, glycine at position 231, isoleucine at position 232, glutamine at position 233, methionine at position 234, aspartic acid at position 240, tyrosine at position 242, proline at position 243, asparagine at position 244, glycine at position 246, glutamine at position 249, proline at position 250, glycine at position 251, leucine at position 254, leucine at position 258, tyrosine at position 263, valine at position 269 and glutamic acid at position 273 in an amino acid sequence of SEQ ID NO: 1.

(9) The monoclonal antibody of (6) or (7) or the antibody fragment thereof, wherein it recognizes at least one amino acid selected from histidine at position 220, threonine at position 221, aspartic acid at position 240, tyrosine at position 242, proline at position 243, asparagine at position 244, glycine at position 246, glutamine at position 249, proline at position 250, and glycine at position 251 in an amino acid sequence of SEQ ID NO: 1.

(10) The monoclonal antibody of (6) or (7) or the antibody fragment thereof, wherein it recognizes all amino acids of histidine at position 220, threonine at position 221, aspartic acid at position 240, tyrosine at position 242, proline at position 243, asparagine at position 244, glycine at position 246, glutamine at position 249, proline at position 250 and glycine at position 251 in an amino acid sequence of SEQ ID NO: 1.

(11) The monoclonal antibody of any one of (1) to (10), wherein it inhibits the enzymatic activity of vascular endothelial lipase with an IC 50 of 10 nM or less.

(12) The monoclonal antibody of (11), wherein it inhibits the enzymatic activity of vascular endothelial lipase with an IC 50 of 5 nM or less.

(13) The monoclonal antibody of (11), wherein it inhibits the enzymatic activity of vascular endothelial lipase with an IC 50 of 2 nM or less.

(14) A monoclonal antibody or a fragment thereof, selected from the group of

1) A monoclonal antibody or a fragment thereof, having
  a heavy chain variable region including three CDRs comprising amino acid sequence of SEQ ID NO: 10, amino acid sequence of SEQ ID NO: 11 and amino acid sequence of SEQ ID NO: 12 and
  a light chain variable region including three CDRs comprising amino acid sequence of SEQ ID NO: 14, amino acid sequence of SEQ ID NO: 15 and amino acid sequence of SEQ ID NO: 16.

2) A monoclonal antibody or a fragment thereof, having
  a heavy chain variable region including three CDRs comprising amino acid sequence of SEQ ID NO: 10, amino acid sequence of SEQ ID NO: 11 and amino acid sequence of SEQ ID NO: 12 and
  a light chain variable region including three CDRs, said three CDRs consisting of amino acids that are one or several amino acids are deleted, substituted or added in at least one of the three CDRs, said the three CDRs comprising amino acid sequence of SEQ ID NO: 14, amino acid sequence of SEQ ID NO: 15 and amino acid sequence of SEQ ID NO: 16, and
inhibiting the enzymatic activity of vascular endothelial lipase.

3) A monoclonal antibody or a fragment thereof, having
  a heavy chain variable region including three CDRs, said three CDRs consisting of amino acids that are one or several amino acids are deleted, substituted or added in at least one of the three CDRs, said the three CDRs comprising amino acid sequence of SEQ ID NO: 10, amino acid sequence of SEQ ID NO: 11 and amino acid sequence of SEQ ID NO: 12, and
  a light chain variable region including three CDRs comprising amino acid sequence of SEQ ID NO: 14, amino acid sequence of SEQ ID NO: 15 and amino acid sequence of SEQ ID NO: 16, and
inhibiting the enzymatic activity of vascular endothelial lipase.

4) A monoclonal antibody or a fragment thereof, having
  a heavy chain variable region including three CDRs, said three CDRs consisting of amino acids that are one or several amino acids are deleted, substituted or added in at least one of the three CDRs, said the three CDRs comprising amino acid sequence of SEQ ID NO: 10, amino acid sequence of SEQ ID NO: 11 and amino acid sequence of SEQ ID NO: 12, and
  a light chain variable region including three CDRs, said three CDRs consisting of amino acids that are one or several amino acids are deleted, substituted or added in at least one of the three CDRs, said three CDRs comprising amino acid sequence of SEQ ID NO: 14, amino acid sequence of SEQ ID NO: 15 and amino acid sequence of SEQ ID NO: 16, and
inhibiting the enzymatic activity of vascular endothelial lipase.

5) A monoclonal antibody or a fragment thereof, having
  a heavy chain variable region including three CDRs comprising amino acid sequence of SEQ ID NO: 18, amino acid sequence of SEQ ID NO: 19 and amino acid sequence of SEQ ID NO: 20 and
  a light chain variable region including three CDRs comprising amino acid sequence of SEQ ID NO: 22, amino acid sequence of SEQ ID NO: 23 and amino acid sequence of SEQ ID NO: 24.

6) A monoclonal antibody or a fragment thereof, having
  a heavy chain variable region including three CDRs comprising amino acid sequence of SEQ ID NO: 18, amino acid sequence of SEQ ID NO: 19 and amino acid sequence of SEQ ID NO: 20 and
  a light chain variable region including three CDRs, said three CDRs consisting of amino acids that are one or several amino acids are deleted, substituted or added in at least one of the three CDRs, said the three CDRs comprising amino acid sequence of SEQ ID NO: 22, amino acid sequence of SEQ ID NO: 23 and amino acid sequence of SEQ ID NO: 24, and
inhibiting the enzymatic activity of vascular endothelial lipase.

7) A monoclonal antibody or a fragment thereof, having
  a heavy chain variable region including three CDRs, said three CDRs consisting of amino acids that are one or several amino acids are deleted, substituted or added in at least one of the three CDRs, said the three CDRs comprising amino acid sequence of SEQ ID NO: 18, amino acid sequence of SEQ ID NO: 19 and amino acid sequence of SEQ ID NO: 20, and
  a light chain variable region including three CDRs comprising amino acid sequence of SEQ ID NO: 22, amino acid sequence of SEQ ID NO: 23 and amino acid sequence of SEQ ID NO: 24, and
inhibiting the enzymatic activity of vascular endothelial lipase.

8) A monoclonal antibody or a fragment thereof, having
- a heavy chain variable region including three CDRs, said three CDRs consisting of amino acids that are one or several amino acids are deleted, substituted or added in at least one of the three CDRs, said the three CDRs comprising amino acid sequence of SEQ ID NO: 18, amino acid sequence of SEQ ID NO: 19 and amino acid sequence of SEQ ID NO: 20, and
- a light chain variable region including three CDRs, said three CDRs consisting of amino acids that are one or several amino acids are deleted, substituted or added in at least one of the three CDRs, said three CDRs comprising amino acid sequence of SEQ ID NO: 22, amino acid sequence of SEQ ID NO: 23 and amino acid sequence of SEQ ID NO: 24, and inhibiting the enzymatic activity of vascular endothelial lipase.

9) A monoclonal antibody or a fragment thereof, having
- a heavy chain variable region including three CDRs comprising amino acid sequence of SEQ ID NO: 26, amino acid sequence of SEQ ID NO: 27 and amino acid sequence of SEQ ID NO: 28 and
- a light chain variable region including three CDRs comprising amino acid sequence of SEQ ID NO: 30, amino acid sequence of SEQ ID NO: 31 and amino acid sequence of SEQ ID NO: 32.

10) A monoclonal antibody or a fragment thereof, having
- a heavy chain variable region including three CDRs comprising amino acid sequence of SEQ ID NO: 26, amino acid sequence of SEQ ID NO: 27 and amino acid sequence of SEQ ID NO: 28 and
- a light chain variable region including three CDRs, said three CDRs consisting of amino acids that are one or several amino acids are deleted, substituted or added in at least one of the three CDRs, said the three CDRs comprising amino acid sequence of SEQ ID NO: 30, amino acid sequence of SEQ ID NO: 31 and amino acid sequence of SEQ ID NO: 32, and inhibiting the enzymatic activity of vascular endothelial lipase.

11) A monoclonal antibody or a fragment thereof, having
- a heavy chain variable region including three CDRs, said three CDRs consisting of amino acids that are one or several amino acids are deleted, substituted or added in at least one of the three CDRs, said the three CDRs comprising amino acid sequence of SEQ ID NO: 26, amino acid sequence of SEQ ID NO: 27 and amino acid sequence of SEQ ID NO: 28, and
- a light chain variable region including three CDRs comprising amino acid sequence of SEQ ID NO: 30, amino acid sequence of SEQ ID NO: 31 and amino acid sequence of SEQ ID NO: 32, and inhibiting the enzymatic activity of vascular endothelial lipase.

12) A monoclonal antibody or a fragment thereof, having
- a heavy chain variable region including three CDRs, said three CDRs consisting of amino acids that are one or several amino acids are deleted, substituted or added in at least one of the three CDRs, said the three CDRs comprising amino acid sequence of SEQ ID NO: 26, amino acid sequence of SEQ ID NO: 27 and amino acid sequence of SEQ ID NO: 28, and
- a light chain variable region including three CDRs, said three CDRs consisting of amino acids that are one or several amino acids are deleted, substituted or added in at least one of the three CDRs, said three CDRs comprising amino acid sequence of SEQ ID NO: 30, amino acid sequence of SEQ ID NO: 31 and amino acid sequence of SEQ ID NO: 32, and inhibiting the enzymatic activity of vascular endothelial lipase.

13) A monoclonal antibody or a fragment thereof, having
- a heavy chain variable region including three CDRs comprising amino acid sequence of SEQ ID NO: 34, amino acid sequence of SEQ ID NO: 35 and amino acid sequence of SEQ ID NO: 36 and
- a light chain variable region including three CDRs comprising amino acid sequence of SEQ ID NO: 38, amino acid sequence of SEQ ID NO: 39 and amino acid sequence of SEQ ID NO: 40.

14) A monoclonal antibody or a fragment thereof, having
- a heavy chain variable region including three CDRs comprising amino acid sequence of SEQ ID NO: 34, amino acid sequence of SEQ ID NO: 35 and amino acid sequence of SEQ ID NO: 36 and
- a light chain variable region including three CDRs, said three CDRs consisting of amino acids that are one or several amino acids are deleted, substituted or added in at least one of the three CDRs, said the three CDRs comprising amino acid sequence of SEQ ID NO: 38, amino acid sequence of SEQ ID NO: 39 and amino acid sequence of SEQ ID NO: 40, and inhibiting the enzymatic activity of vascular endothelial lipase.

15) A monoclonal antibody or a fragment thereof, having
- a heavy chain variable region including three CDRs, said three CDRs consisting of amino acids that are one or several amino acids are deleted, substituted or added in at least one of the three CDRs, said the three CDRs comprising amino acid sequence of SEQ ID NO: 34, amino acid sequence of SEQ ID NO: 35 and amino acid sequence of SEQ ID NO: 36, and
- a light chain variable region including three CDRs comprising amino acid sequence of SEQ ID NO: 38, amino acid sequence of SEQ ID NO: 39 and amino acid sequence of SEQ ID NO: 40, and inhibiting the enzymatic activity of vascular endothelial lipase.

16) A monoclonal antibody or a fragment thereof, having
- a heavy chain variable region including three CDRs, said three CDRs consisting of amino acids that are one or several amino acids are deleted, substituted or added in at least one of the three CDRs, said the three CDRs comprising amino acid sequence of SEQ ID NO: 34, amino acid sequence of SEQ ID NO: 35 and amino acid sequence of SEQ ID NO: 36, and
- a light chain variable region including three CDRs, said three CDRs consisting of amino acids that are one or several amino acids are deleted, substituted or added in at least one of the three CDRs, said three CDRs comprising amino acid sequence of SEQ ID NO: 38, amino acid sequence of SEQ ID NO: 39 and amino acid sequence of SEQ ID NO: 40, and inhibiting the enzymatic activity of vascular endothelial lipase.

17) A monoclonal antibody or a fragment thereof, having
- a heavy chain variable region including three CDRs comprising amino acid sequence of SEQ ID NO: 42, amino acid sequence of SEQ ID NO: 43 and amino acid sequence of SEQ ID NO: 44 and
- a light chain variable region including three CDRs comprising amino acid sequence of SEQ ID NO: 46, amino acid sequence of SEQ ID NO: 47 and amino acid sequence of SEQ ID NO: 48.

18) A monoclonal antibody or a fragment thereof, having
- a heavy chain variable region including three CDRs comprising amino acid sequence of SEQ ID NO: 42, amino acid sequence of SEQ ID NO: 43 and amino acid sequence of SEQ ID NO: 44 and
- a light chain variable region including three CDRs, said three CDRs consisting of amino acids that are one or several amino acids are deleted, substituted or added in at least one of the three CDRs, said the three CDRs comprising amino acid sequence of SEQ ID NO: 46, amino acid sequence of SEQ ID NO: 47 and amino acid sequence of SEQ ID NO: 48, and inhibiting the enzymatic activity of vascular endothelial lipase.

19) A monoclonal antibody or a fragment thereof, having
- a heavy chain variable region including three CDRs, said three CDRs consisting of amino acids that are one or several amino acids are deleted, substituted or added in at least one of the three CDRs, said the three CDRs comprising amino acid sequence of SEQ ID NO: 42, amino acid sequence of SEQ ID NO: 43 and amino acid sequence of SEQ ID NO: 44, and
- a light chain variable region including three CDRs comprising amino acid sequence of SEQ ID NO: 46, amino acid sequence of SEQ ID NO: 47 and amino acid sequence of SEQ ID NO: 48, and inhibiting the enzymatic activity of vascular endothelial lipase.

20) A monoclonal antibody or a fragment thereof, having
- a heavy chain variable region including three CDRs, said three CDRs consisting of amino acids that are one or several amino acids are deleted, substituted or added in at least one of the three CDRs, said the three CDRs comprising amino acid sequence of SEQ ID NO: 42, amino acid sequence of SEQ ID NO: 43 and amino acid sequence of SEQ ID NO: 44, and
- a light chain variable region including three CDRs, said three CDRs consisting of amino acids that are one or several amino acids are deleted, substituted or added in at least one of the three CDRs, said three CDRs comprising amino acid sequence of SEQ ID NO: 46, amino acid sequence of SEQ ID NO: 47 and amino acid sequence of SEQ ID NO: 48, and inhibiting the enzymatic activity of vascular endothelial lipase.

21) A monoclonal antibody or a fragment thereof, having
- a heavy chain variable region including three CDRs comprising amino acid sequence of SEQ ID NO: 50, amino acid sequence of SEQ ID NO: 51 and amino acid sequence of SEQ ID NO: 52 and
- a light chain variable region including three CDRs comprising amino acid sequence of SEQ ID NO: 54, amino acid sequence of SEQ ID NO: 55 and amino acid sequence of SEQ ID NO: 56.

22) A monoclonal antibody or a fragment thereof, having
- a heavy chain variable region including three CDRs comprising amino acid sequence of SEQ ID NO: 50, amino acid sequence of SEQ ID NO: 51 and amino acid sequence of SEQ ID NO: 52 and
- a light chain variable region including three CDRs, said three CDRs consisting of amino acids that are one or several amino acids are deleted, substituted or added in at least one of the three CDRs, said the three CDRs comprising amino acid sequence of SEQ ID NO: 54, amino acid sequence of SEQ ID NO: 55 and amino acid sequence of SEQ ID NO: 56, and inhibiting the enzymatic activity of vascular endothelial lipase.

23) A monoclonal antibody or a fragment thereof, having
- a heavy chain variable region including three CDRs, said three CDRs consisting of amino acids that are one or several amino acids are deleted, substituted or added in at least one of the three CDRs, said the three CDRs comprising amino acid sequence of SEQ ID NO: 50, amino acid sequence of SEQ ID NO: 51 and amino acid sequence of SEQ ID NO: 52, and
- a light chain variable region including three CDRs comprising amino acid sequence of SEQ ID NO: 54, amino acid sequence of SEQ ID NO: 55 and amino acid sequence of SEQ ID NO: 56, and inhibiting the enzymatic activity of vascular endothelial lipase.

24) A monoclonal antibody or a fragment thereof, having
- a heavy chain variable region including three CDRs, said three CDRs consisting of amino acids that are one or several amino acids are deleted, substituted or added in at least one of the three CDRs, said the three CDRs comprising amino acid sequence of SEQ ID NO: 50, amino acid sequence of SEQ ID NO: 51 and amino acid sequence of SEQ ID NO: 52, and
- a light chain variable region including three CDRs, said three CDRs consisting of amino acids that are one or several amino acids are deleted, substituted or added in at least one of the three CDRs, said three CDRs comprising amino acid sequence of SEQ ID NO: 54, amino acid sequence of SEQ ID NO: 55 and amino acid sequence of SEQ ID NO: 56, and inhibiting the enzymatic activity of vascular endothelial lipase.

25) A monoclonal antibody or a fragment thereof, having
- a heavy chain variable region including three CDRs comprising amino acid sequence of SEQ ID NO: 58, amino acid sequence of SEQ ID NO: 59 and amino acid sequence of SEQ ID NO: 60 and
- a light chain variable region including three CDRs comprising amino acid sequence of SEQ ID NO: 62, amino acid sequence of SEQ ID NO: 63 and amino acid sequence of SEQ ID NO: 64.

26) A monoclonal antibody or a fragment thereof, having
- a heavy chain variable region including three CDRs comprising amino acid sequence of SEQ ID NO: 58, amino acid sequence of SEQ ID NO: 59 and amino acid sequence of SEQ ID NO: 60 and a light chain variable region including three CDRs, said three CDRs consisting of amino acids that are one or several amino acids are deleted, substituted or added in at least one of the three CDRs, said the three CDRs comprising amino acid sequence of SEQ ID NO: 62, amino acid sequence of SEQ ID NO: 63 and amino acid sequence of SEQ ID NO: 64, and inhibiting the enzymatic activity of vascular endothelial lipase.

27) A monoclonal antibody or a fragment thereof, having a heavy chain variable region including three CDRs, said three CDRs consisting of amino acids that are one or several amino acids are deleted, substituted or added in at least one of the three CDRs, said the three CDRs comprising amino acid sequence of SEQ ID NO: 58, amino acid sequence of SEQ ID NO: 59 and amino acid sequence of SEQ ID NO: 60, and a light chain variable region including three CDRs comprising amino acid sequence of SEQ ID NO: 62, amino acid sequence of SEQ ID NO: 63 and amino acid sequence of SEQ ID NO: 64, and inhibiting the enzymatic activity of vascular endothelial lipase.

28) A monoclonal antibody or a fragment thereof, having a heavy chain variable region including three CDRs, said three CDRs consisting of amino acids that are one or several amino acids are deleted, substituted or added in at least one of the three CDRs, said the three CDRs comprising amino acid sequence of SEQ ID NO: 58, amino acid sequence of SEQ ID NO: 59 and amino acid sequence of SEQ ID NO: 60, and a light chain variable region including three CDRs, said three CDRs consisting of amino acids that are one or several amino acids are deleted, substituted or added in at least one of the three CDRs, said three CDRs comprising amino acid sequence of SEQ ID NO: 62, amino acid sequence of SEQ ID NO: 63 and amino acid sequence of SEQ ID NO: 64, and inhibiting the enzymatic activity of vascular endothelial lipase.

29) A monoclonal antibody or a fragment thereof, having a heavy chain variable region including three CDRs comprising amino acid sequence of SEQ ID NO: 66, amino acid sequence of SEQ ID NO: 67 and amino acid sequence of SEQ ID NO: 68 and a light chain variable region including three CDRs comprising amino acid sequence of SEQ ID NO: 70, amino acid sequence of SEQ ID NO: 71 and amino acid sequence of SEQ ID NO: 72.

30) A monoclonal antibody or a fragment thereof, having a heavy chain variable region including three CDRs comprising amino acid sequence of SEQ ID NO: 66, amino acid sequence of SEQ ID NO: 67 and amino acid sequence of SEQ ID NO: 68 and a light chain variable region including three CDRs, said three CDRs consisting of amino acids that are one or several amino acids are deleted, substituted or added in at least one of the three CDRs, said the three CDRs comprising amino acid sequence of SEQ ID NO: 70, amino acid sequence of SEQ ID NO: 71 and amino acid sequence of SEQ ID NO: 72, and inhibiting the enzymatic activity of vascular endothelial lipase.

31) A monoclonal antibody or a fragment thereof, having a heavy chain variable region including three CDRs, said three CDRs consisting of amino acids that are one or several amino acids are deleted, substituted or added in at least one of the three CDRs, said the three CDRs comprising amino acid sequence of SEQ ID NO: 66, amino acid sequence of SEQ ID NO: 67 and amino acid sequence of SEQ ID NO: 68, and a light chain variable region including three CDRs comprising amino acid sequence of SEQ ID NO: 70, amino acid sequence of SEQ ID NO: 71 and amino acid sequence of SEQ ID NO: 72, and inhibiting the enzymatic activity of vascular endothelial lipase.

32) A monoclonal antibody or a fragment thereof, having a heavy chain variable region including three CDRs, said three CDRs consisting of amino acids that are one or several amino acids are deleted, substituted or added in at least one of the three CDRs, said the three CDRs comprising amino acid sequence of SEQ ID NO: 66, amino acid sequence of SEQ ID NO: 67 and amino acid sequence of SEQ ID NO: 68, and a light chain variable region including three CDRs, said three CDRs consisting of amino acids that are one or several amino acids are deleted, substituted or added in at least one of the three CDRs, said three CDRs comprising amino acid sequence of SEQ ID NO: 70, amino acid sequence of SEQ ID NO: 71 and amino acid sequence of SEQ ID NO: 72, and inhibiting the enzymatic activity of vascular endothelial lipase.

33) A monoclonal antibody or a fragment thereof, having a heavy chain variable region including three CDRs comprising amino acid sequence of SEQ ID NO: 74, amino acid sequence of SEQ ID NO: 75 and amino acid sequence of SEQ ID NO: 76 and a light chain variable region including three CDRs comprising amino acid sequence of SEQ ID NO: 78, amino acid sequence of SEQ ID NO: 79 and amino acid sequence of SEQ ID NO: 80.

34) A monoclonal antibody or a fragment thereof, having a heavy chain variable region including three CDRs comprising amino acid sequence of SEQ ID NO: 74, amino acid sequence of SEQ ID NO: 75 and amino acid sequence of SEQ ID NO: 76 and a light chain variable region including three CDRs, said three CDRs consisting of amino acids that are one or several amino acids are deleted, substituted or added in at least one of the three CDRs, said the three CDRs comprising amino acid sequence of SEQ ID NO: 78, amino acid sequence of SEQ ID NO: 79 and amino acid sequence of SEQ ID NO: 80, and inhibiting the enzymatic activity of vascular endothelial lipase.

35) A monoclonal antibody or a fragment thereof, having a heavy chain variable region including three CDRs, said three CDRs consisting of amino acids that are one or several amino acids are deleted, substituted or added in at least one of the three CDRs, said the three CDRs comprising amino acid sequence of SEQ ID NO: 74, amino acid sequence of SEQ ID NO: 75 and amino acid sequence of SEQ ID NO: 76, and a light chain variable region including three CDRs comprising amino acid sequence of SEQ ID NO: 78, amino acid sequence of SEQ ID NO: 79 and amino acid sequence of SEQ ID NO: 80, and inhibiting the enzymatic activity of vascular endothelial lipase.

36) A monoclonal antibody or a fragment thereof, having a heavy chain variable region including three CDRs, said three CDRs consisting of amino acids that are one or several amino acids are deleted, substituted or added in at least one of the three CDRs, said the three CDRs comprising amino acid sequence of SEQ ID NO: 74, amino acid sequence of SEQ ID NO: 75 and amino acid sequence of SEQ ID NO: 76, and a light chain variable region including three CDRs, said three CDRs consisting of amino acids that are one or several amino acids are deleted, substituted or added in at least one of the three CDRs, said three CDRs comprising amino acid sequence of SEQ ID NO: 78, amino acid sequence of SEQ ID NO: 79 and amino acid sequence of SEQ ID NO: 80, and inhibiting the enzymatic activity of vascular endothelial lipase.

37) A monoclonal antibody or a fragment thereof, having a heavy chain variable region including three CDRs comprising amino acid sequence of SEQ ID NO: 82, amino acid sequence of SEQ ID NO: 83 and amino acid sequence of SEQ ID NO: 84 and a light chain variable region including three CDRs comprising amino acid sequence of SEQ ID NO: 86, amino acid sequence of SEQ ID NO: 87 and amino acid sequence of SEQ ID NO: 88.

38) A monoclonal antibody or a fragment thereof, having a heavy chain variable region including three CDRs comprising amino acid sequence of SEQ ID NO: 82, amino acid sequence of SEQ ID NO: 83 and amino acid sequence of SEQ ID NO: 84 and a light chain variable region including three CDRs, said three CDRs consisting of amino acids that are one or several amino acids are deleted, substituted or added in at least one of the three CDRs, said the three CDRs comprising amino acid sequence of SEQ ID NO: 86, amino acid sequence of SEQ ID NO: 87 and amino acid sequence of SEQ ID NO: 88, and inhibiting the enzymatic activity of vascular endothelial lipase.

39) A monoclonal antibody or a fragment thereof, having a heavy chain variable region including three CDRs, said three CDRs consisting of amino acids that are one or several amino acids are deleted, substituted or added in at least one of the three CDRs, said the three CDRs comprising amino acid sequence of SEQ ID NO: 82, amino acid sequence of SEQ ID NO: 83 and amino acid sequence of SEQ ID NO: 84, and a light chain variable region including three CDRs comprising amino acid sequence of SEQ ID NO: 86, amino acid sequence of SEQ ID NO: 87 and amino acid sequence of SEQ ID NO: 88, and inhibiting the enzymatic activity of vascular endothelial lipase.

40) A monoclonal antibody or a fragment thereof, having a heavy chain variable region including three CDRs, said three CDRs consisting of amino acids that are one or several amino acids are deleted, substituted or added in at least one of the three CDRs, said the three CDRs comprising amino acid sequence of SEQ ID NO: 82, amino acid sequence of SEQ ID NO: 83 and amino acid sequence of SEQ ID NO: 84, and a light chain variable region including three CDRs, said three CDRs consisting of amino acids that are one or several amino acids are deleted, substituted or added in at least one of the three CDRs, said three CDRs comprising amino acid sequence of SEQ ID NO: 86, amino acid sequence of SEQ ID NO: 87 and amino acid sequence of SEQ ID NO: 88, and inhibiting the enzymatic activity of vascular endothelial lipase.

41) A monoclonal antibody or a fragment thereof, having a heavy chain variable region including three CDRs comprising amino acid sequence of SEQ ID NO: 90, amino acid sequence of SEQ ID NO: 91 and amino acid sequence of SEQ ID NO: 92 and a light chain variable region including three CDRs comprising amino acid sequence of SEQ ID NO: 94, amino acid sequence of SEQ ID NO: 95 and amino acid sequence of SEQ ID NO: 96.

42) A monoclonal antibody or a fragment thereof, having a heavy chain variable region including three CDRs comprising amino acid sequence of SEQ ID NO: 90, amino acid sequence of SEQ ID NO: 91 and amino acid sequence of SEQ ID NO: 92 and a light chain variable region including three CDRs, said three CDRs consisting of amino acids that are one or several amino acids are deleted, substituted or added in at least one of the three CDRs, said the three CDRs comprising amino acid sequence of SEQ ID NO: 94, amino acid sequence of SEQ ID NO: 95 and amino acid sequence of SEQ ID NO: 96, and inhibiting the enzymatic activity of vascular endothelial lipase.

43) A monoclonal antibody or a fragment thereof, having a heavy chain variable region including three CDRs, said three CDRs consisting of amino acids that are one or several amino acids are deleted, substituted or added in at least one of the three CDRs, said the three CDRs comprising amino acid sequence of SEQ ID NO: 90, amino acid sequence of SEQ ID NO: 91 and amino acid sequence of SEQ ID NO: 92, and a light chain variable region including three CDRs comprising amino acid sequence of SEQ ID NO: 94, amino acid sequence of SEQ ID NO: 95 and amino acid sequence of SEQ ID NO: 96, and inhibiting the enzymatic activity of vascular endothelial lipase.

44) A monoclonal antibody or a fragment thereof, having a heavy chain variable region including three CDRs, said three CDRs consisting of amino acids that are one or several amino acids are deleted, substituted or added in at least one of the three CDRs, said the three CDRs comprising amino acid sequence of SEQ ID NO: 90, amino acid sequence of SEQ ID NO: 91 and amino acid sequence of SEQ ID NO: 92, and a light chain variable region including three CDRs, said three CDRs consisting of amino acids that are one or several amino acids are deleted, substituted or added in at least one of the three CDRs, said three CDRs comprising amino acid sequence of SEQ ID NO: 94, amino acid sequence of SEQ ID NO: 95 and amino acid sequence of SEQ ID NO: 96, and inhibiting the enzymatic activity of vascular endothelial lipase.

45) A monoclonal antibody or a fragment thereof, having a heavy chain variable region including three CDRs comprising amino acid sequence of SEQ ID NO: 100, amino acid sequence of SEQ ID NO: 101 and amino acid sequence of SEQ ID NO: 102 and a light chain variable region including three CDRs comprising amino acid sequence of SEQ ID NO: 104, amino acid sequence of SEQ ID NO: 105 and amino acid sequence of SEQ ID NO: 106.

46) A monoclonal antibody or a fragment thereof, having a heavy chain variable region including three CDRs comprising amino acid sequence of SEQ ID NO: 100, amino acid sequence of SEQ ID NO: 101 and amino acid sequence of SEQ ID NO: 102 and a light chain variable region including three CDRs, said three CDRs consisting of amino acids that are one or several amino acids are deleted, substituted or added in at least one of the three CDRs, said the three CDRs comprising amino acid sequence of SEQ ID NO: 104, amino acid sequence of SEQ ID NO: 105 and amino acid sequence of SEQ ID NO: 106, and inhibiting the enzymatic activity of vascular endothelial lipase.

47) A monoclonal antibody or a fragment thereof, having a heavy chain variable region including three CDRs, said three CDRs consisting of amino acids that are one or several amino acids are deleted, substituted or added in at least one of the three CDRs, said the three CDRs comprising amino acid sequence of SEQ ID NO: 100, amino acid sequence of SEQ ID NO: 101 and amino acid sequence of SEQ ID NO: 102, and a light chain variable region including three CDRs comprising amino acid sequence of SEQ ID NO: 104, amino acid sequence of SEQ ID NO: 105 and amino acid sequence of SEQ ID NO: 106, and inhibiting the enzymatic activity of vascular endothelial lipase.

48) A monoclonal antibody or a fragment thereof, having a heavy chain variable region including three CDRs, said three CDRs consisting of amino acids that are one or several amino acids are deleted, substituted or added in at least one of the three CDRs, said the three CDRs comprising amino acid sequence of SEQ ID NO: 100, amino acid sequence of SEQ ID NO: 101 and amino acid sequence of SEQ ID NO: 102, and a light chain variable region including three CDRs, said three CDRs consisting of amino acids that are one or several amino acids are deleted, substituted or added in at least one of the three CDRs, said three CDRs comprising amino acid sequence of SEQ ID NO: 104, amino acid sequence of SEQ ID NO: 105 and amino acid sequence of SEQ ID NO: 106, and inhibiting the enzymatic activity of vascular endothelial lipase.

(15) A monoclonal antibody or a fragment thereof, selected from the group of

1) A monoclonal antibody or a fragment thereof, having a heavy chain variable region comprising amino acid sequence of SEQ ID NO: 9, and a light chain variable region comprising amino acid sequence of SEQ ID NO: 13.

2) A monoclonal antibody or a fragment thereof, having a heavy chain variable region comprising amino acid sequence of SEQ ID NO: 9, and a light chain variable region comprising amino acids, said amino acids that are one or several amino acids are deleted, substituted or added in amino acids sequence of SEQ ID NO: 13, and inhibiting the enzymatic activity of vascular endothelial lipase.

3) A monoclonal antibody or a fragment thereof, having a heavy chain variable region comprising amino acids, said amino acids that are one or several amino acids are deleted, substituted or added in amino acids sequence of SEQ ID NO: 9 and a light chain variable region comprising amino acid sequence of SEQ ID NO: 13 and inhibiting the enzymatic activity of vascular endothelial lipase.

4) A monoclonal antibody or a fragment thereof, having a heavy chain variable region comprising amino acids, said amino acids that are one or several amino acids are deleted, substituted or added in amino acids sequence of SEQ ID NO: 9 and a light chain variable region comprising amino acids, said amino acids that are one or several amino acids are deleted, substituted or added in amino acids sequence of SEQ ID NO: 13, and inhibiting the enzymatic activity of vascular endothelial lipase.

5) A monoclonal antibody or a fragment thereof, having a heavy chain variable region comprising amino acid sequence of SEQ ID NO: 17, and a light chain variable region comprising amino acid sequence of SEQ ID NO: 21.

6) A monoclonal antibody or a fragment thereof, having a heavy chain variable region comprising amino acid sequence of SEQ ID NO: 17, and a light chain variable region comprising amino acids, said amino acids that are one or several amino acids are deleted, substituted or added in amino acids sequence of SEQ ID NO: 21, and inhibiting the enzymatic activity of vascular endothelial lipase.

7) A monoclonal antibody or a fragment thereof, having a heavy chain variable region comprising amino acids, said amino acids that are one or several amino acids are deleted, substituted or added in amino acids sequence of SEQ ID NO: 17 and a light chain variable region comprising amino acid sequence of SEQ ID NO: 21 and inhibiting the enzymatic activity of vascular endothelial lipase.

8) A monoclonal antibody or a fragment thereof, having
   a heavy chain variable region comprising amino acids, said amino acids that are one or several amino acids are deleted, substituted or added in amino acids sequence of SEQ ID NO: 17 and
   a light chain variable region comprising amino acids, said amino acids that are one or several amino acids are deleted, substituted or added in amino acids sequence of SEQ ID NO: 21, and
inhibiting the enzymatic activity of vascular endothelial lipase.

9) A monoclonal antibody or a fragment thereof, having
   a heavy chain variable region comprising amino acid sequence of SEQ ID NO: 25, and
   a light chain variable region comprising amino acid sequence of SEQ ID NO: 29.

10) A monoclonal antibody or a fragment thereof, having
   a heavy chain variable region comprising amino acid sequence of SEQ ID NO: 25, and
   a light chain variable region comprising amino acids, said amino acids that are one or several amino acids are deleted, substituted or added in amino acids sequence of SEQ ID NO: 29, and
inhibiting the enzymatic activity of vascular endothelial lipase.

11) A monoclonal antibody or a fragment thereof, having
   a heavy chain variable region comprising amino acids, said amino acids that are one or several amino acids are deleted, substituted or added in amino acids sequence of SEQ ID NO: 25 and
   a light chain variable region comprising amino acid sequence of SEQ ID NO: 29 and inhibiting the enzymatic activity of vascular endothelial lipase.

12) A monoclonal antibody or a fragment thereof, having
   a heavy chain variable region comprising amino acids, said amino acids that are one or several amino acids are deleted, substituted or added in amino acids sequence of SEQ ID NO: 25 and
   a light chain variable region comprising amino acids, said amino acids that are one or several amino acids are deleted, substituted or added in amino acids sequence of SEQ ID NO: 29, and
inhibiting the enzymatic activity of vascular endothelial lipase.

13) A monoclonal antibody or a fragment thereof, having
   a heavy chain variable region comprising amino acid sequence of SEQ ID NO: 33, and
   a light chain variable region comprising amino acid sequence of SEQ ID NO: 37.

14) A monoclonal antibody or a fragment thereof, having
   a heavy chain variable region comprising amino acid sequence of SEQ ID NO: 33, and
   a light chain variable region comprising amino acids, said amino acids that are one or several amino acids are deleted, substituted or added in amino acids sequence of SEQ ID NO: 37, and
inhibiting the enzymatic activity of vascular endothelial lipase.

15) A monoclonal antibody or a fragment thereof, having
   a heavy chain variable region comprising amino acids, said amino acids that are one or several amino acids are deleted, substituted or added in amino acids sequence of SEQ ID NO: 33 and
   a light chain variable region comprising amino acid sequence of SEQ ID NO: 37 and
inhibiting the enzymatic activity of vascular endothelial lipase.

16) A monoclonal antibody or a fragment thereof, having
   a heavy chain variable region comprising amino acids, said amino acids that are one or several amino acids are deleted, substituted or added in amino acids sequence of SEQ ID NO: 33 and
   a light chain variable region comprising amino acids, said amino acids that are one or several amino acids are deleted, substituted or added in amino acids sequence of SEQ ID NO: 37, and
inhibiting the enzymatic activity of vascular endothelial lipase.

17) A monoclonal antibody or a fragment thereof, having
   a heavy chain variable region comprising amino acid sequence of SEQ ID NO: 41, and
   a light chain variable region comprising amino acid sequence of SEQ ID NO: 45.

18) A monoclonal antibody or a fragment thereof, having
   a heavy chain variable region comprising amino acid sequence of SEQ ID NO: 41, and
   a light chain variable region comprising amino acids, said amino acids that are one or several amino acids are deleted, substituted or added in amino acids sequence of SEQ ID NO: 45, and
inhibiting the enzymatic activity of vascular endothelial lipase.

19) A monoclonal antibody or a fragment thereof, having
   a heavy chain variable region comprising amino acids, said amino acids that are one or several amino acids are deleted, substituted or added in amino acids sequence of SEQ ID NO: 41 and
   a light chain variable region comprising amino acid sequence of SEQ ID NO: 45 and inhibiting the enzymatic activity of vascular endothelial lipase.

20) A monoclonal antibody or a fragment thereof, having
   a heavy chain variable region comprising amino acids, said amino acids that are one or several amino acids are deleted, substituted or added in amino acids sequence of SEQ ID NO: 41 and
   a light chain variable region comprising amino acids, said amino acids that are one or several amino acids are deleted, substituted or added in amino acids sequence of SEQ ID NO: 45, and
inhibiting the enzymatic activity of vascular endothelial lipase.

21) A monoclonal antibody or a fragment thereof, having
   a heavy chain variable region comprising amino acid sequence of SEQ ID NO: 49, and
   a light chain variable region comprising amino acid sequence of SEQ ID NO: 53.

22) A monoclonal antibody or a fragment thereof, having
   a heavy chain variable region comprising amino acid sequence of SEQ ID NO: 49, and
   a light chain variable region comprising amino acids, said amino acids that are one or several amino acids are deleted, substituted or added in amino acids sequence of SEQ ID NO: 53, and
inhibiting the enzymatic activity of vascular endothelial lipase.

23) A monoclonal antibody or a fragment thereof, having
   a heavy chain variable region comprising amino acids, said amino acids that are one or several amino acids are deleted, substituted or added in amino acids sequence of SEQ ID NO: 49 and
   a light chain variable region comprising amino acid sequence of SEQ ID NO: 5 and inhibiting the enzymatic activity of vascular endothelial lipase.

24) A monoclonal antibody or a fragment thereof, having
   a heavy chain variable region comprising amino acids, said amino acids that are one or several amino acids are deleted, substituted or added in amino acids sequence of SEQ ID NO: 49 and
   a light chain variable region comprising amino acids, said amino acids that are one or several amino acids are deleted, substituted or added in amino acids sequence of SEQ ID NO: 53, and
inhibiting the enzymatic activity of vascular endothelial lipase.

25) A monoclonal antibody or a fragment thereof, having
   a heavy chain variable region comprising amino acid sequence of SEQ ID NO: 57, and
   a light chain variable region comprising amino acid sequence of SEQ ID NO: 61.

26) A monoclonal antibody or a fragment thereof, having
   a heavy chain variable region comprising amino acid sequence of SEQ ID NO: 57, and
   a light chain variable region comprising amino acids, said amino acids that are one or several amino acids are deleted, substituted or added in amino acids sequence of SEQ ID NO: 61, and
inhibiting the enzymatic activity of vascular endothelial lipase.

27) A monoclonal antibody or a fragment thereof, having
   a heavy chain variable region comprising amino acids, said amino acids that are one or several amino acids are deleted, substituted or added in amino acids sequence of SEQ ID NO: 57 and
   a light chain variable region comprising amino acid sequence of SEQ ID NO: 61 and inhibiting the enzymatic activity of vascular endothelial lipase.

28) A monoclonal antibody or a fragment thereof, having
   a heavy chain variable region comprising amino acids, said amino acids that are one or several amino acids are deleted, substituted or added in amino acids sequence of SEQ ID NO: 57 and
   a light chain variable region comprising amino acids, said amino acids that are one or several amino acids are deleted, substituted or added in amino acids sequence of SEQ ID NO: 61, and
inhibiting the enzymatic activity of vascular endothelial lipase.

29) A monoclonal antibody or a fragment thereof, having
   a heavy chain variable region comprising amino acid sequence of SEQ ID NO: 65, and
   a light chain variable region comprising amino acid sequence of SEQ ID NO: 69.

30) A monoclonal antibody or a fragment thereof, having
   a heavy chain variable region comprising amino acid sequence of SEQ ID NO: 65, and
   a light chain variable region comprising amino acids, said amino acids that are one or several amino acids are deleted, substituted or added in amino acids sequence of SEQ ID NO: 69, and
inhibiting the enzymatic activity of vascular endothelial lipase.

31) A monoclonal antibody or a fragment thereof, having
   a heavy chain variable region comprising amino acids, said amino acids that are one or several amino acids are deleted, substituted or added in amino acids sequence of SEQ ID NO: 65 and
   a light chain variable region comprising amino acid sequence of SEQ ID NO: 69 and inhibiting the enzymatic activity of vascular endothelial lipase.

32) A monoclonal antibody or a fragment thereof, having
   a heavy chain variable region comprising amino acids, said amino acids that are one or several amino acids are deleted, substituted or added in amino acids sequence of SEQ ID NO: 65 and
   a light chain variable region comprising amino acids, said amino acids that are one or several amino acids are deleted, substituted or added in amino acids sequence of SEQ ID NO: 69, and
inhibiting the enzymatic activity of vascular endothelial lipase.

33) A monoclonal antibody or a fragment thereof, having
   a heavy chain variable region comprising amino acid sequence of SEQ ID NO: 73, and
   a light chain variable region comprising amino acid sequence of SEQ ID NO: 77.

34) A monoclonal antibody or a fragment thereof, having
   a heavy chain variable region comprising amino acid sequence of SEQ ID NO: 73, and
   a light chain variable region comprising amino acids, said amino acids that are one or several amino acids are deleted, substituted or added in amino acids sequence of SEQ ID NO: 77, and
inhibiting the enzymatic activity of vascular endothelial lipase.

35) A monoclonal antibody or a fragment thereof, having
   a heavy chain variable region comprising amino acids, said amino acids that are one or several amino acids are deleted, substituted or added in amino acids sequence of SEQ ID NO: 73 and
   a light chain variable region comprising amino acid sequence of SEQ ID NO: 77 and inhibiting the enzymatic activity of vascular endothelial lipase.

36) A monoclonal antibody or a fragment thereof, having
- a heavy chain variable region comprising amino acids, said amino acids that are one or several amino acids are deleted, substituted or added in amino acids sequence of SEQ ID NO: 73 and
- a light chain variable region comprising amino acids, said amino acids that are one or several amino acids are deleted, substituted or added in amino acids sequence of SEQ ID NO: 77, and inhibiting the enzymatic activity of vascular endothelial lipase.

37) A monoclonal antibody or a fragment thereof, having
- a heavy chain variable region comprising amino acid sequence of SEQ ID NO: 81, and
- a light chain variable region comprising amino acid sequence of SEQ ID NO: 85.

38) A monoclonal antibody or a fragment thereof, having
- a heavy chain variable region comprising amino acid sequence of SEQ ID NO: 81, and
- a light chain variable region comprising amino acids, said amino acids that are one or several amino acids are deleted, substituted or added in amino acids sequence of SEQ ID NO: 85, and inhibiting the enzymatic activity of vascular endothelial lipase.

39) A monoclonal antibody or a fragment thereof, having
- a heavy chain variable region comprising amino acids, said amino acids that are one or several amino acids are deleted, substituted or added in amino acids sequence of SEQ ID NO: 81 and
- a light chain variable region comprising amino acid sequence of SEQ ID NO: 85 and inhibiting the enzymatic activity of vascular endothelial lipase.

40) A monoclonal antibody or a fragment thereof, having
- a heavy chain variable region comprising amino acids, said amino acids that are one or several amino acids are deleted, substituted or added in amino acids sequence of SEQ ID NO: 81 and
- a light chain variable region comprising amino acids, said amino acids that are one or several amino acids are deleted, substituted or added in amino acids sequence of SEQ ID NO: 85, and inhibiting the enzymatic activity of vascular endothelial lipase.

41) A monoclonal antibody or a fragment thereof, having
- a heavy chain variable region comprising amino acid sequence of SEQ ID NO: 89, and
- a light chain variable region comprising amino acid sequence of SEQ ID NO: 93.

42) A monoclonal antibody or a fragment thereof, having
- a heavy chain variable region comprising amino acid sequence of SEQ ID NO: 89, and
- a light chain variable region comprising amino acids, said amino acids that are one or several amino acids are deleted, substituted or added in amino acids sequence of SEQ ID NO: 93, and inhibiting the enzymatic activity of vascular endothelial lipase.

43) A monoclonal antibody or a fragment thereof, having
- a heavy chain variable region comprising amino acids, said amino acids that are one or several amino acids are deleted, substituted or added in amino acids sequence of SEQ ID NO: 89 and
- a light chain variable region comprising amino acid sequence of SEQ ID NO: 93 and inhibiting the enzymatic activity of vascular endothelial lipase.

44) A monoclonal antibody or a fragment thereof, having
- a heavy chain variable region comprising amino acids, said amino acids that are one or several amino acids are deleted, substituted or added in amino acids sequence of SEQ ID NO: 89 and
- a light chain variable region comprising amino acids, said amino acids that are one or several amino acids are deleted, substituted or added in amino acids sequence of SEQ ID NO: 93, and inhibiting the enzymatic activity of vascular endothelial lipase.

45) A monoclonal antibody or a fragment thereof, having
- a heavy chain variable region comprising amino acid sequence of SEQ ID NO: 99, and
- a light chain variable region comprising amino acid sequence of SEQ ID NO: 103.

46) A monoclonal antibody or a fragment thereof, having
- a heavy chain variable region comprising amino acid sequence of SEQ ID NO: 99, and
- a light chain variable region comprising amino acids, said amino acids that are one or several amino acids are deleted, substituted or added in amino acids sequence of SEQ ID NO: 103, and inhibiting the enzymatic activity of vascular endothelial lipase.

47) A monoclonal antibody or a fragment thereof, having
- a heavy chain variable region comprising amino acids, said amino acids that are one or several amino acids are deleted, substituted or added in amino acids sequence of SEQ ID NO: 99 and
- a light chain variable region comprising amino acid sequence of SEQ ID NO: 103 and inhibiting the enzymatic activity of vascular endothelial lipase.

48) A monoclonal antibody or a fragment thereof, having
- a heavy chain variable region comprising amino acids, said amino acids that are one or several amino acids are deleted, substituted or added in amino acids sequence of SEQ ID NO: 99 and
- a light chain variable region comprising amino acids, said amino acids that are one or several amino acids are deleted, substituted or added in amino acids sequence of SEQ ID NO: 103, and inhibiting the enzymatic activity of vascular endothelial lipase.

(16) The pharmaceutical composition for treating or preventing a disease related to vascular endothelial lipase, comprising the monoclonal antibody of any one of (1) to (15) or the antibody fragment thereof.

(17) The pharmaceutical composition of according to (16), wherein the disease related to vascular endothelial lipase is Dyslipidemia.

(18) The monoclonal antibody of any one of (1) to (15) or the antibody fragment thereof for the treatment or prevention of a disease related to vascular endothelial lipase.

(19) The monoclonal antibody of (18) or the antibody fragment thereof, wherein the disease related to vascular endothelial lipase is Dyslipidemia.

(20) A method for the treatment or prevention of a disease related to vascular endothelial lipase characterized by administering to a monoclonal antibody of any one of (1) to (15) or the antibody fragment thereof.

(21) The method of (20), wherein the disease related to vascular endothelial lipase is Dyslipidemia.

Effect of the Invention

As a monoclonal antibody of the present invention has the activity for selectively inhibiting enzymatic activity of EL, pharmaceutical compositions containing the monoclonal antibody of the present invention is very useful as a drug, especially a drug for prevention and/or treatment of dyslipidemia, hyperlipidemia, arteriosclerosis, atherosclerosis, hypercholesterolemia, hypertriglyceridemia, diabetes, obesity and/or syndrome X.

BRIEF EXPLANATION OF DRAWINGS

FIG. 3K shows measurement results of inhibiting enzymatic activity of 19E7 antibody against cynomolgus EL, baboon EL, rabbit EL, human (1-157) mouse chimera EL and human (1-305) mouse chimera EL.

FIG. 3L shows measurement results of inhibiting enzymatic activity of 16F6 antibody against cynomolgus EL, human (1-305) mouse chimera EL and human (187-500) mouse chimera EL.

FIG. 4A (SEQ ID NOS: 9 and 13) shows amino acid sequence of a variable region of 55A1 antibody.

FIG. 4B (SEQ ID NOS: 17 and 21) shows amino acid sequence of a variable region of 7D4 antibody.

FIG. 4C (SEQ ID NOS: 25 and 29) shows amino acid sequence of a variable region of 14A1 antibody.

FIG. 4D (SEQ ID NOS: 33 and 37) shows amino acid sequence of a variable region of 2D5 antibody.

FIG. 4E (SEQ ID NOS: 41 and 45) shows amino acid sequence of a variable region of 53A11 antibody.

FIG. 4F (SEQ ID NOS: 49 and 53) shows amino acid sequence of a variable region of 13B3 antibody.

FIG. 4G (SEQ ID NOS: 57 and 61) shows amino acid sequence of a variable region of 23H8 antibody.

FIG. 4H (SEQ ID NOS: 65 and 69) shows amino acid sequence of a variable region of 16B3 antibody.

FIG. 4I (SEQ ID NOS: 73 and 77) shows amino acid sequence of a variable region of 16E7 antibody.

FIG. 4J (SEQ ID NOS: 81 and 85) shows amino acid sequence of a variable region of 14E1 antibody.

FIG. 4K (SEQ ID NOS: 89 and 93) shows amino acid sequence of a variable region of 19E7 antibody.

FIG. 4L (SEQ ID NOS: 99 and 103) shows amino acid sequence of a variable region of 16F6 antibody.

FIG. 5A shows an alignment of the amino acid sequences of heavy chain variable region of 55A1 antibody (SEQ ID NO: 9), 7D4 antibody (SEQ ID NO: 17), 14A1 antibody (SEQ ID NO: 25) and 2D5 antibody (SEQ ID NO: 33).

FIG. 5B shows an alignment of the amino acid sequences of light chain variable region of 55A1 antibody (SEQ ID NO: 13), 7D4 antibody (SEQ ID NO: 21), 14A1 antibody (SEQ ID NO: 29) and 2D5 antibody (SEQ ID NO: 37).

FIG. 5C shows an alignment of the amino acid sequences of heavy chain variable region of 53A11 antibody (SEQ ID NO: 41), 13B3 antibody (SEQ ID NO: 49) and 23H8 antibody (SEQ ID NO: 57).

FIG. 5D shows an alignment of the amino acid sequences of light chain variable region of 53A11 antibody (SEQ ID NO: 45), 13B3 antibody (SEQ ID NO: 53) and 23H8 antibody (SEQ ID NO: 61).

FIG. 6A shows an alignment of the amino acid sequences of heavy chain variable region of 16B3 antibody (SEQ ID NO: 65) and 16E7 antibody (SEQ ID NO:73).

FIG. 6B shows an alignment of the amino acid sequences of light chain variable region of 16B3 (SEQ ID NO: 60) antibody and 16E7 antibody (SEQ ID NO: 77).

FIG. 6C shows an alignment of the amino acid sequences of heavy chain variable region of 14E1 antibody (SEQ ID NO: 81) and 19E7 antibody (SEQ ID NO: 89).

FIG. 6D shows an alignment of the amino acid sequences of light chain variable region of 14E1 antibody (SEQ ID NO: 85) and 19E7 antibody (SEQ ID NO: 93).

MODE FOR CARRYING OUT THE INVENTION

Figure 1A:
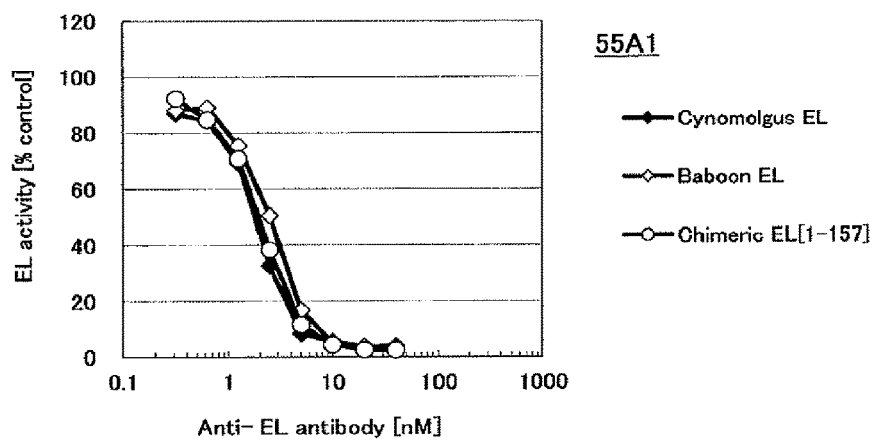
FIG. 1A shows measurement results of inhibition of enzymatic activity of 55A1 antibody against cynomolgus EL, baboon EL and human (1-157) mouse chimera EL.

The present invention provides a monoclonal antibody characterized by selectively inhibiting the enzymatic activity of vascular endothelial lipase. As the monoclonal antibody of the present invention has the activity for selectively inhibiting enzymatic activity of vascular endothelial lipase, it is very useful as a drug for prevention or treatment of arteriosclerosis or metabolic syndrome.

It is important to use peptide having consecutive amino acid residues containing amino acid sequence at positions of 1 to 157 or 202 to 305 region in amino acid sequence of SEQ ID NO: 1 as antigen to produce a monoclonal antibody of the present invention. The length is not particularly limited, but six or more residues which have immunogenicity are desired. We can use naturally or artificially highly expressed cell lines, these membrane fractions, these purified products, fusion proteins with other proteins or peptides (for examples, tag proteins such as FLAG-tag, HIS-tag, GST-tag or C2tag etc. or fluorescent proteins such as GFP or EGFP etc.), or chemically synthesized peptides as specific examples of these antibodies. In addition, preparation methods of these immunogens are known to those skilled in the art.

The monoclonal antibody of the present invention may be prepared by an known commonly used production method. Concretely, a mammal, preferably, mouse, rat, hamster, guinea pig, rabbit, cat, dog, pig, goat, sheep, donkey, horse or bovine, more preferably mouse, rat, hamster, guinea pig or rabbit is immunized with an immunogen of the present invention, together with Freund's adjuvant as necessary, by one or several times of subcutaneous, intramuscular, intravenous, intrafootpad or intraperitoneal injection. Usually, immunization is conducted once to four times every about 1 to 21 days after primary immunization, and antibody producing cells may be acquired from the immunized mammal after about 1 to 10 days from the final immunization. The number of times and time interval of immunization may be appropriately changed depending on the property of the immunogen being used.

Hybridoma that secrets monoclonal antibody may be prepared according to the Kohler and Milstein's method (Nature, 1975, vol. 256, p. 495-497) and a corresponding method. That is, hybridoma may be prepared by cell fusion between an antibody producing cell contained in spleen, lymph node, bone marrow, tonsil or the like, preferably in spleen acquired from a mammal immunized as described above, and a myeloma cell lacking autoantibody producing ability derived, preferably from a mammal such as mouse, rat, guinea pig, hamster, rabbit or human, more preferably from mouse, rat or human.

As a myeloma cell used in cell fusion, generally, cell lines obtained from mouse, for example, P3-U1, NS-1, SP-2, 653, X63, AP-1 and the like may be used.

Hybridoma that produces monoclonal antibody is screened by culturing a hybridoma, for example, in a microtiter plate, measuring reactivity to an immunogen used in mouse immunization as described above in culture supernatant in the well where proliferation is observed, by a measuring method such as RIA, ELISA or FACS and selecting a clone that produces a monoclonal antibody exhibiting specific affinity with the immunogen or hapten. When measuring the said reactivity, an immunogen is usually solid-phased, and an antibody in culture supernatant that binds to the solid-phased immunogen is detected by an anti-mouse secondary antibody labeled with a radioactive substance, a fluorescent substance or an enzyme. Further in the case of using the cells expressing the immunogen, we add the hybridoma culture supernatant to the cells, then after reacting with secondary antibodies labeled with a fluorescent, we can detect a monoclonal antibody of the present invention that binds to the immunogen on the cell membrane by measuring fluorescence intensity of the cells with fluorescence detection apparatus such as flow cytometry or the like.

Production of monoclonal antibody from selected hybridoma may be achieved by culturing hybridoma in vitro or in ascites of mouse, rat, guinea pig, hamster or rabbit, preferably of mouse or rat, or more preferably of mouse, followed by isolation from the obtained culture supernatant or ascites of mammal. In the case of in vitro culture, the hybridoma may be cultured in a known nutrient medium or in any nutrient cultures derived and prepared from a known base medium used for proliferating, maintaining and storing hybridoma and for producing monoclonal antibody in culture supernatant, depending on various conditions such as property of cultured cell species, object of the test research and culturing method.

As a base medium, for example, low-calcium media such as Ham'F12 medium, MCDB153 medium or low-calcium MEM culture, and high-calcium media such as MCDB104 medium, MEM medium, D-MEM medium, RPMI1640 medium, AF104 medium, or RD medium can be recited, and such a base medium may contain, for example, serum, hormone, cytokine and/or various inorganic or organic substances depending on the object.

Isolation and purification of monoclonal antibody may be achieved by subjecting the culture supernatant or ascites as described above to saturated ammonium sulfate, ion exchange chromatography (e.g., DEAE or DE52), affinity column chromatography such as anti-immunoglobulin column or protein A column or the like.

As a monoclonal antibody of the present invention, a recombinant antibody that is produced using gene recombination technique in such a manner that an antibody gene is cloned from antibody producing cell, for example, hybridoma, and incorporated into an appropriate vector, and the vector is introduced into a host may be used (for example, Carl et al., THERAPEUTIC MONOCLONAL ANTIBODIES, published in 1990).

Concretely, from a hybridoma that produces an objective antibody, or from an immune cell that produces an antibody, for example, from a cell obtained by immortalizing sensitized lymphocyte or the like by cancer gene or the like, mRNA encoding a variable region (V region) of antibody is isolated. In isolation of mRNA, whole RNA is prepared by a known method, for example, by guanidine ultracentrifugation (Chirgwin, J. M. et al., Biochemistry (1979) 18, 5294-5299) or the like, and mRNA is prepared by using mRNA Purification Kit (available from Pharmacia) or the like.

From the obtained mRNA, cDNA of antibody V region is synthesized using a reverse transcriptase. Synthesis of cDNA may be conducted using AMV Reverse Transcriptase First-strand cDNA Synthesis Kit or the like. Further, for synthesis and amplification of cDNA, 5'-Ampli FINDER RACEKit (available from Clonetech) and 5'-RACE method using PCR (Frohman, M. A. et al, Proc. Natl. Acad. Sci. USA 1988, vol. 85, p. 8998) may be used. An objective DNA fragment is purified from the obtained PCR product, and connected with vector DNA. A recombinant vector is thus created and introduced into E. coli or the like, and a colony is selected and a desired recombinant vector is prepared. DNA base sequence of objective DNA is verified by a known method, for example, by deoxy method.

If DNA encoding V region of objective antibody is obtained, the DNA is connected with DNA encoding a desired antibody constant region (C region), and incorporated into an expression vector. Alternatively, DNA encoding V region of antibody may be incorporated into an expression vector containing DNA of antibody C region. For production of antibody used in the present invention, antibody gene is incorporated into an expression vector in such a manner that it is expressed under control of an expression control region, for example, enhancer/promoter. Next, a host cell can be transformed with this expression vector to cause expression of antibody.

For expression of antibody gene, heavy chain (H chain) or light chain (L chain) of antibody may be separately incorporated into expression vectors, or a host may be co-transformed with these expression vectors, or DNA encoding H chain and L chain may be incorporated into a single expression vector to transform a host with the resultant expression vector (see WO94/11523).

Preparation method of a monoclonal antibody of the present invention other than the above can be also used so called phage display technology. Concretely, for example antibody gene library prepared as a material human or animal (for example, rabbit, mouse, rat, hamster or the like) B lymphosate by known method or completely synthesized antibody gene library prepared from selected and modified human or animal germ line sequence is presented to the cell surface, on the ribosome or the like of bacteriophage, *Escherichia coli*, yeast, animal cells or the like. In this case, the forms of the antibody to be presented on the cell surface are listed IgG molecules, IgM molecules, Fab fragments, single chain Fv (scFv) fragments, etc.

We can obtain antibody genes by rearranging thus obtained monoclonal antibody fragment to the corresponding region of the IgG antibody gene by a known method. And we incorporate thus genes obtained in this manner into a suitable vector, introduce the vector into the host, we can prepare the antibody with recombinant DNA techniques (for examples, see Carl et. al. THERAPEUTIC MONOCLONAL ANTIBODIES, 1990 issue).

The monoclonal antibody of the present invention is characterized in being selective for the inhibition of the enzymatic activity of vascular endothelial lipase. Below, we show an example of a procedure for measuring ability of inhibiting the enzymatic activity of EL.

The DNA encoding EL is cloned into pcDNA3.1 expression vector (Invitrogen). The expression vector is transfected into HEK293F cells and culture at 37° C., 8% CO2 for 2 days. The cell cultures are centrifuged, the cells are collected, the cells are suspended with PBS containing 20 U/mL of Heparin. The cell suspension is incubated at 37° C. for 45 min. The supernatant obtained by removing cells with centrifugation is used as human EL enzyme solution to measure inhibitory activity.

After adding a monoclonal antibody to the solution containing 20 mM Tris-HCl Buffer (pH 7.5), 0.5% bovine serum albumin, 4 mM CaCl2, 150 mM NaCl and 2 mg/mL human HDL (Athens Research&Techonology), EL enzyme solution is added. After reaction at 37° C. for 2 hr, free fatty acid (NEFA) made from HDL by EL enzyme is determined using NEFA C-test Wako (Wakojyunyakukougyo), the NFFA amount is used as enzyme activity index. Enzyme activity in the case of adding no antibody was determined as control value and the specific activity is calculated against the control value at each concentration of the antibody. The concentration where 50% of the antibody is inhibited can be calculated from the inhibition curve.

Effective concentration (IC50) of antibody which shows 50% inhibition of EL enzyme activity is often used as an indicator of EL inhibitory activity.

In the present invention, a monoclonal antibody or a fragment thereof inhibiting the enzymatic activity of vascular endothelial lipase with an IC 50 of 10 nM or less means a monoclonal antibody or a fragment thereof showing IC 50 of 10 nM or less measured by method of said [0027]-[0029]. Any species EL may be used for the measurement if the EL is derived from a mammal. If a monoclonal antibody or a fragment thereof inhibits the enzymatic activity of EL of any kind of mammal species with an IC 50 of 10 nM or less, the monoclonal antibody or a fragment thereof is a monoclonal antibody or a fragment thereof showing IC 50 of 10 nM or less.

And the monoclonal antibody of the present invention is characterized in being selective for the inhibition of the enzymatic activity of EL. Below, we show an example of a confirmation procedure for measuring ability of selectively inhibiting the enzymatic activity of EL, in other words, not inhibiting the enzymatic activity of LPL or HL.

The DNA encoding HL is cloned into pcDNA3.1 expression vector (Invitrogen). The expression vector is transfected into HEK293F cells and culture at 37° C., 8% CO2 for 2 days. The cell cultures are centrifuged, the cells are collected, the cells are suspended with PBS containing 20 U/mL of Heparin. The cell suspension is incubated at 37° C. for 45 min. The supernatant obtained by removing cells with centrifugation is used as human HL enzyme solution. LPL enzyme solution is prepared by using the same procedures. After adding a monoclonal antibody to the solution containing 20 mM Tris-HCl Buffer (pH 7.5), 0.5% bovine serum albumin, 4 mM CaCl2, 150 mM NaCl and 0.5 mg/mL human VLDL (INTRACEL), HL or LPL enzyme solution is added. After reaction at 37° C. for 2 hr, free fatty acid (NEFA) made from VLDL by HL or LPL enzyme is determined using NEFA C-test Wako (Wakojyunyakukougyo), the NFFA amount is used as enzyme activity index. Enzyme activity in the case of adding no antibody was determined as control value and the specific activity is calculated against the control value at each concentration of antibody.

Being selective for the inhibition of the enzymatic activity of EL means inhibiting not more than 3% LPL or HL enzymatic activities, when the monoclonal antibody are added at a concentration equal to IC50 against EL. An epitope region of a monoclonal antibody of the present invention is preferably the region of EL that has not homology with LPL or HL because a monoclonal antibody of the present invention is characterized by not inhibiting enzyme activity of LPL and HL, and is characterized in being selective for the inhibition of enzyme activity of EL.

The monoclonal antibody of the present invention includes recombinant monoclonal antibodies that are artificially modified for the purpose of lowering heterologous antigenicity against human, for example, chimera monoclonal antibody, humanized monoclonal antibody and human monoclonal antibody.

The monoclonal antibody of the present invention may be a conjugate antibody bound to various molecules such as polyethylene glycol (PEG), radioactive material, toxin. These conjugate antibodies can be obtained by chemically modifying obtained antibodies. The techniques of modification of antibody are well known in this field. These conjugate antibodies are included in monoclonal antibodies of the present invention.

And the monoclonal antibody of the present invention may fuse to the other proteins at the N terminal or C terminal of the antibody (Clinical Cancer Research, 2004, 10, 1274-1281). Those skilled in the art may properly select fusion protein.

In the present invention, "a monoclonal antibody fragment" means a part of the above-mentioned monoclonal antibody of the present invention and has the specific binding ability to vascular endothelial lipase as with the monoclonal antibody, or means a fragment that has the specific binding ability to vascular endothelial lipase as with the monoclonal antibody and has the effect of the inhibiting enzymatic activity of vascular endothelial lipase as with the monoclonal antibody. Concretely, fragments that have specific associativity against EL are listed Fab, $F(ab')_2$, Fab', single chain antibody (scFv), disulfide stabilized antibody (dsFv), dimerized V region fragment (Diabody), peptide containing CDR, etc. (Expert opinion on therapeutic patents, vol. 6, No. 5, p. 441-456, 1996).

A monoclonal antibody of the present invention or a fragment thereof is useful as a pharmaceutical composition. Therefore, a pharmaceutical composition containing a monoclonal antibody of the present invention or a fragment thereof may be administered systemically or topically by oral or parenteral route. For parenteral administration, for example, intravenous injection such as drip infusion, intramuscular injection, intraperitoneal injection, subcutaneous injection, intranasal administration, inhalation and the like can be selected.

Also, a monoclonal antibody of the present invention is applicable to the diagnostic for dyslipidemia, hyperlipidemia, arteriosclerosis, atherosclerosis, hypercholesterolemia, hypertriglyceridemia, diabetes, obesity and/or syndrome X because a monoclonal antibody of the invention has the specific binding ability to against vascular endothelial lipase.

A monoclonal antibody of the present invention or a fragment thereof is characterized of recognizing at least one amino acid at positions of 1 to 157 in an amino acid sequence of SEQ ID NO: 1 or recognizing at least one amino acid at positions of 202 to 305 in an amino acid sequence of SEQ ID NO: 1. Recognizing at least one amino acid at positions of 1 to 157 in an amino acid sequence of SEQ ID NO: 1 means that a monoclonal antibody or a fragment thereof recognizes at least one amino acid in this region.

An patient of the pharmaceutical composition of the present invention is assumed arteriosclerosis and metabolic syndrome. Effective dose is selected in the range of 0.01 mg to 100 mg per 1 kg of body weight per one time. Alternatively, a dose of 5 to 5000 mg, preferably a dose of 10 to 500 mg per a patient may be selected. However, a dose of the pharmaceutical composition containing the monoclonal antibody of the present invention or a fragment thereof is not limited to these doses. Administering duration may be also appropriately selected depending on the age, symptom and the like of the patient. The pharmaceutical composition of the present invention may also include a pharmaceutically acceptable carrier or additive as well depending on the route of administration. Examples of such carrier and additive include water, pharmaceutically acceptable organic solvent, collagen, polyvinyl alcohol, polyvinylpyrrolidone, sodium alginate, water-soluble dextran, pectin, methyl cellulose, ethyl cellulose, casein, diglycerin, propylene glycol, polyethylene glycol, Vaseline, human serum albumin (HSA), mannitol, sorbitol, lactose, and surfactants permitted as a pharmaceutical additive. An additive for use is appropriately selected or combined from the above depending on the dose form, but, it is not limited thereto.

The present invention is described below in more detail by the way of examples. However, the present invention is not limited to the following examples. Unless specifying otherwise as a procedure for preparing antibody, we used methods described in Immunochemistry in Practice (Blackwell Scientific Publications). Also unless specifying otherwise as the genetic engineering techniques, we used methods described in Molecular Cloning: A Laboratory Manual, $2^{nd}$ Edition (Cold Spring Harbor Laboratory).

Example 1

Preparation of Recombinant Adenovirus to Express Baboon EL
The cDNA of baboon EL with C2 tag was cloned into pShuttle vector (Clontech). This sub-cloned vector and the vector carrying adenoviral backbone gene was digested by PI-SceI and I-CeuI enzyme (Adeno-x Accessory Kit, Clontech). The ligation reaction of the digested fragments was conducted at 16° C. for 3 hrs (Ligation high, TOYOBO) and the ligation products were transformed to E. coli (OneShot stbl3 Chemically Competent, Invitrogen). After selection of Ampicillin, plasmid DNA was purified from obtained clone (QIAprep spin Miniprep Kit, QIAGEN) and was digested by Pad enzyme to cut E. coli growth area (New England Biolabs). With the above, plasmid DNA was acquired to generate adenovirus vector. Acquired plasmid DNA was transfected to HEK293 cells (American Type Culture Collection) using Lipofectamine 2000 (Invitrogen) and cultured in DMEM containing 10% FBS at 37° C. After transfection, we changed culture medium every 5 days and we continued to culture cells until confirming cytopathic effect (CPE). After confirming CPE, the cells and culture supernatant were collected. After the cells were subjected to five rounds of freeze/thaw with dry ice-methanol bath and warm bath, supernatant which was obtained by 15 min centrifugation was collected as cell extracts. The culture supernatant was mixed with the culture medium and used as a primary virus stock. Amplification of the virus stock was achieved by adding the virus stock to HEK293 cells and repeating same procedures. After amplification of the virus stock, the finally obtained cell extracts was treated with Benzonase (Merck-Novagen) for 30 min at 37° C., then supernatant was used for the purification of viral vector by following density gradient centrifugation. We overlaid PBS containing 1.5, 1.35, 1.25 g/cm³ cesium chloride into the centrifuging tube, then overlaid the supernatant. We centrifuged this at 35,000 rpm for 1 hr at 16° C., and collected obtained virus vector by visual. Collected viral vector was dialyzed against PBS containing 10% glycerol, and then used as purified adenoviral vectors. A part of viral vector was used for titration (Adeno-X rapid titer kit, Clontech) and self-proliferative potential gain-of-emergence decision, and only used to immunize the following only those without abnormal. The amino acid sequence of baboon EL-C2 tag was described in SEQ ID NO: 2.

Example 2

Preparation of EL Heparin Extract
The DNA encoding baboon EL was cloned into pcDNA3.1 expression vector (Invitrogen). The expression vector was transfected into HEK293F cells and cultured at 37° C., 8% CO2 for 2 days. The cell culture was centrifuged and the cells were collected, the cells were suspended with PBS containing 20 U/mL of Heparin. The cell suspension was incubated at 37° C. for 45 min. The supernatant obtained by removing cells with centrifugation was used as baboon EL enzyme solution. Using the same method, cynomolgus monkey EL, human [1-157]-mouse chimeric EL, human [1-53]-mouse chimeric EL, human [61-111]-mouse chimeric EL, rabbit EL, mouse EL, human [1-305]-mouse chimeric EL and human [202-500]-mouse chimeric EL heparin extract were prepared. The amino acid sequences of cynomolgus monkey EL, human [1-157-mouse chimeric EL, human [1-53]-mouse chimeric EL, human [61-111]-mouse chimeric EL, rabbit EL, mouse EL, human [1-305]-mouse chimeric EL and human [202-500]-mouse chimeric EL with C2 tag were described SEQ ID NO: 2, 3, 4, 5, 6, 7, 96 and 97.

Example 3

Immunization of Baboon EL Expression Adenoviral Vector
6 week-old female mice (A/J Jms Slc spices, obtained from Nihon SLC) were immunized intravenously, subcutaneously or intramuscularly with 2×10⁹ i.f.u. adenovirus vector carrying baboon EL gene. Every 7 days after administration, the blood sample was taken from tail vein and the antibody titer was measured. And, additional administration of adenovirus vector carrying baboon EL gene was done intravenously, subcutaneously or intramuscularly. The mice which showed high titer were booster immunized from tail vein as the final administration.

Example 4

Production of Hybridoma Producing Antibodies
The abdominal cavity of mouse which showed high titer was opened and the spleen was isolated three days after final immunization. Spleen cells and mouse myeloma cells (p3x63-Ag8.U1, Tokyo tumor laboratories) were fused using 50% polyethylene glycol 4000, and hybridoma cells were selected in a culture medium containing hypoxanthine, aminopterin and thymidine.

Example 5

Screening of a Hybridoma Cells which Produces Anti-Baboon EL Antibodies

Ten days after the cell fusion, hybridoma cells which produced anti-baboon EL antibodies were selected. Each well of 384 well microtiter plates (Nunc) was immobilized with 35 μL of Tris/HCl buffer (50 mM Tris/HCl, pH 7.5) containing 0.35 μg of anti-mouse IgG-Fc (Jackson Immuno Research). The plates were incubated at 4° C. for 16 hr. After washing the wells one time with 90 μL of washing solution (saline containing 0.01% Tween20), 100 μL of Block-Ace (Dainihonsumitomo) was added to the wells and incubated at room temperature for 2 hr (immobilized plate of anti-mouse IgG-Fc antibody). After washing the wells three times with 90 μL of washing buffer, 15 μL of assay buffer containing baboon EL heparin extract (50 mM Tris/HCl, PH 7.4 containing 4% Block-Ace, 0.05% Tween20, 150 mM NaCl) were added to the wells and incubated at room temperature at 4° C. for 16 hr. After washing the wells three times with 90 μL of washing buffer, 15 μL assay buffer containing biotin-labeled anti-C2-tag antibody and HRP-labeled Streptavidin (Thermo scientific) were added to the wells and incubated at room temperature for 1 hr. After washing the wells three times with 90 μL of washing buffer, 15 μL of TMB+-Substrate-Chromogen (DAKO) was added and incubated at room temperature for 30 min. The reaction was stopped with adding 15 μL of 0.05 M $H_2SO_4$ and then measured absorbance 450 nm. From the result of screening, the 11 hybridomas (55A1, 7D4, 14A1, 2D5, 53A11, 13B3, 23H8, 16B3, 16E7, 14E1 and 19E7) which produced anti-baboon EL antibody was selected. The antibody which was produced by hybridoma of 55A1, 7D4, 14A1, 2D5, 53A11, 13B3, 23H8, 16B3, 16E7, 14E1 and 19E7 were named respectively 55A1, 7D4, 14A1, 2D5, 53A11, 13B3, 23H8, 16B3, 16E7, 14E1 and 19E7 antibody. The IgG subclasses were determined using Mouse Immunoglobulin Isotyping Kit (BD Biosciences).

The subclass of 55A1, 2D5, 53A11, 13B3, 23H8, 16B3 and 19E7 was IgG2a. The subclass of 7D4, 14A1, 16E7 and 14E1 was IgG1.

Example 6

Measurement of Inhibitory Activity of Anti-EL Antibodies Against EL

Figure 1B:
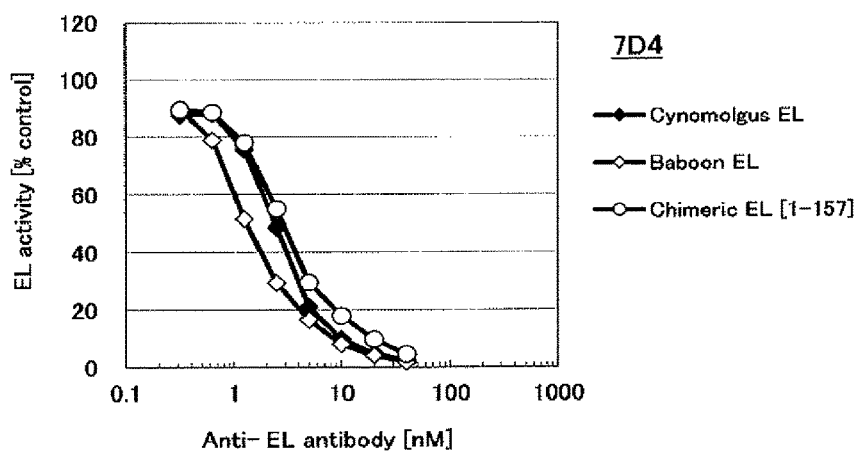
FIG. 1B shows measurement results of inhibiting enzymatic activity of 7D4 antibody against cynomolgus EL, baboon EL and human (1-157) mouse chimera EL.
Figure 1C:
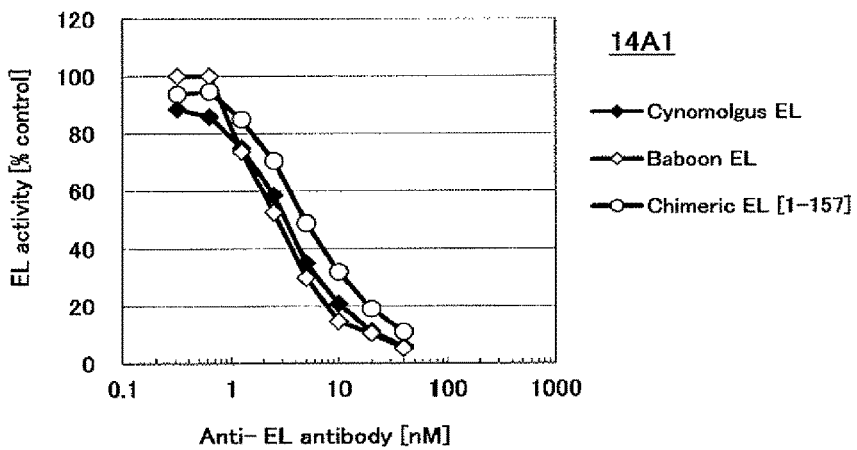
FIG. 1C shows measurement results of inhibiting enzymatic activity of 14A1 antibody against cynomolgus EL, baboon EL and human (1-157) mouse chimera EL.
Figure 1D:
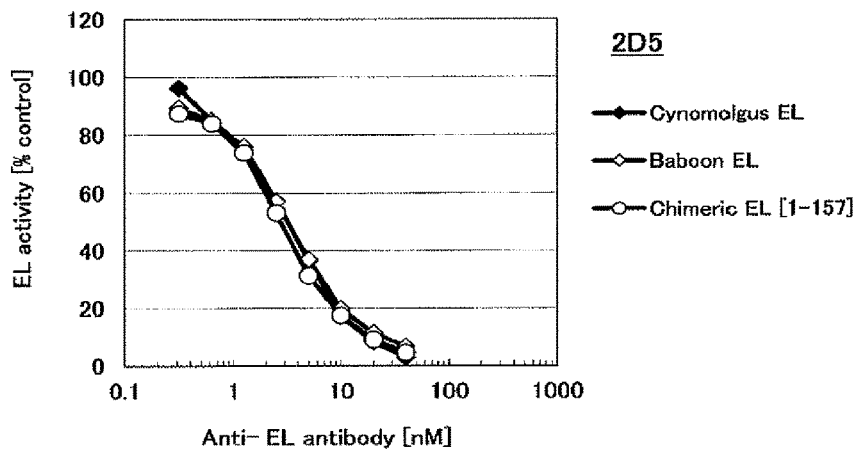
FIG. 1D shows measurement results of inhibiting enzymatic activity of 2D5 antibody against cynomolgus EL, baboon EL and human (1-157) mouse chimera EL.
Figure 1E:
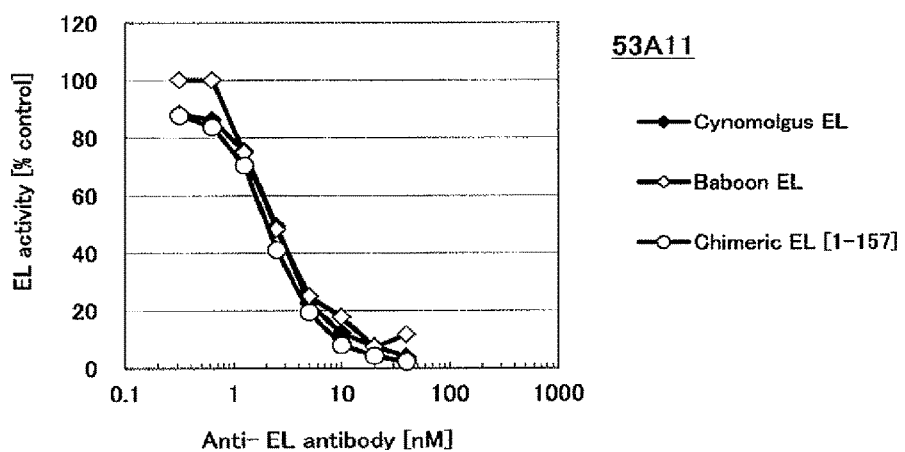
FIG. 1E shows measurement results of inhibiting enzymatic activity of 53A11 antibody against cynomolgus EL, baboon EL and human (1-157) mouse chimera EL.
Figure 1F:
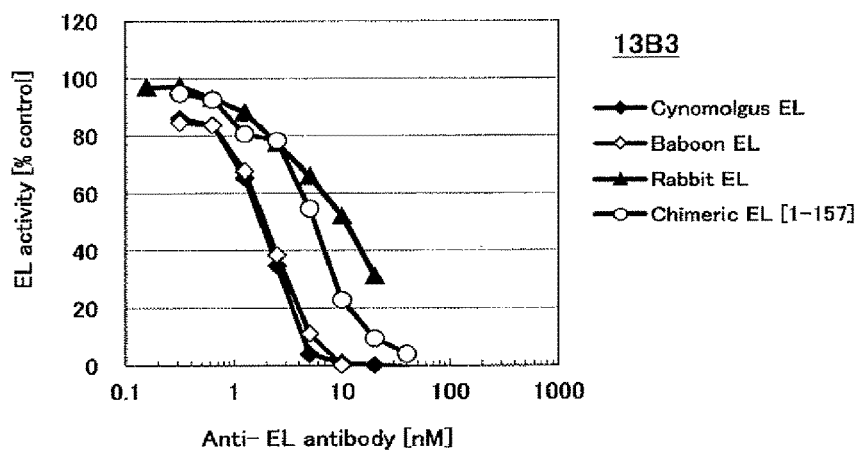
FIG. 1F shows measurement results of inhibiting enzymatic activity of 13B3 antibody against cynomolgus EL, baboon EL, rabbit EL and human (1-157) mouse chimera EL.
Figure 1G:
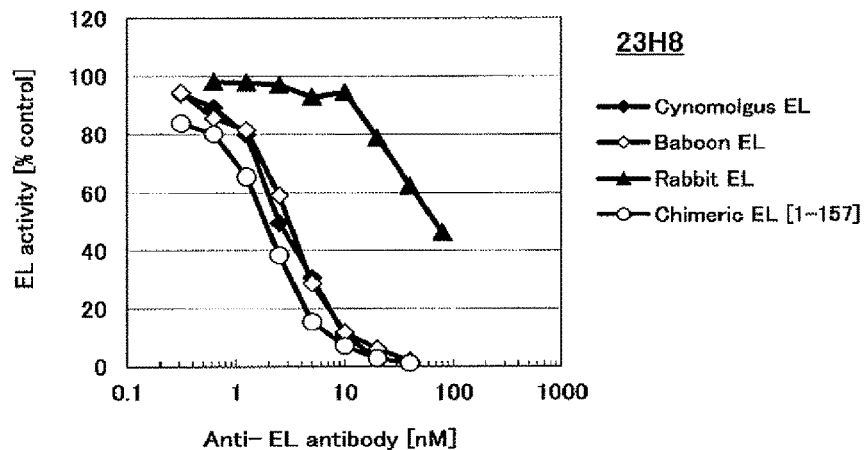
FIG. 1G shows measurement results of inhibiting enzymatic activity of 23H8 antibody against cynomolgus EL, baboon EL, rabbit EL and human (1-157) mouse chimera EL.
Figure 1H:
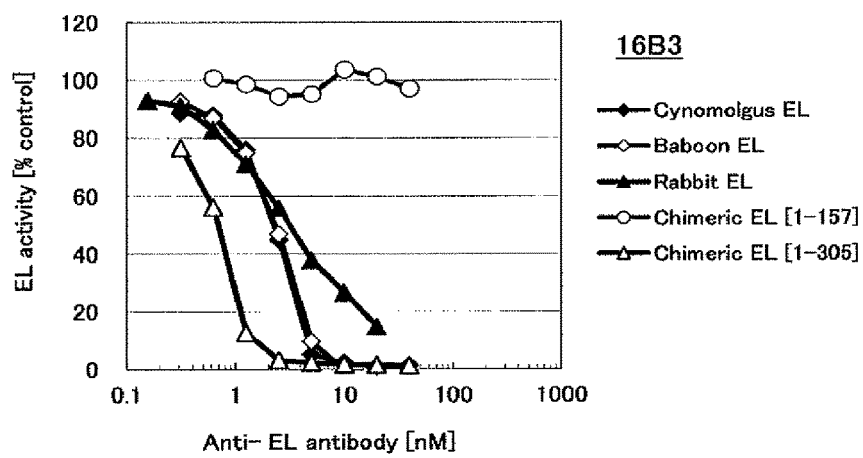
FIG. 1H shows measurement results of inhibiting enzymatic activity of 16B3 antibody against cynomolgus EL, baboon EL, rabbit EL, human (1-157) mouse chimera EL and human (1-305) mouse chimera EL.
Figure 1I:
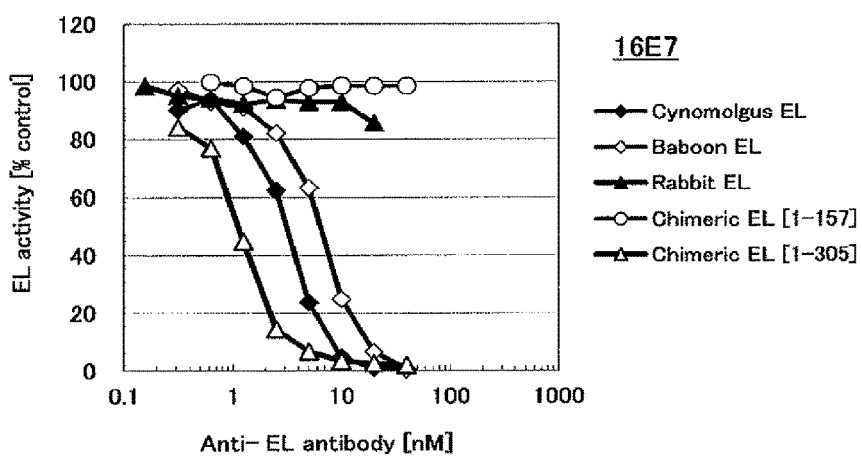
FIG. 1I shows measurement results of inhibiting enzymatic activity of 16E7 antibody against cynomolgus EL, baboon EL, rabbit EL, human (1-157) mouse chimera EL and human (1-305) mouse chimera EL.
Figure 1J:
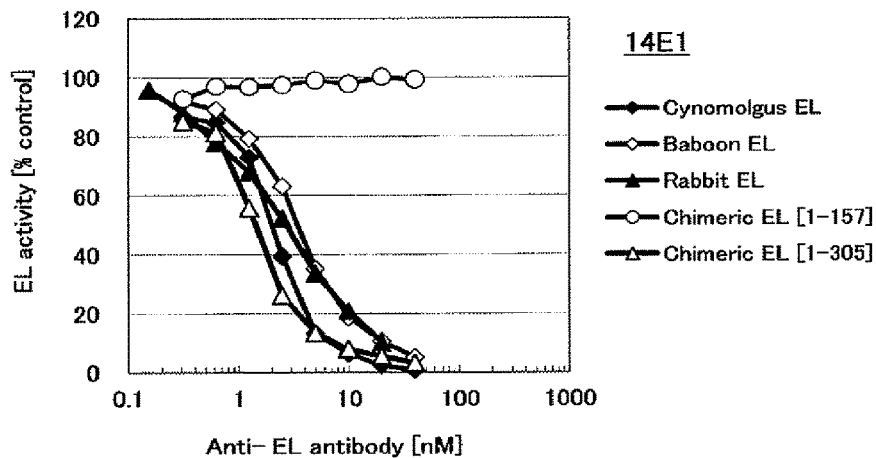
FIG. 1J shows measurement results of inhibiting enzymatic activity of 14E1 antibody against cynomolgus EL, baboon EL, rabbit EL, human (1-157) mouse chimera EL and human (1-305) mouse chimera EL.
Figure 1K:
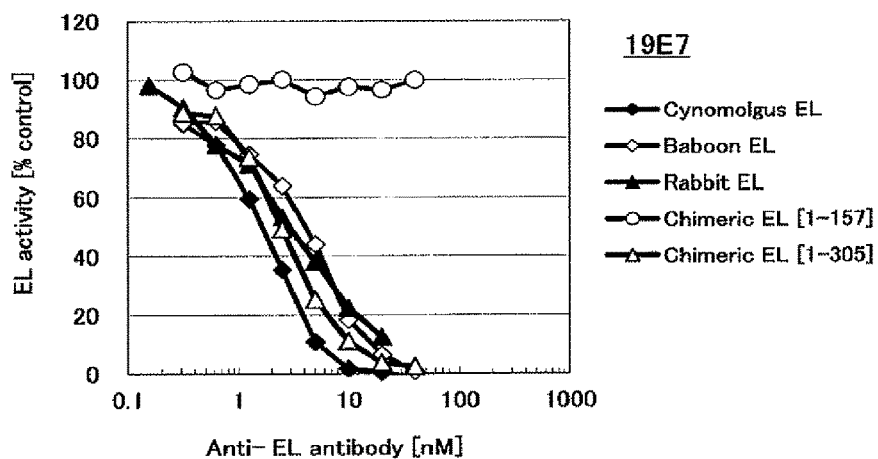
FIG. 1K shows measurement results of inhibiting enzymatic activity of 19E7 antibody against cynomolgus EL, baboon EL, rabbit EL, human (1-157) mouse chimera EL and human (1-305) mouse chimera EL.

The inhibitory activity of anti-EL antibodies (55A1, 7D4, 14A1, 2D5, 53A11, 13B3, 23H8, 16B3, 16E7, 14E1 and 19E7) against baboon EL, cynomolgus monkey EL, human (1-157) mouse chimeric EL, human (1-53) mouse chimeric EL, human (61-111) mouse chimeric EL, rabbit EL, mouse EL, human (1-305) mouse chimeric EL and human (202-500) mouse chimeric EL were measured as follows. Anti-EL antibody solution, assay buffer (20 mM Tris/HCl (pH 7.5), 0.5% BSA, 4 mM $CaCl_2$, 150 mM NaCl) and 2 mg/mL human HDL (Athens Research & Technology) were mixed in a microtiter plate, followed by adding EL heparin extract. After incubation at 37° C. for 90 min, non-esterified Fatty Acid (NEFA) released from HDL was determined using a commercially available kit (NEFA C test-Wako, Wako). The NEFA amount was used as enzyme activity index. Enzyme activity in the case of adding no anti-EL antibody was determined as control value and specific activity was calculated against the control value at each concentration of the anti-EL antibody (FIG. 1A~K). The concentration of anti-EL antibody where 50% of EL activity was inhibited was calculated from the inhibition curve as IC50 value.

Example 7

Measurement of Inhibitory Activity of Anti-EL Antibody Against HL and LPL

Figure 2A:
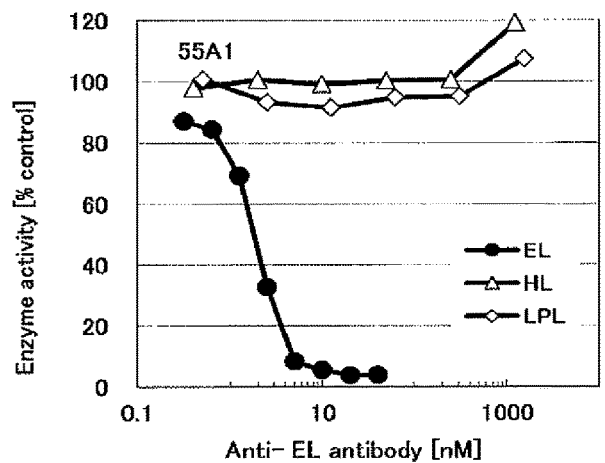
FIG. 2A shows measurement results of inhibiting enzymatic activity of 55A1 antibody against human HL and human LPL.
Figure 2B:
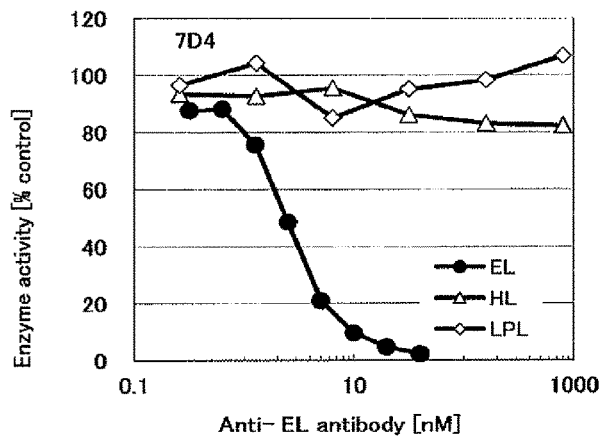
FIG. 2B shows measurement results of inhibiting enzymatic activity of 7D4 antibody against human HL and human LPL.
Figure 2C:
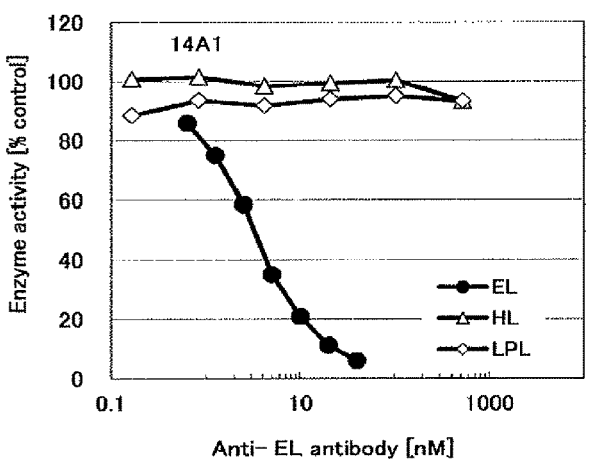
FIG. 2C shows measurement results of inhibiting enzymatic activity of 14A1 antibody against human HL and human LPL.
Figure 2D:
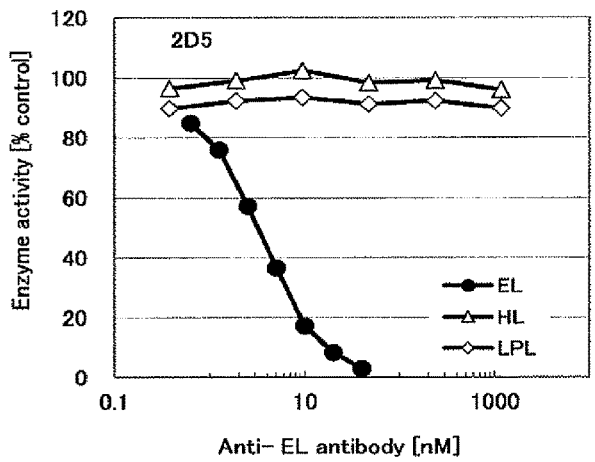
FIG. 2D shows measurement results of inhibiting enzymatic activity of 2D5 antibody against human HL and human LPL.
Figure 2E:
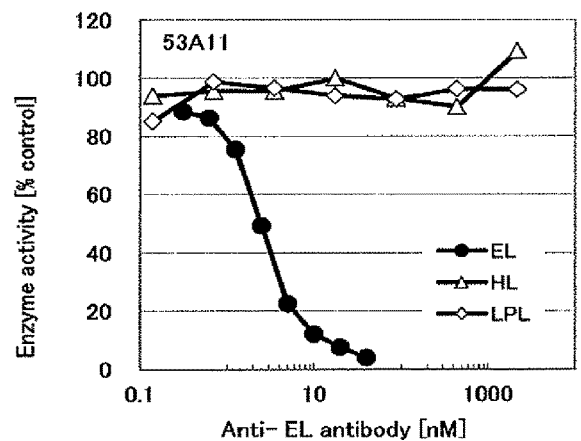
FIG. 2E shows measurement results of inhibiting enzymatic activity of 53A11 antibody against human HL and human LPL.
Figure 2F:
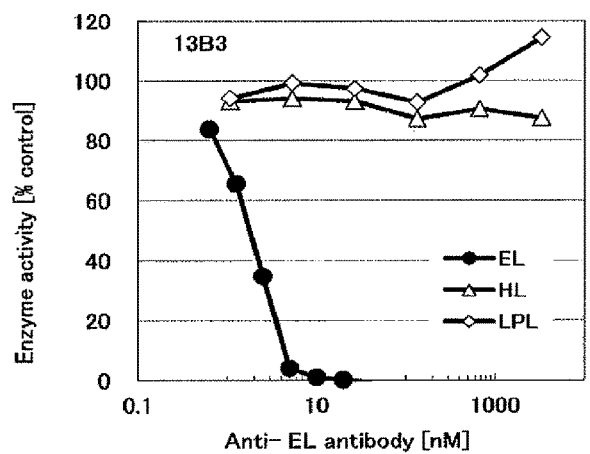
FIG. 2F shows measurement results of inhibiting enzymatic activity of 13B3 antibody against human HL and human LPL.
Figure 2G:
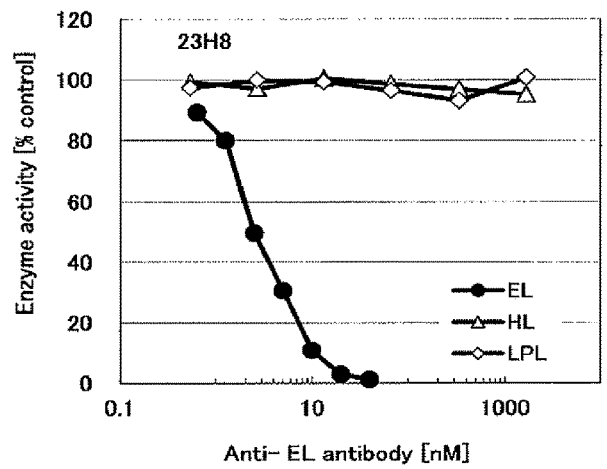
FIG. 2G shows measurement results of inhibiting enzymatic activity of 23H8 antibody against human HL and human LPL.
Figure 2H:
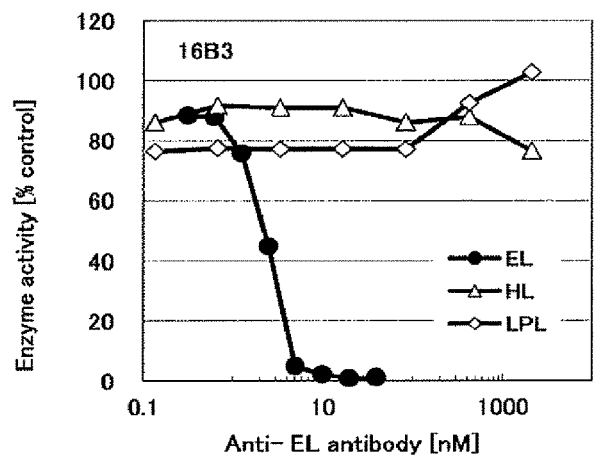
FIG. 2H shows measurement results of inhibiting enzymatic activity of 16B3 antibody against human HL and human LPL.
Figure 2I:
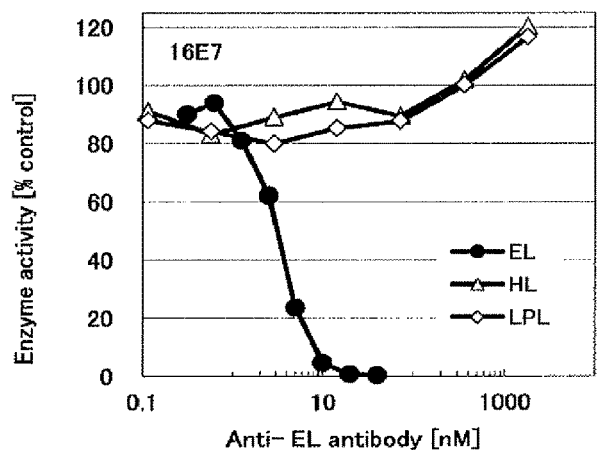
FIG. 2I shows measurement results of inhibiting enzymatic activity of 16E7 antibody against human HL and human LPL.
Figure 2J:
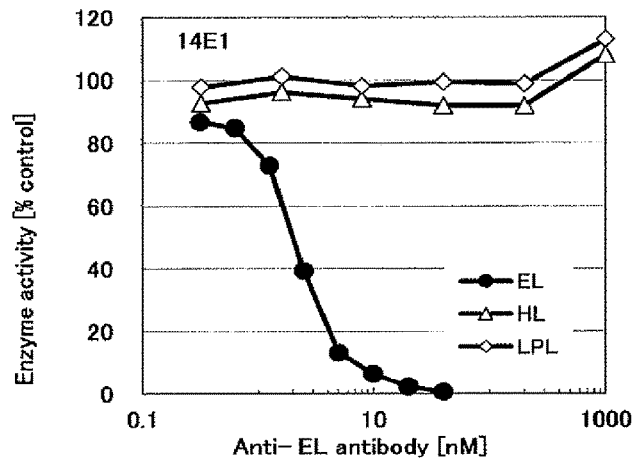
FIG. 2J shows measurement results of inhibiting enzymatic activity of 14E1 antibody against human HL and human LPL.
Figure 2K:
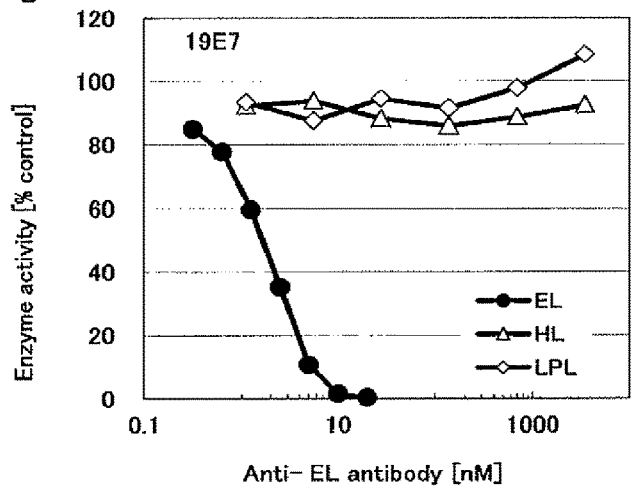
FIG. 2K shows measurement results of inhibiting enzymatic activity of 19E7 antibody human HL and human LPL.
Figure 2L:
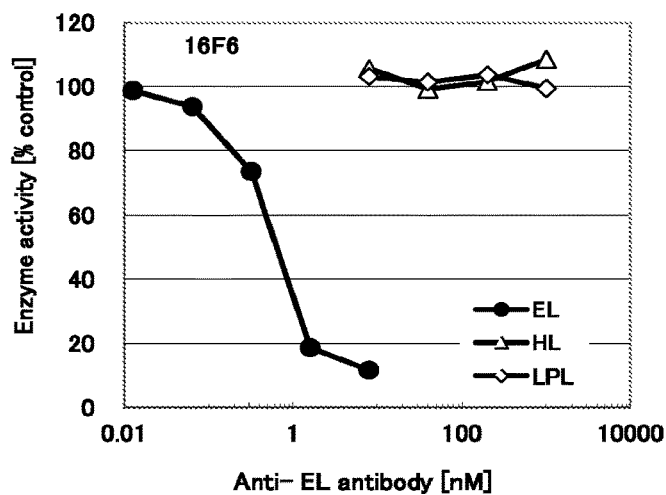
FIG. 2L shows measurement results of inhibiting enzymatic activity of 16F6 antibody human HL and human LPL.

The DNA encoding human HL was cloned into pcDNA3.1 expression vector (Invitrogen). The expression vector was transfected into HEK293F cells and cultured at 37° C., 8% CO2 for 2 days. The cells were centrifuged and the cells ware collected, the cells were suspended with PBS containing 20 U/mL of Heparin (SIGMA). The cell suspension was incubated at 37° C. for 45 min. The supernatant obtained by removing cells with centrifugation was used as human HL enzyme solution. Human LPL enzyme solution was prepared by using the same method. After adding anti-EL antibody to the solution containing 20 mM Tris-HCl Buffer (pH 7.5), 0.5% bovine serum albumin, 4 mM $CaCl_2$, 150 mM NaCl and 0.5 mg/mL human VLDL (INTRACEL), human HL or human LPL enzyme was added (total volume 10 μl). After reaction at 37° C. for 2 hr, free fatty acid (NEFA) made from VLDL by HL or LPL enzyme was determined using NEFA C-test Wako (Wako), the NFFA amount was used as enzyme activity index. Enzyme activity in the case of adding no anti-EL antibody was determined as control value and the specific activity was calculated against the control value at each concentration of the antibody (FIG. 2A~K). For comparison, the result was described side by side inhibition curve of cynomolgus monkey EL. As a result, it was shown that 55A1, 7D4, 14A1, 2D5, 53A11, 13B3, 23H8, 16B3, 16E7, 14E1, 19E7 and 16F6 antibodies didn't inhibit neither HL nor LPL enzyme activity.

Example 8

Measurement of Binding Activity of Anti-EL Antibody to EL

Figure 3A:
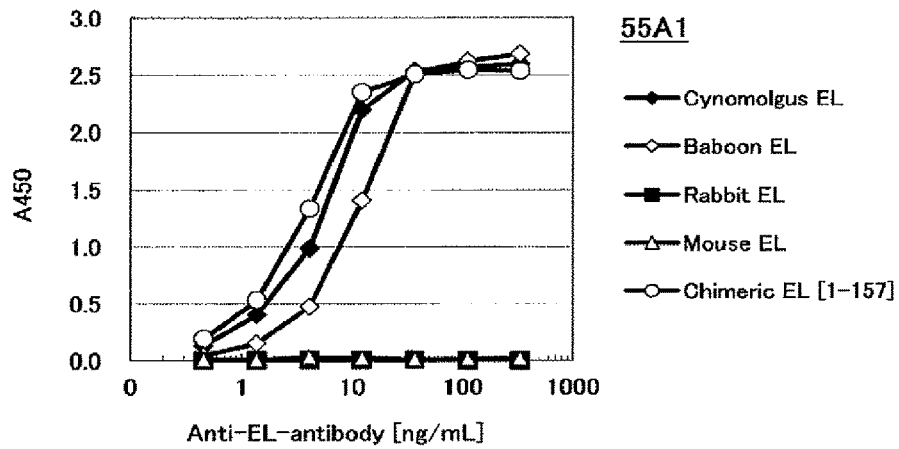
FIG. 3A shows measurement results of binding activity of 55A1 antibody against cynomolgus EL, baboon EL, rabbit EL, mouse EL and human (1-157) mouse chimera EL.
Figure 3B:
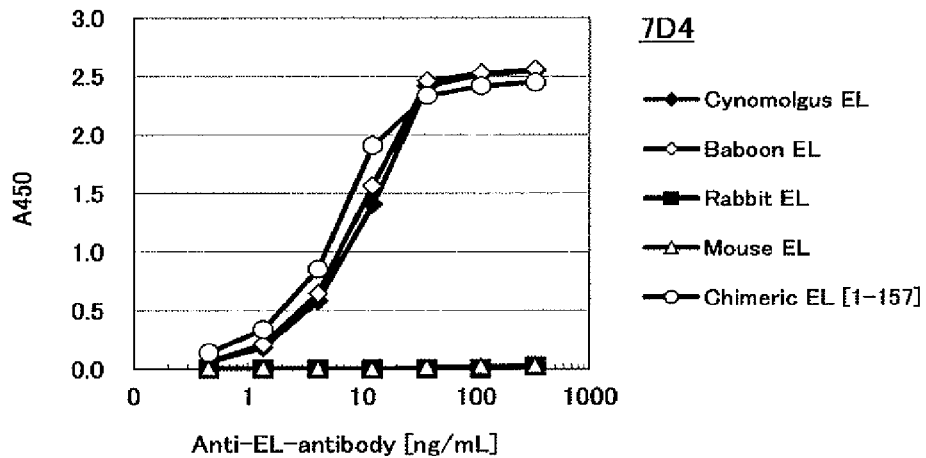
FIG. 3B shows measurement results of inhibiting enzymatic activity of 7D4 antibody against cynomolgus EL, baboon EL, rabbit EL, mouse EL and human (1-157) mouse chimera EL.
Figure 3C:
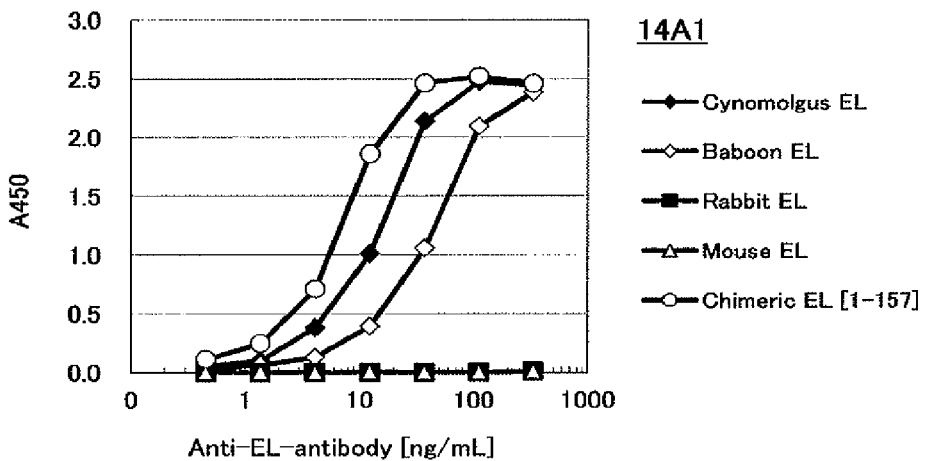
FIG. 3C shows measurement results of inhibiting enzymatic activity of 14A1 antibody against cynomolgus EL, baboon EL, rabbit EL, mouse EL and human (1-157) mouse chimera EL.
Figure 3D:
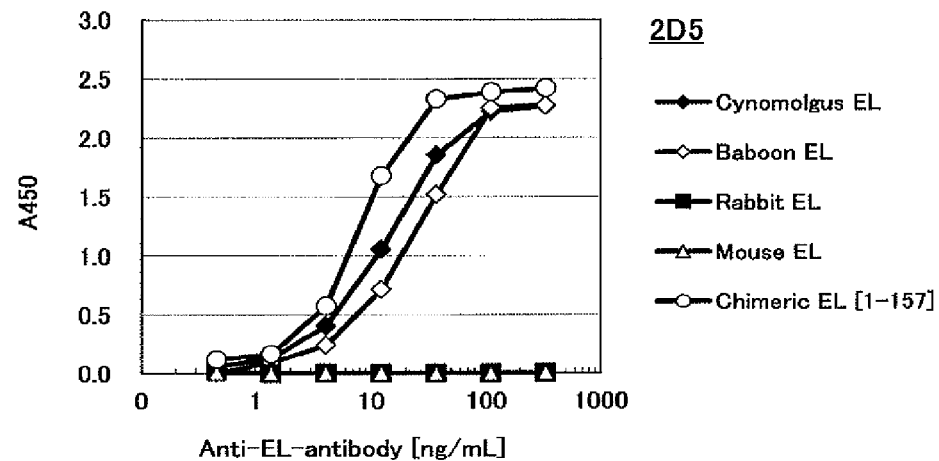
FIG. 3D shows measurement results of inhibiting enzymatic activity of 2D5 antibody against cynomolgus EL, baboon EL, rabbit EL, mouse EL and human (1-157) mouse chimera EL.
Figure 3E:
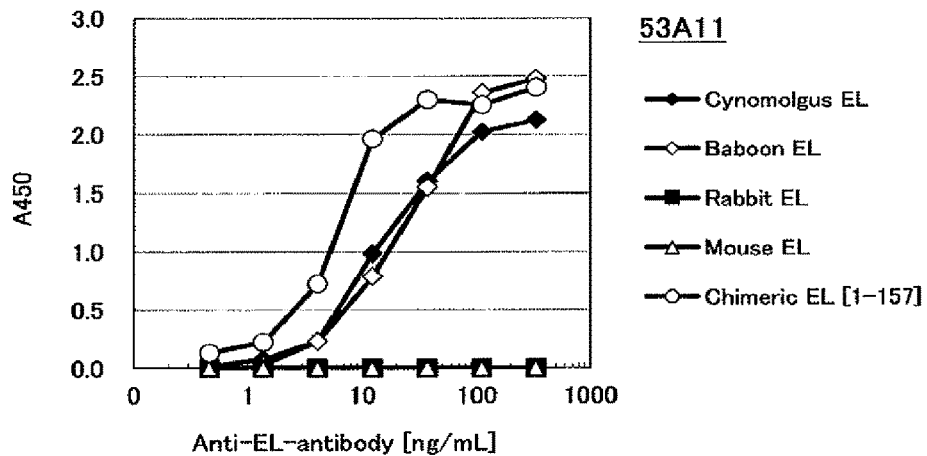
FIG. 3E shows measurement results of inhibiting enzymatic activity of 53A11 antibody against cynomolgus EL, baboon EL, rabbit EL, mouse EL and human (1-157) mouse chimera EL.
Figure 3F:
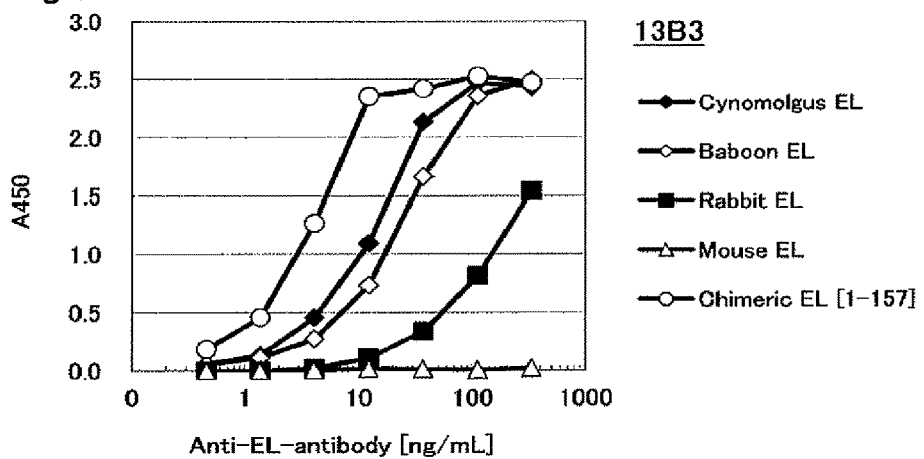
FIG. 3F shows measurement results of inhibiting enzymatic activity of 13B3 antibody against cynomolgus EL, baboon EL, rabbit EL, mouse EL and human (1-157) mouse chimera EL.
Figure 3G:
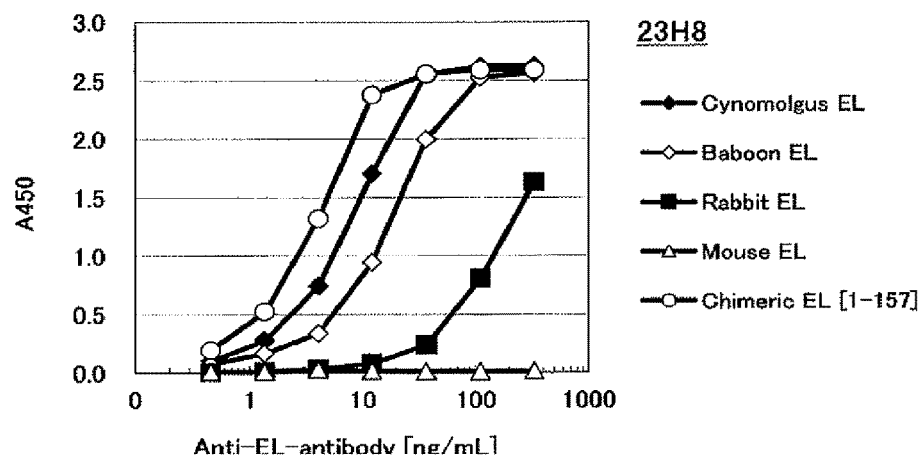
FIG. 3G shows measurement results of inhibiting enzymatic activity of 23H8 antibody against cynomolgus EL, baboon EL, rabbit EL, mouse EL and human (1-157) mouse chimera EL.
Figure 3H:
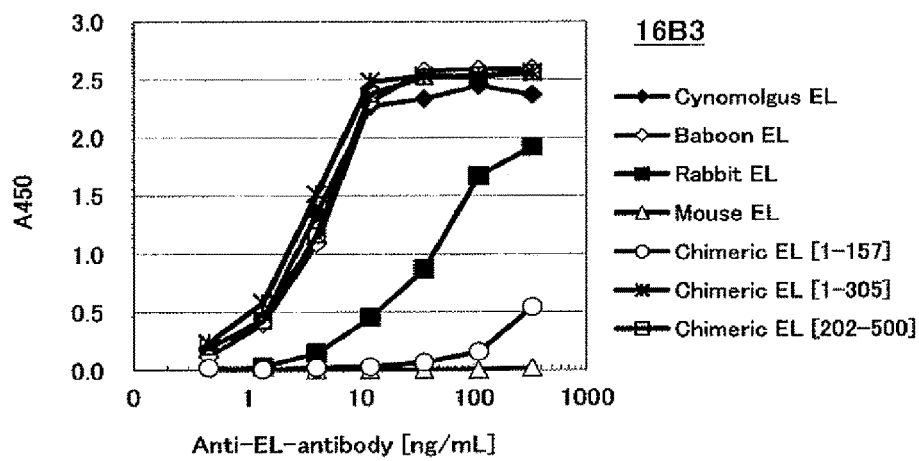
FIG. 3H shows measurement results of inhibiting enzymatic activity of 16B3 antibody against cynomolgus EL, baboon EL, rabbit EL, mouse EL, human (1-157) mouse chimera EL, human (1-305) mouse chimera EL and human (202-500) mouse chimera EL.
Figure 3I:
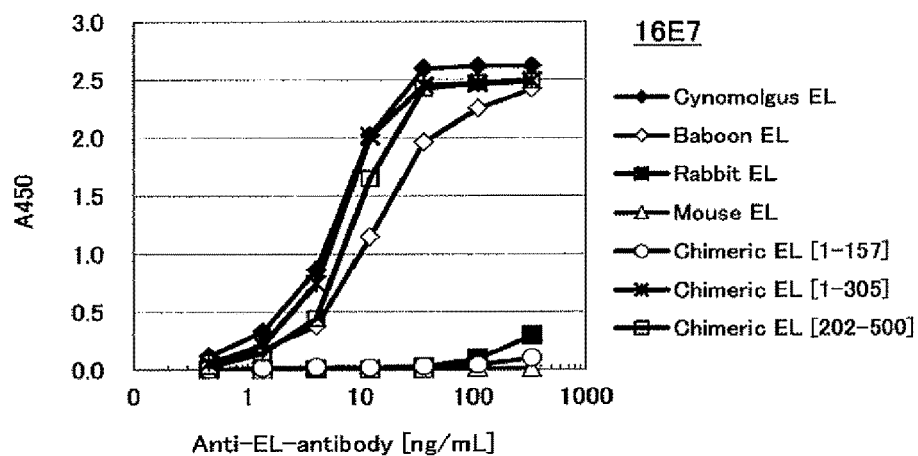
FIG. 3I shows measurement results of inhibiting enzymatic activity of 16E7 antibody against cynomolgus EL, baboon EL, rabbit EL, mouse EL, human (1-157) mouse chimera EL, human (1-305) mouse chimera EL and human (202-500) mouse chimera EL.
Figure 3J:
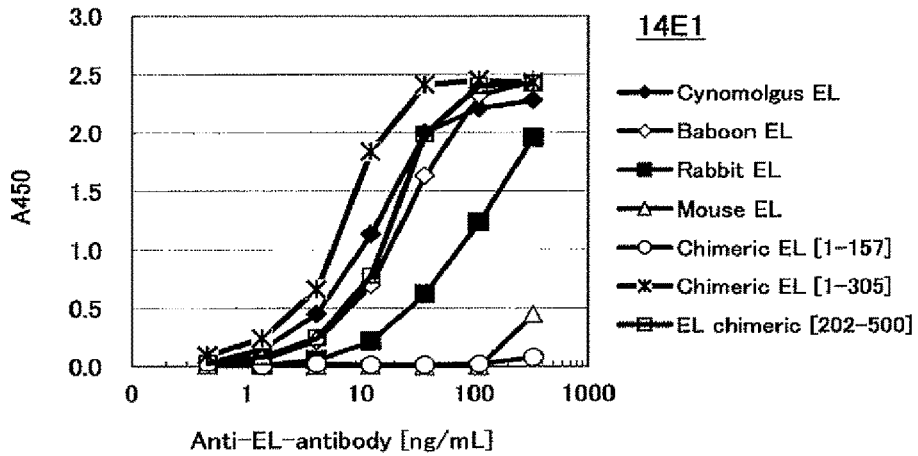
FIG. 3J shows measurement results of inhibiting enzymatic activity of 14E1 antibody against cynomolgus EL, baboon EL, rabbit EL, mouse EL, human (1-157) mouse chimera EL, human (1-305) mouse chimera EL and human (202-500) mouse chimera EL.

Assay buffer containing 15 μl of anti-EL antibody was added to anti-mouse IgG-Fc antibody-immobilized microtiter plate, and incubated for 2 hr. After washing the wells three times with 90 μL of washing buffer, 15 μl of cynomolgus monkey EL, baboon EL, rabbit EL, mouse EL, human [1-157]-mouse chimeric EL, human [1-305]-mouse chimeric EL or human [202-500]-mouse chimeric EL heparin extract was added and incubated at 4° C. for 16 hr. After washing the wells three times with 90 μL of washing buffer, 15 μl of assay buffer containing biotin-labeled anti-C2-tag antibody and HRP-labeled Streptavidin were added to the wells and incubated at room temperature for 1 hr. After washing the wells three times with 90 μL of washing buffer, 15 μL of TMB+-Substrate-Chromogen (DAKO) was added and incubated at room temperature for 30 min and then 15 μL of 0.05 M H2SO4 was added and absorbance at 450 nm was measured (FIG. 3A~3K).

As a result, 55A1, 7D4, 14A1, 2D5, 53A11, 13B3 and 23H8 bound cynomolgus monkey EL, baboon EL and human [1-157]-mouse chimeric EL, but did not bind mouse EL. In addition, 13B3 and 23H8 bound rabbit EL, but 55A1, 7D4, 14A1 2D5 and 53A11 did not. On the other hand, 16B3, 16E7, 14E1 and 19E7 bound cynomolgus monkey EL, baboon EL, human [1-305]-mouse chimeric EL and human [202-500]-mouse chimeric EL, but did not bind mouse E1 and human [1-157]-mouse chimeric EL. In addition, 16B3, 14E1 and 19E7 bound rabbit EL, but 16E7 did not.

Example 9

Binding Affinities of Anti-EL Antibodies

The binding affinities of anti-EL antibodies were measured using Biacore. Anti-C2-tag antibody was immobilized on a sensor chip CM5 (GE HealthCare) using amine-coupling and baboon EL, cynomolgus monkey EL or human [1-305]-mouse chimeric EL heparin extract was added and EL was captured on the sensor chip. Then, anti-EL antibodies were added and the binding affinities were calculated by bivalent fitting of BIAevaluation software. The results were summarized in Table 1~3.

TABLE 1

Affinity for Baboon EL

| Clone name | ka[1/Ms] | kd[1/s] | $K_D$ [M] |
|---|---|---|---|
| 55A1 | $3.5 \times 10^5$ | $4.2 \times 10^{-4}$ | $1.2 \times 10^{-9}$ |
| 7D4 | $7.8 \times 10^4$ | $3.5 \times 10^{-4}$ | $4.5 \times 10^{-9}$ |
| 14A1 | $1.9 \times 10^5$ | $6.2 \times 10^{-4}$ | $3.3 \times 10^{-9}$ |
| 2D5 | $7.7 \times 10^5$ | $1.7 \times 10^{-4}$ | $2.2 \times 10^{-9}$ |
| 53A11 | $1.7 \times 10^5$ | $2.6 \times 10^{-4}$ | $1.6 \times 10^{-9}$ |
| 13B3 | $6.1 \times 10^4$ | $3.1 \times 10^{-4}$ | $5.1 \times 10^{-9}$ |
| 23H8 | $1.5 \times 10^5$ | $4.4 \times 10^{-4}$ | $2.9 \times 10^{-9}$ |
| 16B3 | $3.1 \times 10^4$ | $9.8 \times 10^{-5}$ | $3.2 \times 10^{-9}$ |
| 16E7 | $5.3 \times 10^4$ | $2.5 \times 10^{-4}$ | $4.7 \times 10^{-9}$ |
| 14E1 | $1.5 \times 10^5$ | $8.5 \times 10^{-4}$ | $5.8 \times 10^{-9}$ |
| 19E7 | $6.7 \times 10^4$ | $8.3 \times 10^{-4}$ | $1.2 \times 10^{-9}$ |

TABLE 2

Affinity for Cynomolgus EL

| Clone name | ka[1/Ms] | kd[1/s] | $K_D$ [M] |
|---|---|---|---|
| 55A1 | $2.5 \times 10^5$ | $4.4 \times 10^{-4}$ | $1.7 \times 10^{-9}$ |
| 7D4 | $1.2 \times 10^5$ | $2.3 \times 10^{-4}$ | $1.9 \times 10^{-9}$ |
| 14A1 | $2.1 \times 10^5$ | $8.1 \times 10^{-4}$ | $3.9 \times 10^{-9}$ |
| 2D5 | $7.4 \times 10^5$ | $2.8 \times 10^{-4}$ | $3.8 \times 10^{-9}$ |
| 53A11 | $9.1 \times 10^5$ | $3.8 \times 10^{-4}$ | $4.2 \times 10^{-9}$ |
| 13B3 | $4.7 \times 10^4$ | $4.1 \times 10^{-4}$ | $8.7 \times 10^{-9}$ |
| 23H8 | $1.2 \times 10^5$ | $7.5 \times 10^{-4}$ | $6.1 \times 10^{-9}$ |
| 16B3 | $4.2 \times 10^5$ | $8.9 \times 10^{-5}$ | $2.1 \times 10^{-9}$ |
| 16E7 | $3.2 \times 10^4$ | $3.2 \times 10^{-4}$ | $3.7 \times 10^{-9}$ |
| 14E1 | $1.2 \times 10^5$ | $6.9 \times 10^{-4}$ | $5.9 \times 10^{-9}$ |
| 19E7 | $5.5 \times 10^4$ | $1.8 \times 10^{-4}$ | $3.3 \times 10^{-9}$ |

TABLE 3

Affinity for Human [1-305]-mouse chimeric EL

| No. | Clone name | ka[1/Ms] | kd[1/s] | $K_D$ [nM] |
|---|---|---|---|---|
| 1 | 55A1 | $1.9 \times 10^5$ | $1.4 \times 10^{-4}$ | $7.3 \times 10^{-10}$ |
| 2 | 7D4 | $1.1 \times 10^5$ | $1.1 \times 10^{-4}$ | $9.7 \times 10^{-10}$ |
| 3 | 14A1 | $2.1 \times 10^5$ | $1.0 \times 10^{-4}$ | $5.0 \times 10^{-10}$ |
| 4 | 2D5 | $8.5 \times 10^4$ | $9.3 \times 10^{-5}$ | $1.1 \times 10^{-9}$ |
| 5 | 53A11 | $1.8 \times 10^5$ | $1.1 \times 10^{-4}$ | $6.3 \times 10^{-10}$ |
| 6 | 13B3 | $1.5 \times 10^5$ | $1.4 \times 10^{-4}$ | $9.1 \times 10^{-10}$ |
| 7 | 23H8 | $1.2 \times 10^5$ | $1.1 \times 10^{-4}$ | $8.7 \times 10^{-10}$ |
| 8 | 16B3 | $5.1 \times 10^4$ | $1.9 \times 10^{-4}$ | $3.7 \times 10^{-9}$ |
| 9 | 16E7 | $9.5 \times 10^5$ | $1.0 \times 10^{-4}$ | $1.1 \times 10^{-9}$ |
| 10 | 14E1 | $4.2 \times 10^4$ | $2.3 \times 10^{-4}$ | $5.4 \times 10^{-9}$ |

From the results of Example 5, 6, 8 and 9, the characteristics of anti-EL antibodies were summarized in Table 4.

TABLE 4

| | | Neutralizing activity IC50 [nM] | | | | a region of EL which contributes to antibody binding |
|---|---|---|---|---|---|---|
| No. | Clone name | Subclass | baboon EL | human-mouse chimeric EL | cynomolgus monkey EL | rabbit EL | |
| 1 | 55A1 | IgG2a | 2.0 | 1.1 | 1.5 | N.T. | 1-157 |
| 2 | 7D4 | IgG1 | 2.6 | 3.7 | 2.1 | N.T. | 1-157 |
| 3 | 14A1 | IgG1 | 2.7 | 5.8 | 3.1 | N.T. | 1-157 |
| 4 | 2D5 | IgG2a | 2.9 | 2.7 | 3.0 | N.T. | 1-157 |
| 5 | 53A11 | IgG2a | 2.4 | 2.3 | 1.9 | N.T. | 1-157 |
| 6 | 13B3 | IgG2a | 2.6 | 4.1 | 1.7 | 13 | 1-157 |
| 7 | 23H8 | IgG2a | 3.2 | 1.7 | 2.7 | 67 | 1-157 |
| 8 | 16B3 | IgG2a | 3.0 | 1.3 | 1.9 | 6.3 | 202-305 |
| 9 | 16E7 | IgG1 | 2.1 | 1.1 | 2.5 | >40 | 202-305 |
| 10 | 14E1 | IgG1 | 3.3 | 1.4 | 2.4 | 5.9 | 202-305 |
| 11 | 19E7 | IgG2a | 2.0 | 2.4 | 1.7 | 5.7 | 202-305 |

Example 10

Generation of Anti-EL Antibody which Neutralizes Both Human and Mouse EL

The adenovirus which expresses mouse EL was obtained using the same method as Example 1 and immunized to EL knock-out mice. In the same manner as Example 4 and 5, anti-EL antibody (16F6) was achieved and subclass was IgG1. The neutralizing activity and binding affinity of 16F6 were measured and described in Table 5 and 6.

TABLE 5

| Clone name | EL | neutralizing activity IC50 [nM] |
|---|---|---|
| 16F6 | baboon EL | 2.8 |
| | human (1-305) mouse chimeric EL | 4.0 |
| | mouse EL | 2.5 |
| | rabbit EL | 2.3 |

TABLE 6

| Clone name | EL | Affinity | | |
| | | ka[1/Ms] | kd[1/s] | $K_D$ [nM] |
|---|---|---|---|---|
| 16F6 | human [1-305] mouse chimeric EL | $3.3 \times 10^5$ | $4.0 \times 10^{-3}$ | $1.4 \times 10^{-8}$ |
| | mouse EL | $2.2 \times 10^5$ | $1.5 \times 10^{-4}$ | $6.8 \times 10^{-10}$ |
| | baboon EL | $2.4 \times 10^5$ | $1.0 \times 10^{-4}$ | $4.2 \times 10^{-10}$ |

Example 11

Determination of EL Regions which Contribute to Antibody Binding

Figure 7A:
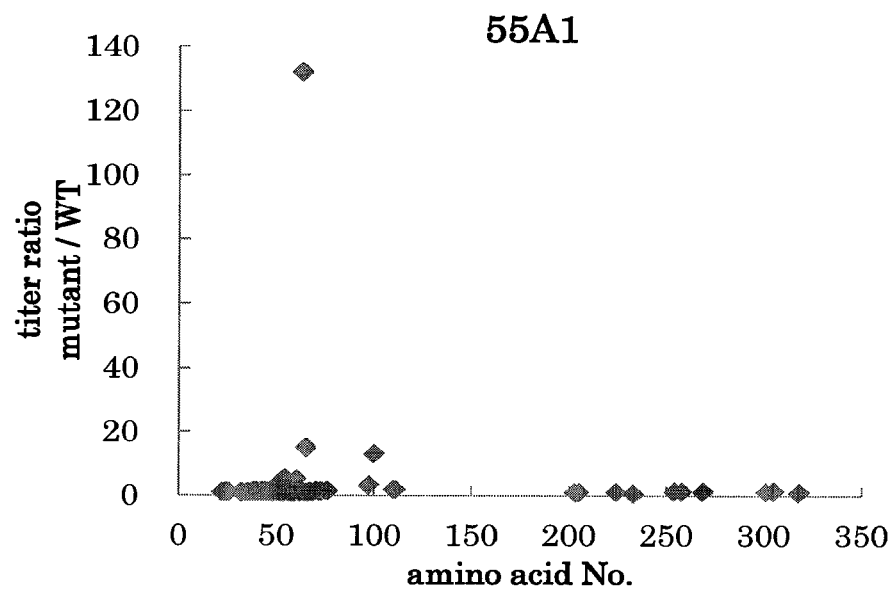
FIG. 7A shows binding activity of 55A1 antibody against baboon EL that was introduced mutation.
Figure 7B:
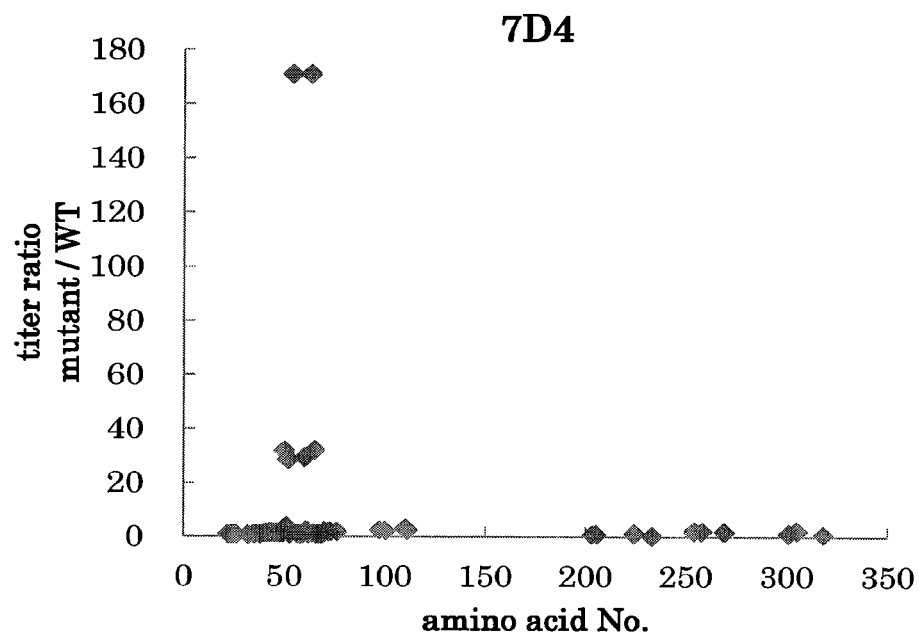
FIG. 7B shows binding activity of 7D4 antibody against baboon EL that was introduced mutation.
Figure 7C:
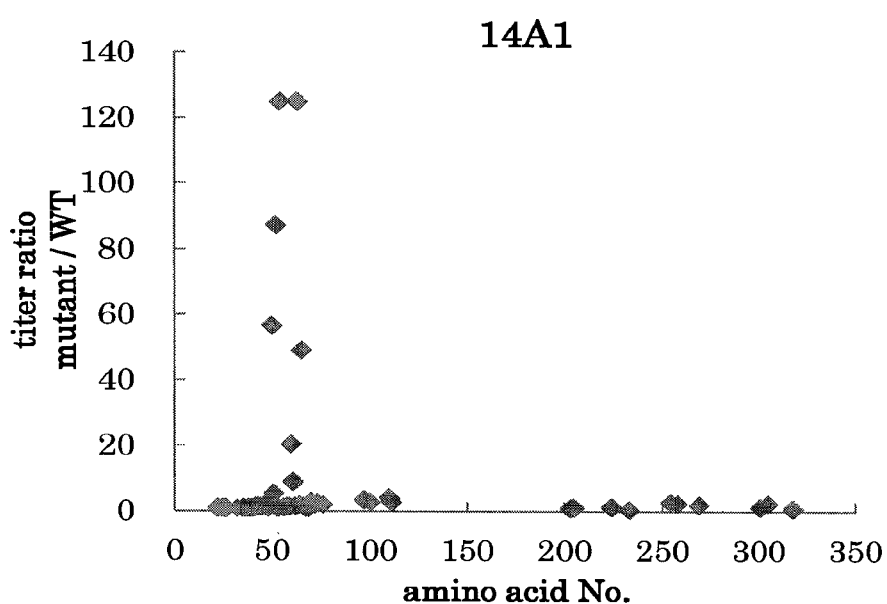
FIG. 7C shows binding activity of 14A1 antibody against baboon EL that was introduced mutation.
Figure 7D:
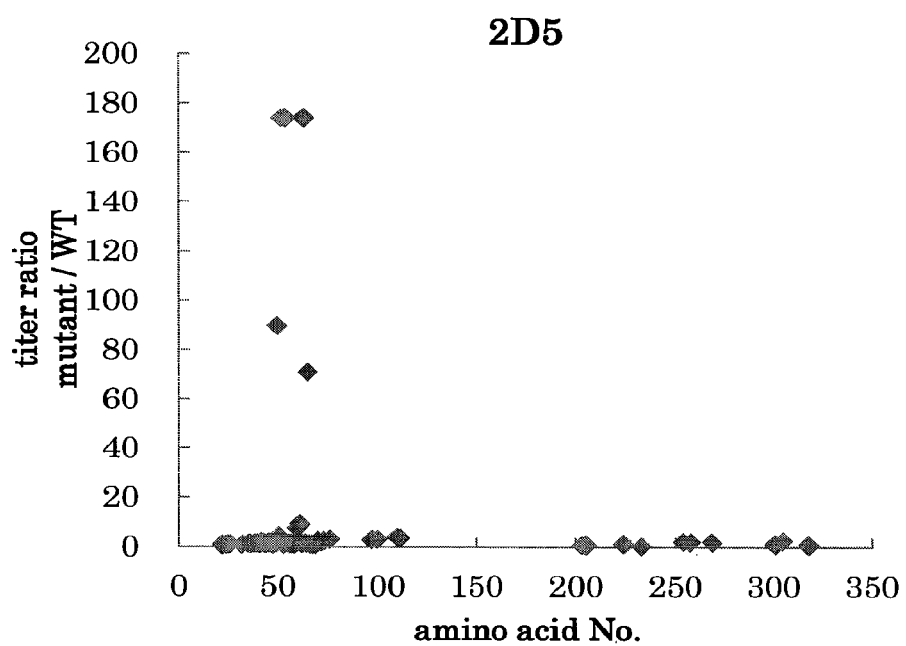
FIG. 7D shows binding activity of 2D5 antibody against baboon EL that was introduced mutation.
Figure 7E:
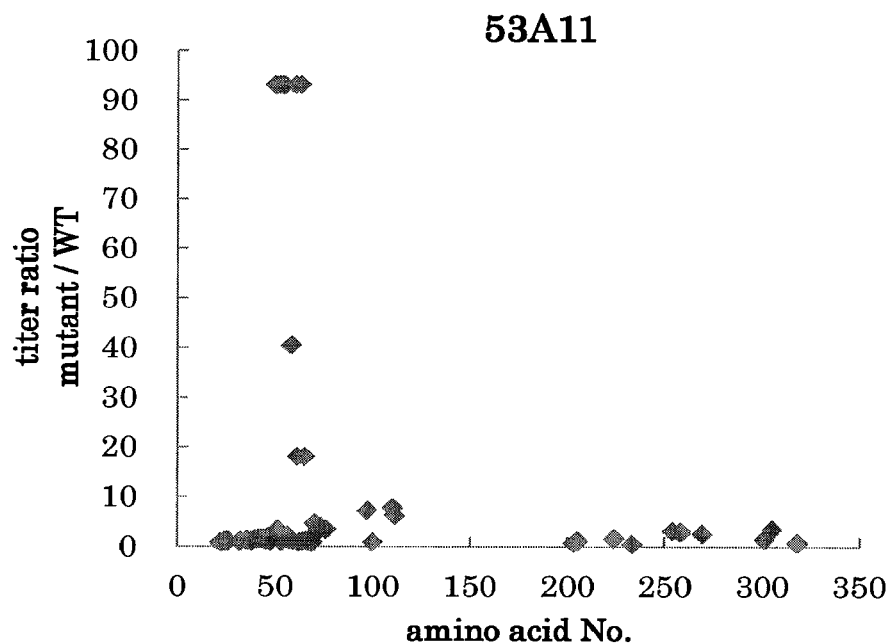
FIG. 7E shows binding activity of 53A11 antibody against baboon EL that was introduced mutation.
Figure 7F:
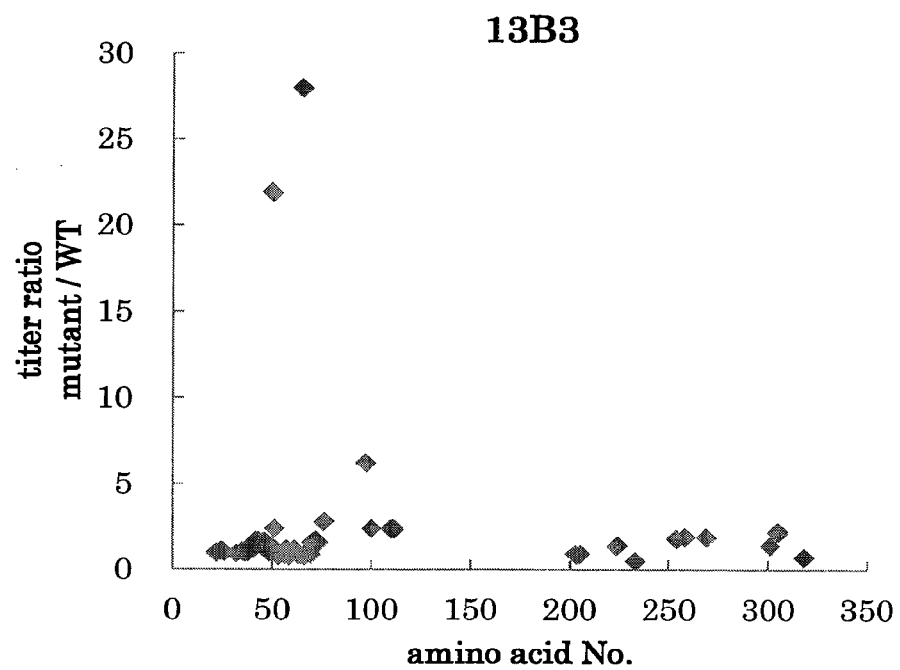
FIG. 7F shows binding activity of 13B3 antibody against baboon EL that was introduced mutation.
Figure 7G:
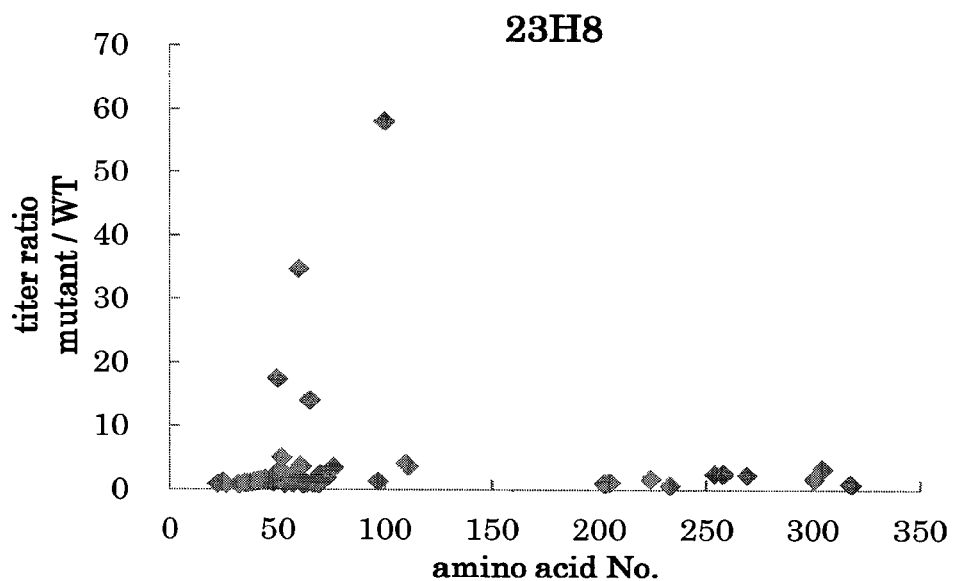
FIG. 7G shows binding activity of 23H8 antibody against baboon EL that was introduced mutation.
Figure 7H:
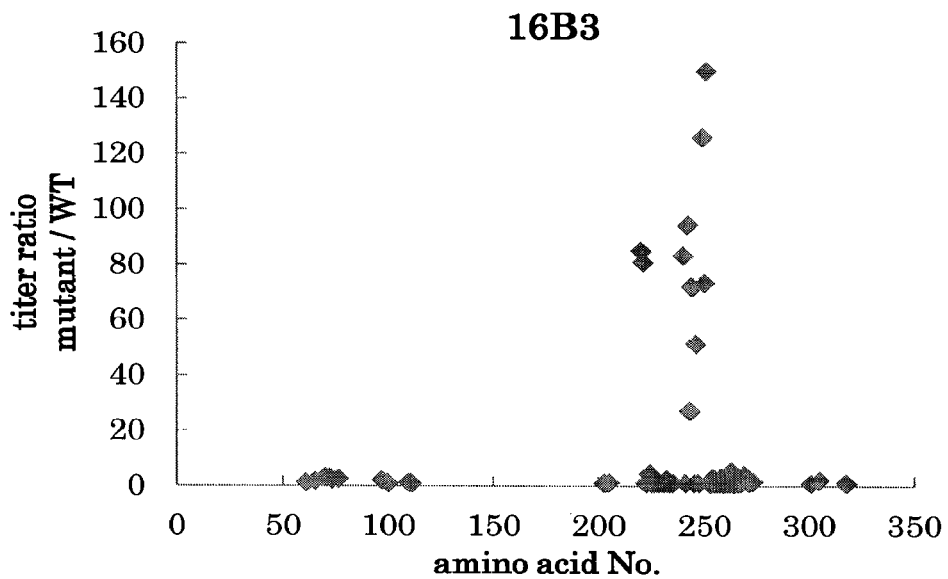
FIG. 7H shows binding activity of 16B3 antibody against baboon EL that was introduced mutation.
Figure 7I:
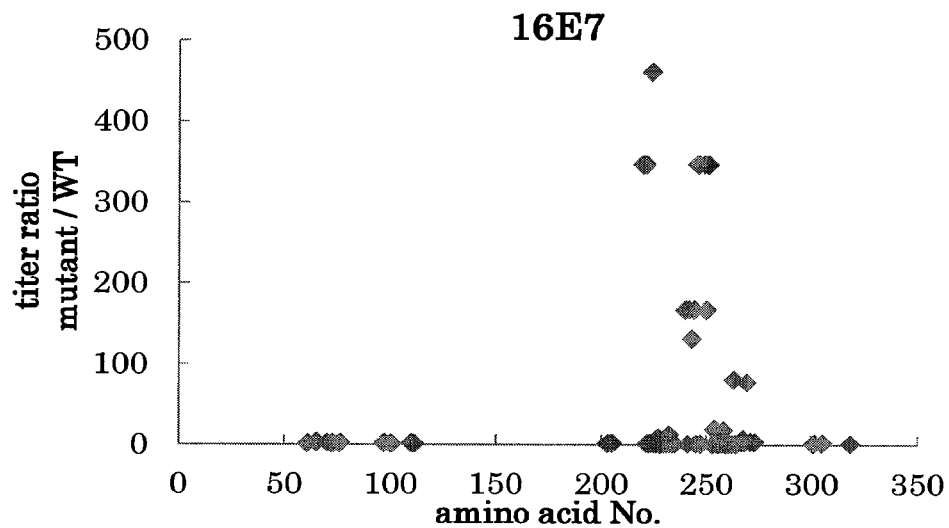
FIG. 7I shows binding activity of 16E7 antibody against baboon EL that was introduced mutation.
Figure 7J:
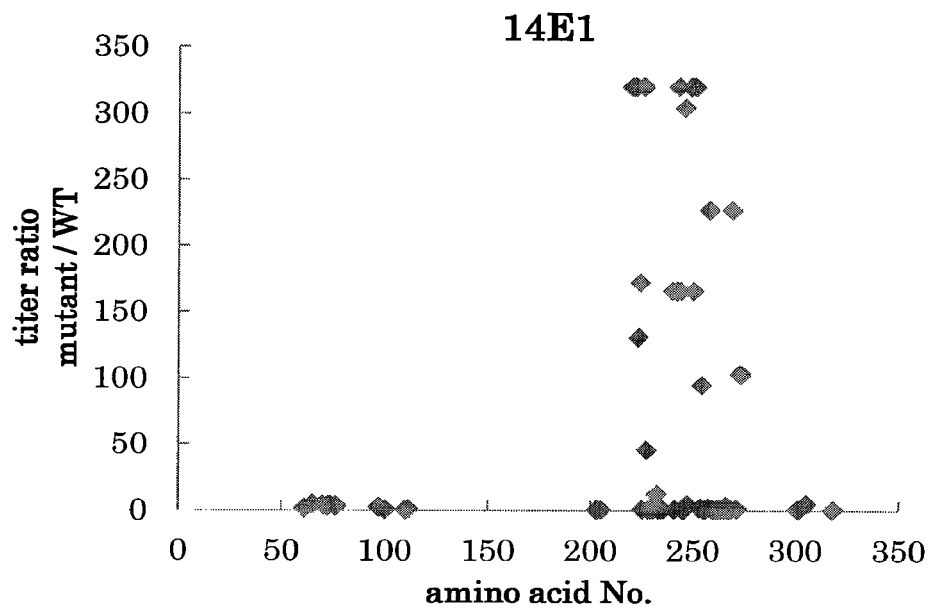
FIG. 7J shows binding activity of 14E1 antibody against baboon EL that was introduced mutation.
Figure 7K:
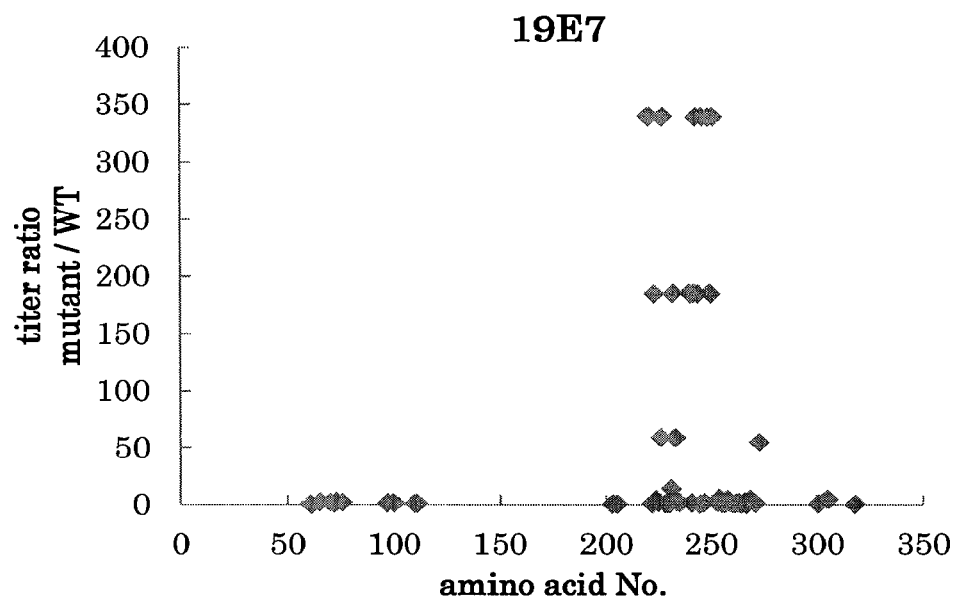
FIG. 7K shows binding activity of 19E7 antibody against baboon EL that was introduced mutation.

The EL region which contributes to antibody binding was determined by the homology-scanning mutagenesis or alanine scanning mutagenesis. The binding activity of anti-EL antibody to EL mutant was analyzed by ELISA. The amino acid residues of baboon EL were mutated to alanine using QuikChange Site-Directed Mutagenesis Kit (Agilent Technologies), but the amino acid residues which were different from baboon EL and mouse EL were mutated to mouse EL amino acid residues. Mutated EL heparin extracts were prepared and binding activity to anti-EL antibody according to Example 2 and Example 8. The relative effect of each mutation was evaluated from the following formula; ([antibody concentration where A450 value showed 1.0]-mutated EL)/([antibody concentration where A450 value showed 1.0]-wild type EL). The relative binding activity of mutated baboon EL to anti-EL antibodies (55A1, 7D4, 14A1, 2D5, 53A11, 13B3, 23H8, 16B3, 16E7, 14E1 and 19E7) was showed in FIG. 7A~L.

From the information of FIG. 7A-7G, it was shown that important amino acids in the binding of the 55A1, 7D4, 14A1, 2D5, 53A11, 13B3 or 23H8 antibody and EL are arginine at position 50, glutamic acid at position 60, histidine at position 61, tyrosine at position 65 and asparagine at position 100 in an amino acid sequence of SEQ ID NO: 1.

From the information of FIG. 7H-7K, it was shown that important amino acids in the binding of the 16B3, 16E7, 14E1 or 19E7 antibody and EL are histidine at position 220, threonine at position 221, tyrosine at position 222, threonine at position 223, arginine at position 224, phenylalanine at position 226, glycine at position 227, glycine at position 231, isoleucine at position 232, glutamine at position 233, methionine at position 234, aspartic acid at position 240, tyrosine at position 242, proline at position 243, asparagine at position 244, glycine at position 246, glutamine at position 249, proline at position 250, glycine at position 251, leucine at position 254, leucine at position 258, tyrosine at position 263, valine at position 269 and glutamic acid at position 273 in an amino acid sequence of SEQ ID NO: 1.

Example 12

Analysis of Amino Acid Sequence of Variable Region of Anti-EL Antibodies
The amino acid sequence of variable region of anti-EL antibody was determined using conventional procedure and described in FIG. 4A~L.

Example 13

Alignment of amino acid sequences of variable region of 55A1, 7D4, 2D5, 53A11, 13B3 and 23H8
The amino acid sequences of variable region of 55A1, 7D4, 2D5, 53A11, 13B3 and 23H8 were aligned by GENETYX software (FIG. 5A~D). FIGS. 5A and 5B indicated that all six CDRs of heavy and light chain of 55A1, 7D4, 14A1 and 2D5 had high similarity. FIG. 5C indicated that CDR1 and CDR2 of heavy chain of 53A11, 13B3 and 23H8 had high similarity.

The analysis of CDRs of heavy and light chain of 55A1, 7D4, 14A1 and 2D5 revealed the following things.

The amino acid sequences of heavy chain CDR1 was consisted of 5 amino acids, NYGMN (SEQ ID NO: 10).

The amino acid sequences of heavy chain CDR2 was consisted of 17 amino acids, WINTYSGVPTY (A or T) (G or D) DFKG (SEQ ID NO: 107).

The amino acid sequences of heavy chain CDR3 was consisted of 11 amino acids, (R or F) (G or S) YYGR (R or H) YFD (V or Y) (SEQ ID NO: 108).

The amino acid sequences of light chain CDR1 was consisted of 15 amino acids, KASQSVDYD (V or G) DSYM (H or N) (SEQ ID NO: 109).

The amino acid sequences of light chain CDR2 was consisted of 7 amino acids, AASNLXS (SEQ ID NO: 110). "X" represents given amino acid.

The amino acid sequences of light chain CDR3 was consisted of 10 amino acids, (H or Q) Q (T or S) (I or T or N) (E or D) DPP (- or W) T (SEQ ID NO: 111). "-" represents deletion of amino acid.

The analysis of CDRs of heavy and light chain of 53A11, 13B3 and 23H8 revealed the following things.

The amino acid sequences of heavy chain CDR1 was consisted of 5 amino acids, (D or E) (Y or N) T (M or I) H (SEQ ID NO: 112).

The amino acid sequences of heavy chain CDR2 was consisted of 17 amino acids, XINPYYGGTX (Y or N) NEKFKD (SEQ ID NO: 113). "X" represents given amino acid.

There was no commonality of amino acid residues in heavy chain CDR3.

Example 14

Alignment of Amino Acid Sequences of Variable Region of 16B3, 16E7, 14E1 and 19E7
The amino acid sequences of variable region of 16B3, 16E7, 14E1 and 19E7 were aligned by GENETYX software (FIG. 6A~D). FIGS. 6A and 6B indicated that all six CDRs of heavy and light chain of 16B3 and 16E7 had high similarity.

The analysis of CDRs of heavy and light chain of 16B3, 16E7, 14E1 and 19E7 revealed the following things.

The amino acid sequences of heavy chain CDR1 was consisted of 5 amino acids, (G or S) YTMS (SEQ ID NO: 114).

The amino acid sequences of heavy chain CDR2 was consisted of 17 amino acids, EISF (A or T) R (D or S) RAFYPDTVKG (SEQ ID NO: 115).

The amino acid sequences of heavy chain CDR3 was consisted of 13 amino acids, LGG (R or N) N (H or Y) DYWYFDV (SEQ ID NO: 116).

The amino acid sequences of light chain CDR1 was consisted of 15 amino acids, RASESVEYYGTSLMQ (SEQ ID NO: 70 or 78).

The amino acid sequences of light chain CDR2 was consisted of 7 amino acids, AASNVES (SEQ ID NO: 71 or 79).

The amino acid sequences of light chain CDR3 was consisted of 9 amino acids, QQSWKVPFT (SEQ ID NO: 72 or 80).

INDUSTRIAL APPLICABILITY

The monoclonal antibody which inhibits the enzymatic activity of vascular endothelial lipase of the present invention is useful as a drug for prevention and/or treatment of dyslipidemia, hyperlipidemia, arteriosclerosis, atherosclerosis, hypercholesterolemia, hypertriglyceridemia, diabetes, obesity and/or syndrome X because it has selectively inhibitory activity against vascular endothelial lipase.

Sequence List

```

The invention claimed is:

1. A monoclonal antibody that inhibits the enzymatic activity of vascular endothelial lipase or an antibody fragment thereof, wherein said antibody or fragment thereof recognizes at least four amino acid at positions of 50 to 100 in the amino acid sequence of SEQ ID NO: 1 including:
   1) tyrosine at position 65, and
   2) at least three amino acids selected from arginine at position 50, asparagine at position 52, arginine at position 54, aspartic acid at position 58, glutamic acid at position 60, histidine at position 61, glycine at position 63, and asparagine at position 100.

2. The monoclonal antibody or fragment thereof according to claim 1, wherein said antibody fragment is a Fab, F(ab')$_2$, Fab', scFv, dsFv or Diabody.

3. A pharmaceutical composition for treating or preventing a disease related to vascular endothelial lipase, comprising the monoclonal antibody of claim 1 or the antibody fragment thereof.

4. The pharmaceutical composition of claim 3, wherein the disease related to vascular endothelial lipase is dyslipidemia.

5. The monoclonal antibody or fragment thereof according to claim 1, wherein the monoclonal antibody or fragment thereof has a heavy chain variable region comprising amino acid sequence SEQ ID NO: 9, and a light chain variable region comprising amino acid sequence SEQ ID NO: 13.

6. The monoclonal antibody or fragment thereof according to claim 1, wherein said antibody or fragment thereof recognizes at least tyrosine at position 65, asparagine at position 52, arginine at position 54, glutamic acid at position 60, glycine at position 63, and asparagine at position 100 in the amino acid sequence of SEQ ID NO: 1.

7. The monoclonal antibody or fragment thereof according to claim 1, wherein said antibody or fragment thereof recognizes at least tyrosine at position 65, asparagine at position 52, glycine at position 63, and asparagine at position 100 in the amino acid sequence of SEQ ID NO: 1.

8. The monoclonal antibody or fragment thereof according to claim 1, wherein said antibody or fragment thereof recognizes at least tyrosine at position 65, arginine at position 54, glycine at position 63, and asparagine at position 100 in the amino acid sequence of SEQ ID NO: 1.

9. The monoclonal antibody or fragment thereof according to claim 1, wherein said antibody or fragment thereof recognizes at least tyrosine at position 65, glutamic acid at position 60, glycine at position 63, and asparagine at position 100 in the amino acid sequence of SEQ ID NO: 1.

* * * * *

                       SEQUENCE LISTING

<160> NUMBER OF SEQ ID NOS: 116

<210> SEQ ID NO 1
<211> LENGTH: 500
<212> TYPE: PRT
<213> ORGANISM: Homo sapiens
<220> FEATURE:
<221> NAME/KEY: PROTEIN
<222> LOCATION: (1)..(500)

<400> SEQUENCE: 1
```

Met Ser Asn Ser Val Pro Leu Leu Cys Phe Trp Ser Leu Cys Tyr Cys
1               5                   10                  15

Phe Ala Ala Gly Ser Pro Val Pro Phe Gly Pro Glu Gly Arg Leu Glu
            20                  25                  30

Asp Lys Leu His Lys Pro Lys Ala Thr Gln Thr Glu Val Lys Pro Ser
        35                  40                  45

Val Arg Phe Asn Leu Arg Thr Ser Lys Asp Pro Glu His Glu Gly Cys
    50                  55                  60

Tyr Leu Ser Val Gly His Ser Gln Pro Leu Glu Asp Cys Ser Phe Asn
65                  70                  75                  80

Met Thr Ala Lys Thr Phe Phe Ile Ile His Gly Trp Thr Met Ser Gly
                85                  90                  95

Ile Phe Glu Asn Trp Leu His Lys Leu Val Ser Ala Leu His Thr Arg
            100                 105                 110

Glu Lys Asp Ala Asn Val Val Val Asp Trp Leu Pro Leu Ala His
        115                 120                 125

Gln Leu Tyr Thr Asp Ala Val Asn Asn Thr Arg Val Val Gly His Ser
    130                 135                 140

Ile Ala Arg Met Leu Asp Trp Leu Gln Glu Lys Asp Asp Phe Ser Leu
145                 150                 155                 160

Gly Asn Val His Leu Ile Gly Tyr Ser Leu Gly Ala His Val Ala Gly
                165                 170                 175

Tyr Ala Gly Asn Phe Val Lys Gly Thr Val Gly Arg Ile Thr Gly Leu
            180                 185                 190

Asp Pro Ala Gly Pro Met Phe Glu Gly Ala Asp Ile His Lys Arg Leu
        195                 200                 205

Ser Pro Asp Asp Ala Asp Phe Val Asp Val Leu His Thr Tyr Thr Arg
    210                 215                 220

Ser Phe Gly Leu Ser Ile Gly Ile Gln Met Pro Val Gly His Ile Asp
225                 230                 235                 240

Ile Tyr Pro Asn Gly Gly Asp Phe Gln Pro Gly Cys Gly Leu Asn Asp
                245                 250                 255

Val Leu Gly Ser Ile Ala Tyr Gly Thr Ile Thr Glu Val Val Lys Cys
            260                 265                 270

Glu His Glu Arg Ala Val His Leu Phe Val Asp Ser Leu Val Asn Gln
        275                 280                 285

Asp Lys Pro Ser Phe Ala Phe Gln Cys Thr Asp Ser Asn Arg Phe Lys
    290                 295                 300

Lys Gly Ile Cys Leu Ser Cys Arg Lys Asn Arg Cys Asn Ser Ile Gly
305                 310                 315                 320

Tyr Asn Ala Lys Lys Met Arg Asn Lys Arg Asn Ser Lys Met Tyr Leu
                325                 330                 335

Lys Thr Arg Ala Gly Met Pro Phe Arg Val Tyr His Tyr Gln Met Lys

```
                340                 345                 350
Ile His Val Phe Ser Tyr Lys Asn Met Gly Glu Ile Glu Pro Thr Phe
            355                 360                 365

Tyr Val Thr Leu Tyr Gly Thr Asn Ala Asp Ser Gln Thr Leu Pro Leu
    370                 375                 380

Glu Ile Val Glu Arg Ile Glu Gln Asn Ala Thr Asn Thr Phe Leu Val
385                 390                 395                 400

Tyr Thr Glu Glu Asp Leu Gly Asp Leu Leu Lys Ile Gln Leu Thr Trp
                405                 410                 415

Glu Gly Ala Ser Gln Ser Trp Tyr Asn Leu Trp Lys Glu Phe Arg Ser
            420                 425                 430

Tyr Leu Ser Gln Pro Arg Asn Pro Gly Arg Glu Leu Asn Ile Arg Arg
    435                 440                 445

Ile Arg Val Lys Ser Gly Glu Thr Gln Arg Lys Leu Thr Phe Cys Thr
450                 455                 460

Glu Asp Pro Glu Asn Thr Ser Ile Ser Pro Gly Arg Glu Leu Trp Phe
                470                 475                 480
465

Arg Lys Cys Arg Asp Gly Trp Arg Met Lys Asn Glu Thr Ser Pro Thr
            485                 490                 495

Val Glu Leu Pro
            500

<210> SEQ ID NO 2
<211> LENGTH: 519
<212> TYPE: PRT
<213> ORGANISM: Unknown
<220> FEATURE:
<223> OTHER INFORMATION: Baboon
<220> FEATURE:
<221> NAME/KEY: PROTEIN
<222> LOCATION: (1)..(519)

<400> SEQUENCE: 2

Met Ser Asn Ser Val Pro Leu Leu Cys Phe Trp Ser Leu Cys Cys Cys
1               5                   10                  15

Phe Ala Ala Gly Ser Pro Thr Pro Phe Gly Pro Glu Gly Gln Leu Glu
            20                  25                  30

Asp Glu Leu His Lys Pro Lys Ala Ile Gln Thr Glu Val Lys Pro Ser
        35                  40                  45

Val Arg Phe Asn Leu Arg Thr Ser Lys Asp Pro Glu His Glu Gly Cys
    50                  55                  60

Tyr Leu Ser Leu Gly His Ser Gln Pro Leu Glu Asp Cys Gly Phe Asn
65                  70                  75                  80

Met Thr Ala Lys Thr Phe Phe Ile Ile His Gly Trp Thr Met Ser Gly
                85                  90                  95

Ile Phe Glu Asn Trp Leu His Lys Leu Val Ser Ala Leu His Thr Arg
            100                 105                 110

Glu Lys Asp Ala Asn Val Val Val Asp Trp Leu Pro Leu Ala His
        115                 120                 125

Gln Leu Tyr Thr Asp Ala Val Asn Asn Thr Arg Val Val Gly His Ser
    130                 135                 140

Ile Ala Arg Met Leu Asp Trp Leu Gln Glu Lys Asp Asp Phe Ser Leu
145                 150                 155                 160

Glu Asn Val His Leu Ile Gly Tyr Ser Leu Gly Ala His Val Ala Gly
                165                 170                 175

Tyr Ala Gly Asn Phe Val Lys Gly Thr Val Gly Arg Ile Thr Gly Leu
```

```
                 180                 185                 190
Asp Pro Ala Gly Pro Met Phe Glu Gly Ala Asp Ile His Lys Arg Leu
            195                 200                 205
Ser Pro Asp Ala Asp Phe Val Asp Val Leu His Thr Tyr Thr Arg
        210                 215                 220
Ser Phe Gly Leu Ser Ile Gly Ile Gln Met Pro Val Gly His Ile Asp
225                 230                 235                 240
Ile Tyr Pro Asn Gly Gly Asp Phe Gln Pro Gly Cys Gly Leu Asn Asp
                245                 250                 255
Val Leu Gly Ser Met Ala Tyr Gly Thr Ile Thr Glu Val Val Lys Cys
            260                 265                 270
Glu His Glu Arg Ala Val His Leu Phe Val Asp Ser Leu Val Asn Gln
        275                 280                 285
Asp Lys Pro Ser Phe Ala Phe Gln Cys Thr Asp Ser Asn Arg Phe Lys
    290                 295                 300
Lys Gly Ile Cys Leu Ser Cys Arg Lys Asn Arg Cys Asn Ser Ile Gly
305                 310                 315                 320
Tyr Asn Ala Lys Lys Met Arg Asn Lys Arg Asn Ser Lys Met Tyr Leu
                325                 330                 335
Lys Thr Arg Ala Gly Met Pro Phe Arg Val Tyr His Tyr Gln Met Lys
            340                 345                 350
Ile His Val Phe Ser Tyr Lys Asn Met Gly Glu Ile Glu Pro Thr Phe
        355                 360                 365
Tyr Val Thr Leu Tyr Gly Thr Asn Ala Asp Ser Gln Thr Leu Pro Leu
    370                 375                 380
Glu Ile Val Glu Arg Ile Glu Gln Asn Ala Thr Asn Thr Phe Leu Val
385                 390                 395                 400
Tyr Thr Glu Glu Asp Leu Gly Asp Leu Leu Lys Ile Gln Leu Thr Trp
                405                 410                 415
Glu Gly Ala Ser Gln Ser Trp Tyr Asn Leu Trp Lys Glu Leu Arg Ser
            420                 425                 430
Tyr Leu Ser Gln Pro His Asn Pro Gly Arg Glu Leu Asn Ile Arg Arg
        435                 440                 445
Ile Arg Val Lys Ser Gly Glu Thr Gln Arg Lys Leu Thr Phe Cys Ala
    450                 455                 460
Glu Asp Pro Glu Asn Thr Ser Ile Ser Pro Gly Arg Glu Leu Trp Phe
465                 470                 475                 480
Arg Lys Cys Arg Asp Gly Trp Arg Met Lys Asn Glu Thr Ser Pro Thr
                485                 490                 495
Val Glu Leu Pro Gly Glu Pro Gly Asp Asp Gly Pro Ser Gly Ala Glu
            500                 505                 510
Gly Pro Pro Gly Pro Gln Gly
        515

<210> SEQ ID NO 3
<211> LENGTH: 519
<212> TYPE: PRT
<213> ORGANISM: Unknown
<220> FEATURE:
<223> OTHER INFORMATION: Cynomolgus
<220> FEATURE:
<221> NAME/KEY: PROTEIN
<222> LOCATION: (1)..(519)

<400> SEQUENCE: 3

Met Ser Asn Ser Val Pro Leu Leu Cys Phe Trp Ser Leu Cys Cys Cys
```

-continued

```
1               5                   10                  15
Phe Ala Ala Gly Ser Pro Thr Pro Phe Gly Pro Glu Gly Gln Leu Ala
            20                  25                  30
Asp Glu Leu His Lys Pro Lys Ala Ile Gln Thr Glu Val Lys Pro Ser
            35                  40                  45
Val Arg Phe Asn Leu Arg Thr Ser Lys Asp Pro Glu His Glu Gly Cys
            50                  55                  60
Tyr Leu Ser Leu Gly His Ser Gln Pro Leu Glu Asp Cys Gly Phe Asn
65                  70                  75                  80
Met Thr Ala Lys Thr Phe Phe Ile Ile His Gly Trp Thr Met Ser Gly
                85                  90                  95
Ile Phe Glu Asn Trp Leu His Lys Leu Val Ser Ala Leu His Thr Arg
                100                 105                 110
Glu Lys Asp Ala Asn Val Val Val Asp Trp Leu Pro Leu Ala His
                115                 120                 125
Gln Leu Tyr Thr Asp Ala Val Asn Asn Thr Arg Val Val Gly His Ser
            130                 135                 140
Ile Ala Arg Met Leu Asp Trp Leu Gln Glu Lys Asp Asp Phe Ser Leu
145                 150                 155                 160
Gly Asn Val His Leu Ile Gly Tyr Ser Leu Gly Ala His Val Ala Gly
                165                 170                 175
Tyr Ala Gly Asn Phe Val Lys Gly Thr Val Gly Arg Ile Thr Gly Leu
                180                 185                 190
Asp Pro Ala Gly Pro Met Phe Glu Gly Ala Asp Ile His Lys Arg Leu
            195                 200                 205
Ser Pro Asp Asp Ala Asp Phe Val Asp Val Leu His Thr Tyr Thr Arg
210                 215                 220
Ser Phe Gly Leu Ser Ile Gly Ile Gln Met Pro Val Gly His Ile Asp
225                 230                 235                 240
Ile Tyr Pro Asn Gly Gly Asp Phe Gln Pro Gly Cys Gly Leu Asn Asp
                245                 250                 255
Val Leu Gly Ser Met Ala Tyr Gly Thr Ile Thr Glu Val Val Lys Cys
            260                 265                 270
Glu His Glu Arg Ala Val His Leu Phe Val Asp Ser Leu Val Asn Gln
            275                 280                 285
Asp Lys Pro Ser Phe Ala Phe Gln Cys Thr Asp Ser Asn Arg Phe Lys
            290                 295                 300
Lys Gly Ile Cys Leu Ser Cys Arg Lys Asn Arg Cys Asn Ser Ile Gly
305                 310                 315                 320
Tyr Asn Ala Lys Lys Met Arg Asn Lys Arg Asn Ser Lys Met Tyr Leu
                325                 330                 335
Lys Thr Arg Ala Gly Met Pro Phe Arg Val Tyr His Tyr Gln Met Lys
                340                 345                 350
Ile His Val Phe Ser Tyr Lys Asn Met Gly Glu Ile Glu Pro Thr Phe
            355                 360                 365
Tyr Val Thr Leu Tyr Gly Thr Asn Ala Asp Ser Gln Thr Leu Pro Leu
            370                 375                 380
Glu Ile Val Glu Arg Ile Glu Gln Asn Ala Thr Asn Thr Phe Leu Val
385                 390                 395                 400
Tyr Thr Glu Glu Asp Leu Gly Asp Leu Leu Lys Ile Gln Leu Thr Trp
                405                 410                 415
Glu Gly Ala Ser Gln Ser Trp Tyr Asn Leu Trp Lys Glu Leu Arg Ser
            420                 425                 430
```

Tyr Leu Ser Gln Pro His Asn Pro Gly Arg Glu Leu Asn Ile Arg Arg
        435                 440                 445

Ile Arg Val Lys Ser Gly Glu Thr Gln Arg Lys Leu Thr Phe Cys Ala
    450                 455                 460

Glu Asp Pro Glu Asn Thr Ser Ile Ser Pro Gly Arg Glu Leu Trp Phe
465                 470                 475                 480

Arg Lys Cys Arg Asp Gly Trp Arg Met Lys Asn Glu Thr Ser Pro Thr
                485                 490                 495

Val Glu Leu Pro Gly Glu Pro Gly Asp Asp Gly Pro Ser Gly Ala Glu
            500                 505                 510

Gly Pro Pro Gly Pro Gln Gly
            515

<210> SEQ ID NO 4
<211> LENGTH: 519
<212> TYPE: PRT
<213> ORGANISM: Artificial Sequence
<220> FEATURE:
<223> OTHER INFORMATION: Synthetic: chimera
<220> FEATURE:
<221> NAME/KEY: PROTEIN
<222> LOCATION: (1)..(519)

<400> SEQUENCE: 4

Met Ser Asn Ser Val Pro Leu Leu Cys Phe Trp Ser Leu Cys Tyr Cys
1               5                   10                  15

Phe Ala Ala Gly Ser Pro Val Pro Phe Gly Pro Glu Gly Arg Leu Glu
                20                  25                  30

Asp Lys Leu His Lys Pro Lys Ala Thr Gln Thr Glu Val Lys Pro Ser
            35                  40                  45

Val Arg Phe Asn Leu Arg Thr Ser Lys Asp Pro Glu His Glu Gly Cys
    50                  55                  60

Tyr Leu Ser Val Gly His Ser Gln Pro Leu Glu Asp Cys Ser Phe Asn
65                  70                  75                  80

Met Thr Ala Lys Thr Phe Phe Ile Ile His Gly Trp Thr Met Ser Gly
                85                  90                  95

Ile Phe Glu Asn Trp Leu His Lys Leu Val Ser Ala Leu His Thr Arg
                100                 105                 110

Glu Lys Asp Ala Asn Val Val Val Asp Trp Leu Pro Leu Ala His
            115                 120                 125

Gln Leu Tyr Thr Asp Ala Val Asn Asn Thr Arg Val Val Gly His Ser
    130                 135                 140

Ile Ala Arg Met Leu Asp Trp Leu Gln Glu Lys Asp Asp Phe Ser Leu
145                 150                 155                 160

Gly Asn Val His Leu Ile Gly Tyr Ser Leu Gly Ala His Val Ala Gly
                165                 170                 175

Tyr Ala Gly Asn Phe Val Lys Gly Thr Val Gly Arg Ile Thr Gly Leu
                180                 185                 190

Asp Pro Ala Gly Pro Met Phe Glu Gly Val Asp Ile Asn Arg Arg Leu
            195                 200                 205

Ser Pro Asp Asp Ala Asp Phe Val Asp Val Leu His Thr Tyr Thr Leu
    210                 215                 220

Ser Phe Gly Leu Ser Ile Gly Ile Arg Met Pro Val Gly His Ile Asp
225                 230                 235                 240

Ile Tyr Pro Asn Gly Gly Asp Phe Gln Pro Gly Cys Gly Phe Asn Asp
                245                 250                 255

```
Val Ile Gly Ser Phe Ala Tyr Gly Thr Ile Ser Glu Met Val Lys Cys
            260                 265                 270

Glu His Glu Arg Ala Val His Leu Phe Val Asp Ser Leu Val Asn Gln
            275                 280                 285

Asp Lys Pro Ser Phe Ala Phe Gln Cys Thr Asp Ser Ser Arg Phe Lys
            290                 295                 300

Arg Gly Ile Cys Leu Ser Cys Arg Lys Asn Arg Cys Asn Asn Ile Gly
305                 310                 315                 320

Tyr Asn Ala Lys Lys Met Arg Lys Arg Asn Ser Lys Met Tyr Leu
                325                 330                 335

Lys Thr Arg Ala Gly Met Pro Phe Lys Val Tyr His Tyr Gln Leu Lys
            340                 345                 350

Val His Met Phe Ser Tyr Asn Asn Ser Gly Asp Thr Gln Pro Thr Leu
            355                 360                 365

Tyr Ile Thr Leu Tyr Gly Ser Asn Ala Asp Ser Gln Asn Leu Pro Leu
            370                 375                 380

Glu Ile Val Glu Lys Ile Glu Leu Asn Ala Thr Asn Thr Phe Leu Val
385                 390                 395                 400

Tyr Thr Glu Glu Asp Leu Gly Asp Leu Leu Lys Met Arg Leu Thr Trp
                405                 410                 415

Glu Gly Val Ala His Ser Trp Tyr Asn Leu Trp Asn Glu Phe Arg Asn
            420                 425                 430

Tyr Leu Ser Gln Pro Ser Asn Pro Ser Arg Glu Leu Tyr Ile Arg Arg
            435                 440                 445

Ile Arg Val Lys Ser Gly Glu Thr Gln Arg Lys Val Thr Phe Cys Thr
450                 455                 460

Gln Asp Pro Thr Lys Ser Ser Ile Ser Pro Gly Gln Glu Leu Trp Phe
465                 470                 475                 480

His Lys Cys Gln Asp Gly Trp Lys Met Lys Asn Lys Thr Ser Pro Phe
                485                 490                 495

Val Asn Leu Ala Gly Glu Pro Gly Asp Asp Gly Pro Ser Gly Ala Glu
            500                 505                 510

Gly Pro Pro Gly Pro Gln Gly
            515

<210> SEQ ID NO 5
<211> LENGTH: 519
<212> TYPE: PRT
<213> ORGANISM: Artificial Sequence
<220> FEATURE:
<223> OTHER INFORMATION: Synthetic: chimera
<220> FEATURE:
<221> NAME/KEY: PROTEIN
<222> LOCATION: (1)..(519)

<400> SEQUENCE: 5

Met Ser Asn Ser Val Pro Leu Leu Cys Phe Trp Ser Leu Cys Tyr Cys
1               5                   10                  15

Phe Ala Ala Gly Ser Pro Val Pro Phe Gly Pro Glu Gly Arg Leu Glu
            20                  25                  30

Asp Lys Leu His Lys Pro Lys Ala Thr Gln Thr Glu Val Lys Pro Ser
            35                  40                  45

Val Arg Phe Asn Leu Arg Thr Ser Lys Asp Pro Glu Gln Glu Gly Cys
        50                  55                  60

Asn Leu Ser Leu Gly Asp Ser Lys Leu Leu Glu Asn Cys Gly Phe Asn
65                  70                  75                  80
```

```
Met Thr Ala Lys Thr Phe Phe Ile Ile His Gly Trp Thr Met Ser Gly
                85                  90                  95
Met Phe Glu Ser Trp Leu His Lys Leu Val Ser Ala Leu Gln Met Arg
               100                 105                 110
Glu Lys Asp Ala Asn Val Val Val Asp Trp Leu Pro Leu Ala His
           115                 120                 125
Gln Leu Tyr Thr Asp Ala Val Asn Asn Thr Arg Val Val Gly Gln Arg
           130                 135                 140
Val Ala Gly Met Leu Asp Trp Leu Gln Glu Lys Glu Glu Phe Ser Leu
145                 150                 155                 160
Gly Asn Val His Leu Ile Gly Tyr Ser Leu Gly Ala His Val Ala Gly
               165                 170                 175
Tyr Ala Gly Asn Phe Val Lys Gly Thr Val Gly Arg Ile Thr Gly Leu
           180                 185                 190
Asp Pro Ala Gly Pro Met Phe Glu Gly Val Asp Ile Asn Arg Arg Leu
           195                 200                 205
Ser Pro Asp Asp Ala Asp Phe Val Asp Val Leu His Thr Tyr Thr Leu
       210                 215                 220
Ser Phe Gly Leu Ser Ile Gly Ile Arg Met Pro Val Gly His Ile Asp
225                 230                 235                 240
Ile Tyr Pro Asn Gly Gly Asp Phe Gln Pro Gly Cys Gly Phe Asn Asp
               245                 250                 255
Val Ile Gly Ser Phe Ala Tyr Gly Thr Ile Ser Glu Met Val Lys Cys
           260                 265                 270
Glu His Glu Arg Ala Val His Leu Phe Val Asp Ser Leu Val Asn Gln
       275                 280                 285
Asp Lys Pro Ser Phe Ala Phe Gln Cys Thr Asp Ser Ser Arg Phe Lys
       290                 295                 300
Arg Gly Ile Cys Leu Ser Cys Arg Lys Asn Arg Cys Asn Asn Ile Gly
305                 310                 315                 320
Tyr Asn Ala Lys Lys Met Arg Lys Lys Arg Asn Ser Lys Met Tyr Leu
               325                 330                 335
Lys Thr Arg Ala Gly Met Pro Phe Lys Val Tyr His Tyr Gln Leu Lys
           340                 345                 350
Val His Met Phe Ser Tyr Asn Asn Ser Gly Asp Thr Gln Pro Thr Leu
       355                 360                 365
Tyr Ile Thr Leu Tyr Gly Ser Asn Ala Asp Ser Gln Asn Leu Pro Leu
       370                 375                 380
Glu Ile Val Glu Lys Ile Glu Leu Asn Ala Thr Asn Thr Phe Leu Val
385                 390                 395                 400
Tyr Thr Glu Glu Asp Leu Gly Asp Leu Leu Lys Met Arg Leu Thr Trp
               405                 410                 415
Glu Gly Val Ala His Ser Trp Tyr Asn Leu Trp Asn Glu Phe Arg Asn
           420                 425                 430
Tyr Leu Ser Gln Pro Ser Asn Pro Ser Arg Glu Leu Tyr Ile Arg Arg
       435                 440                 445
Ile Arg Val Lys Ser Gly Glu Thr Gln Arg Leu Val Thr Phe Cys Thr
       450                 455                 460
Gln Asp Pro Thr Lys Ser Ser Ile Ser Pro Gly Gln Glu Leu Trp Phe
465                 470                 475                 480
His Lys Cys Gln Asp Gly Trp Lys Met Lys Asn Lys Thr Ser Pro Phe
               485                 490                 495
```

```
Val Asn Leu Ala Gly Glu Pro Gly Asp Gly Pro Ser Gly Ala Glu
            500                 505                 510
Gly Pro Pro Gly Pro Gln Gly
        515

<210> SEQ ID NO 6
<211> LENGTH: 519
<212> TYPE: PRT
<213> ORGANISM: Artificial Sequence
<220> FEATURE:
<223> OTHER INFORMATION: Synthetic: chimera
<220> FEATURE:
<221> NAME/KEY: PROTEIN
<222> LOCATION: (1)..(519)

<400> SEQUENCE: 6

Met Arg Asn Thr Val Phe Leu Leu Gly Phe Trp Ser Val Tyr Cys Tyr
1               5                   10                  15

Phe Pro Ala Gly Ser Ile Thr Thr Leu Arg Pro Glu Gly Ser Leu Arg
            20                  25                  30

Asp Glu His His Lys Pro Thr Gly Val Pro Ala Thr Ala Arg Pro Ser
        35                  40                  45

Val Ala Phe Asn Ile Arg Thr Ser Lys Asp Pro Glu His Glu Gly Cys
    50                  55                  60

Tyr Leu Ser Val Gly His Ser Gln Pro Leu Glu Asp Cys Ser Phe Asn
65                  70                  75                  80

Met Thr Ala Lys Thr Phe Phe Ile Ile His Gly Trp Thr Met Ser Gly
                85                  90                  95

Ile Phe Glu Asn Trp Leu His Lys Leu Val Ser Ala Leu His Thr Arg
            100                 105                 110

Glu Lys Asp Ala Asn Val Val Val Asp Trp Leu Pro Leu Ala His
        115                 120                 125

Gln Leu Tyr Thr Asp Ala Val Asn Asn Thr Arg Val Val Gly Gln Arg
    130                 135                 140

Val Ala Gly Met Leu Asp Trp Leu Gln Glu Lys Glu Glu Phe Ser Leu
145                 150                 155                 160

Gly Asn Val His Leu Ile Gly Tyr Ser Leu Gly Ala His Val Ala Gly
                165                 170                 175

Tyr Ala Gly Asn Phe Val Lys Gly Thr Val Gly Arg Ile Thr Gly Leu
            180                 185                 190

Asp Pro Ala Gly Pro Met Phe Glu Gly Val Asp Ile Asn Arg Arg Leu
        195                 200                 205

Ser Pro Asp Asp Ala Asp Phe Val Asp Val Leu His Thr Tyr Thr Leu
    210                 215                 220

Ser Phe Gly Leu Ser Ile Gly Ile Arg Met Pro Val Gly His Ile Asp
225                 230                 235                 240

Ile Tyr Pro Asn Gly Gly Asp Phe Gln Pro Gly Cys Gly Phe Asn Asp
                245                 250                 255

Val Ile Gly Ser Phe Ala Tyr Gly Thr Ile Ser Glu Met Val Lys Cys
            260                 265                 270

Glu His Glu Arg Ala Val His Leu Phe Val Asp Ser Leu Val Asn Gln
        275                 280                 285

Asp Lys Pro Ser Phe Ala Phe Gln Cys Thr Asp Ser Ser Arg Phe Lys
    290                 295                 300

Arg Gly Ile Cys Leu Ser Cys Arg Lys Asn Arg Cys Asn Asn Ile Gly
305                 310                 315                 320
```

-continued

Tyr Asn Ala Lys Lys Met Arg Lys Lys Arg Asn Ser Lys Met Tyr Leu
                325                 330                 335
Lys Thr Arg Ala Gly Met Pro Phe Lys Val Tyr His Tyr Gln Leu Lys
            340                 345                 350
Val His Met Phe Ser Tyr Asn Asn Ser Gly Asp Thr Gln Pro Thr Leu
        355                 360                 365
Tyr Ile Thr Leu Tyr Gly Ser Asn Ala Asp Ser Gln Asn Leu Pro Leu
    370                 375                 380
Glu Ile Val Glu Lys Ile Glu Leu Asn Ala Thr Asn Thr Phe Leu Val
385                 390                 395                 400
Tyr Thr Glu Glu Asp Leu Gly Asp Leu Leu Lys Met Arg Leu Thr Trp
                405                 410                 415
Glu Gly Val Ala His Ser Trp Tyr Asn Leu Trp Asn Glu Phe Arg Asn
            420                 425                 430
Tyr Leu Ser Gln Pro Ser Asn Pro Ser Arg Glu Leu Tyr Ile Arg Arg
        435                 440                 445
Ile Arg Val Lys Ser Gly Glu Thr Gln Arg Lys Val Thr Phe Cys Thr
    450                 455                 460
Gln Asp Pro Thr Lys Ser Ser Ile Ser Pro Gly Gln Glu Leu Trp Phe
465                 470                 475                 480
His Lys Cys Gln Asp Gly Trp Lys Met Lys Asn Lys Thr Ser Pro Phe
                485                 490                 495
Val Asn Leu Ala Gly Glu Pro Gly Asp Asp Gly Pro Ser Gly Ala Glu
            500                 505                 510
Gly Pro Pro Gly Pro Gln Gly
        515

<210> SEQ ID NO 7
<211> LENGTH: 519
<212> TYPE: PRT
<213> ORGANISM: Unknown
<220> FEATURE:
<223> OTHER INFORMATION: Rabbit
<220> FEATURE:
<221> NAME/KEY: PROTEIN
<222> LOCATION: (1)..(519)

<400> SEQUENCE: 7

Met Arg Arg Ser Ile Pro Leu Leu Cys Leu Trp Ser Ala Cys Tyr Cys
1               5                   10                  15
Leu Ala Ala Gly Ser Pro Ala Ala Leu Gly Ala Glu Glu Gln Leu Glu
            20                  25                  30
Gly Gly Leu Arg Thr Ala Lys Asp Gly Pro Ala Ala Lys Ala Ala
        35                  40                  45
Val Arg Phe His Leu Arg Thr Ser Lys Gly Pro Glu Arg Glu Gly Cys
    50                  55                  60
Tyr Leu Ser Val Gly His Ser Gln Pro Leu Glu Asp Cys Ser Phe Asn
65                  70                  75                  80
Met Thr Ala Lys Thr Phe Phe Ile Ile His Gly Trp Thr Met Ser Gly
                85                  90                  95
Met Leu Glu Asn Trp Leu His Lys Leu Val Ser Ala Leu Gln Met Arg
            100                 105                 110
Glu Lys Asp Ala Asn Val Val Val Asp Trp Leu Pro Leu Ala His
        115                 120                 125
Gln Leu Tyr Thr Asp Ala Val Asn Ser Thr Arg Val Val Gly Leu Ser
    130                 135                 140

Val Ala Lys Met Leu Asp Trp Leu Gln Gly Lys Asp Gly Phe Ser Leu
145                 150                 155                 160

Gly Asn Val His Leu Ile Gly Tyr Ser Leu Gly Ala His Val Ala Gly
            165                 170                 175

Phe Ala Gly Asn Phe Val Lys Gly Thr Val Gly Arg Ile Thr Gly Leu
        180                 185                 190

Asp Pro Ala Gly Pro Met Phe Glu Gly Val Asp Ile His Arg Arg Leu
    195                 200                 205

Ser Pro Asp Asp Ala Asp Phe Val Asp Val Leu His Thr Tyr Thr Arg
210                 215                 220

Ser Phe Gly Ile Ser Ile Gly Ile Gln Met Pro Val Gly His Ile Asp
225                 230                 235                 240

Ile Tyr Pro Asn Gly Gly Asp Phe Gln Pro Gly Cys Gly Leu Asn Asp
                245                 250                 255

Val Leu Gly Ser Ile Ala Tyr Gly Thr Ile Ala Glu Val Val Lys Cys
            260                 265                 270

Glu His Glu Arg Ala Val His Leu Phe Val Asp Ser Leu Val Asn Gln
        275                 280                 285

Asp Lys Pro Ser Phe Ala Phe Gln Cys Thr Asp Ser Asn Arg Phe Lys
    290                 295                 300

Lys Gly Ile Cys Leu Ser Cys Arg Lys Asn Arg Cys Asn Gly Ile Gly
305                 310                 315                 320

Tyr Asn Ala Lys Lys Thr Arg Asn Lys Arg Asn Thr Lys Met Tyr Leu
                325                 330                 335

Lys Thr Arg Ala Gly Met Pro Phe Arg Val Tyr His Tyr Gln Met Lys
            340                 345                 350

Ile His Phe Phe Ser Tyr Lys Ser Val Gly Ala Ile Glu Pro Thr Phe
        355                 360                 365

Tyr Val Thr Leu Tyr Gly Thr Asn Ala Glu Ser Gln Val Leu Ser Leu
    370                 375                 380

Glu Ile Val Glu Gln Ile Gly Leu Asn Ala Thr Asn Thr Phe Leu Val
385                 390                 395                 400

Tyr Thr Glu Glu Asp Leu Gly Asp Leu Leu Lys Ile Lys Leu Thr Trp
                405                 410                 415

Glu Gly Thr Ser Arg Ser Trp Tyr Asp Leu Trp Arg Glu Phe Arg Ser
            420                 425                 430

Tyr Leu Ser Gln Pro His Arg Pro Glu Arg Glu Leu Ser Ile Arg Arg
        435                 440                 445

Ile Arg Val Lys Ser Gly Glu Thr Gln Arg Arg Leu Thr Phe Cys Val
    450                 455                 460

Glu Asp Pro Glu Lys Thr Ser Ile Ala Pro Gly Gln Glu Leu Trp Phe
465                 470                 475                 480

Tyr Lys Cys Arg Asp Gly Trp Arg Met Lys Asn Glu Thr Ser Pro Thr
                485                 490                 495

Val Glu Leu Ser Gly Glu Pro Gly Asp Asp Gly Pro Ser Gly Ala Glu
            500                 505                 510

Gly Pro Pro Gly Pro Gln Gly
        515

<210> SEQ ID NO 8
<211> LENGTH: 519
<212> TYPE: PRT
<213> ORGANISM: Unknown
<220> FEATURE:
<223> OTHER INFORMATION: mouse -continued

```
<220> FEATURE:
<221> NAME/KEY: PROTEIN
<222> LOCATION: (1)..(519)

<400> SEQUENCE: 8
```

| | | | | | | | | | | | | | | |
|---|---|---|---|---|---|---|---|---|---|---|---|---|---|---|
| Met | Arg | Asn | Thr | Val | Phe | Leu | Leu | Gly | Phe | Trp | Ser | Val | Tyr | Cys | Tyr |
| 1 | | | | 5 | | | | | 10 | | | | | 15 | |
| Phe | Pro | Ala | Gly | Ser | Ile | Thr | Thr | Leu | Arg | Pro | Glu | Gly | Ser | Leu | Arg |
| | | | 20 | | | | | 25 | | | | | 30 | | |
| Asp | Glu | His | His | Lys | Pro | Thr | Gly | Val | Pro | Ala | Thr | Ala | Arg | Pro | Ser |
| | | | 35 | | | | | 40 | | | | | 45 | | |
| Val | Ala | Phe | Asn | Ile | Arg | Thr | Ser | Lys | Asp | Pro | Glu | Gln | Glu | Gly | Cys |
| | 50 | | | | | 55 | | | | | 60 | | | | |
| Asn | Leu | Ser | Leu | Gly | Asp | Ser | Lys | Leu | Leu | Glu | Asn | Cys | Gly | Phe | Asn |
| 65 | | | | | 70 | | | | | 75 | | | | | 80 |
| Met | Thr | Ala | Lys | Thr | Phe | Phe | Ile | Ile | His | Gly | Trp | Thr | Met | Ser | Gly |
| | | | | 85 | | | | | 90 | | | | | 95 | |
| Met | Phe | Glu | Ser | Trp | Leu | His | Lys | Leu | Val | Ser | Ala | Leu | Gln | Met | Arg |
| | | | 100 | | | | | 105 | | | | | 110 | | |
| Glu | Lys | Asp | Ala | Asn | Val | Val | Val | Asp | Trp | Leu | Pro | Leu | Ala | His | |
| | | | 115 | | | | | 120 | | | | | 125 | | |
| Gln | Leu | Tyr | Thr | Asp | Ala | Val | Asn | Asn | Thr | Arg | Val | Val | Gly | Gln | Arg |
| | 130 | | | | | 135 | | | | | 140 | | | | |
| Val | Ala | Gly | Met | Leu | Asp | Trp | Leu | Gln | Glu | Lys | Glu | Glu | Phe | Ser | Leu |
| 145 | | | | | 150 | | | | | 155 | | | | | 160 |
| Gly | Asn | Val | His | Leu | Ile | Gly | Tyr | Ser | Leu | Gly | Ala | His | Val | Ala | Gly |
| | | | | 165 | | | | | 170 | | | | | 175 | |
| Tyr | Ala | Gly | Asn | Phe | Val | Lys | Gly | Thr | Val | Gly | Arg | Ile | Thr | Gly | Leu |
| | | | 180 | | | | | 185 | | | | | 190 | | |
| Asp | Pro | Ala | Gly | Pro | Met | Phe | Glu | Gly | Val | Asp | Ile | Asn | Arg | Arg | Leu |
| | | | 195 | | | | | 200 | | | | | 205 | | |
| Ser | Pro | Asp | Asp | Ala | Asp | Phe | Val | Asp | Val | Leu | His | Thr | Tyr | Thr | Leu |
| | 210 | | | | | 215 | | | | | 220 | | | | |
| Ser | Phe | Gly | Leu | Ser | Ile | Gly | Ile | Arg | Met | Pro | Val | Gly | His | Ile | Asp |
| 225 | | | | | 230 | | | | | 235 | | | | | 240 |
| Ile | Tyr | Pro | Asn | Gly | Gly | Asp | Phe | Gln | Pro | Gly | Cys | Gly | Phe | Asn | Asp |
| | | | | 245 | | | | | 250 | | | | | 255 | |
| Val | Ile | Gly | Ser | Phe | Ala | Tyr | Gly | Thr | Ile | Ser | Glu | Met | Val | Lys | Cys |
| | | | 260 | | | | | 265 | | | | | 270 | | |
| Glu | His | Glu | Arg | Ala | Val | His | Leu | Phe | Val | Asp | Ser | Leu | Val | Asn | Gln |
| | | | 275 | | | | | 280 | | | | | 285 | | |
| Asp | Lys | Pro | Ser | Phe | Ala | Phe | Gln | Cys | Thr | Asp | Ser | Ser | Arg | Phe | Lys |
| | 290 | | | | | 295 | | | | | 300 | | | | |
| Arg | Gly | Ile | Cys | Leu | Ser | Cys | Arg | Lys | Asn | Arg | Cys | Asn | Asn | Ile | Gly |
| 305 | | | | | 310 | | | | | 315 | | | | | 320 |
| Tyr | Asn | Ala | Lys | Lys | Met | Arg | Lys | Arg | Asn | Ser | Lys | Met | Tyr | Leu | |
| | | | | 325 | | | | | 330 | | | | | 335 | |
| Lys | Thr | Arg | Ala | Gly | Met | Pro | Phe | Lys | Val | Tyr | His | Tyr | Gln | Leu | Lys |
| | | | 340 | | | | | 345 | | | | | 350 | | |
| Val | His | Met | Phe | Ser | Tyr | Asn | Ser | Gly | Asp | Thr | Gln | Pro | Thr | Leu | |
| | | | 355 | | | | | 360 | | | | | 365 | | |
| Tyr | Ile | Thr | Leu | Tyr | Gly | Ser | Asn | Ala | Asp | Ser | Gln | Asn | Leu | Pro | Leu |
| | 370 | | | | | 375 | | | | | 380 | | | | |
| Glu | Ile | Val | Glu | Lys | Ile | Glu | Leu | Asn | Ala | Thr | Asn | Thr | Phe | Leu | Val |

```
                    385                 390                 395                 400
Tyr Thr Glu Glu Asp Leu Gly Asp Leu Leu Lys Met Arg Leu Thr Trp
                405                 410                 415

Glu Gly Val Ala His Ser Trp Tyr Asn Leu Trp Asn Glu Phe Arg Asn
            420                 425                 430

Tyr Leu Ser Gln Pro Ser Asn Pro Ser Arg Glu Leu Tyr Ile Arg Arg
        435                 440                 445

Ile Arg Val Lys Ser Gly Glu Thr Gln Arg Lys Val Thr Phe Cys Thr
    450                 455                 460

Gln Asp Pro Thr Lys Ser Ser Ile Ser Pro Gly Gln Glu Leu Trp Phe
465                 470                 475                 480

His Lys Cys Gln Asp Gly Trp Lys Met Lys Asn Lys Thr Ser Pro Phe
                485                 490                 495

Val Asn Leu Ala Gly Glu Pro Gly Asp Asp Gly Pro Ser Gly Ala Glu
            500                 505                 510

Gly Pro Pro Gly Pro Gln Gly
        515

<210> SEQ ID NO 9
<211> LENGTH: 120
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(120)

<400> SEQUENCE: 9

Gln Ile His Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Ser Gly Val Pro Thr Tyr Ala Gly Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Arg Gly Tyr Tyr Gly Arg Arg Tyr Phe Asp Val Trp Gly Thr
            100                 105                 110

Gly Thr Thr Val Thr Val Ser Ser
        115                 120

<210> SEQ ID NO 10
<211> LENGTH: 5
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(5)

<400> SEQUENCE: 10

Asn Tyr Gly Met Asn
1               5
```

<210> SEQ ID NO 11
<211> LENGTH: 17
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(17)

<400> SEQUENCE: 11

Trp Ile Asn Thr Tyr Ser Gly Val Pro Thr Tyr Ala Gly Asp Phe Lys
1               5                   10                  15

Gly

<210> SEQ ID NO 12
<211> LENGTH: 11
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(11)

<400> SEQUENCE: 12

Arg Gly Tyr Tyr Gly Arg Arg Tyr Phe Asp Val
1               5                   10

<210> SEQ ID NO 13
<211> LENGTH: 111
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(111)

<400> SEQUENCE: 13

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
                20                  25                  30

Val Asp Ser Tyr Met His Trp Tyr Gln Gln Lys Pro Gly Gln Pro Pro
            35                  40                  45

Lys Leu Leu Ile Tyr Ala Ala Ser Asn Leu Ala Ser Gly Ile Pro Ala
        50                  55                  60

Arg Phe Ser Gly Gly Gly Ser Gly Thr Asp Phe Thr Leu Asn Ile His
65                  70                  75                  80

Pro Val Glu Glu Glu Asp Val Ala Thr Tyr Tyr Cys Gln Gln Thr Ile
                85                  90                  95

Glu Asp Pro Pro Thr Phe Gly Gly Gly Thr Lys Leu Gly Ile Lys
            100                 105                 110

<210> SEQ ID NO 14
<211> LENGTH: 15
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(15)

<400> SEQUENCE: 14

Lys Ala Ser Gln Ser Val Asp Tyr Asp Val Asp Ser Tyr Met His
1               5                   10                  15

<210> SEQ ID NO 15
<211> LENGTH: 7
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(7)

<400> SEQUENCE: 15

Ala Ala Ser Asn Leu Ala Ser
1               5

<210> SEQ ID NO 16
<211> LENGTH: 9
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(9)

<400> SEQUENCE: 16

Gln Gln Thr Ile Glu Asp Pro Pro Thr
1               5

<210> SEQ ID NO 17
<211> LENGTH: 120
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(120)

<400> SEQUENCE: 17

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
                20                  25                  30

Gly Met Asn Trp Val Lys Gln Ala Pro Gly Lys Asp Leu Lys Trp Met
            35                  40                  45

Gly Trp Ile Asn Thr Tyr Ser Gly Val Pro Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Phe Ser Tyr Tyr Gly Arg His Tyr Phe Asp Tyr Trp Gly Gln
            100                 105                 110

Gly Thr Thr Leu Thr Val Ser Ser
        115                 120

<210> SEQ ID NO 18
<211> LENGTH: 5
<212> TYPE: PRT
<213> ORGANISM: Unknown

```
<220> FEATURE:
<223> OTHER INFORMATION: mouse
<220> FEATURE:
<221> NAME/KEY: PROTEIN
<222> LOCATION: (1)..(5)

<400> SEQUENCE: 18

Asn Tyr Gly Met Asn
1               5

<210> SEQ ID NO 19
<211> LENGTH: 17
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(17)

<400> SEQUENCE: 19

Trp Ile Asn Thr Tyr Ser Gly Val Pro Thr Tyr Ala Asp Asp Phe Lys
1               5                   10                  15

Gly

<210> SEQ ID NO 20
<211> LENGTH: 11
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(11)

<400> SEQUENCE: 20

Phe Ser Tyr Tyr Gly Arg His Tyr Phe Asp Tyr
1               5                   10

<210> SEQ ID NO 21
<211> LENGTH: 112
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(112)

<400> SEQUENCE: 21

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Gln Leu Leu Ile Tyr Ala Ala Ser Asn Leu Gly Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys His Gln Ser Thr
                85                  90                  95

Asp Asp Pro Pro Trp Thr Phe Gly Gly Gly Thr Lys Leu Glu Ile Lys
            100                 105                 110
```

<210> SEQ ID NO 22
<211> LENGTH: 15
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(15)

<400> SEQUENCE: 22

Lys Ala Ser Gln Ser Val Asp Tyr Asp Gly Asp Ser Tyr Met Asn
1               5                   10                  15

<210> SEQ ID NO 23
<211> LENGTH: 7
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(7)

<400> SEQUENCE: 23

Ala Ala Ser Asn Leu Gly Ser
1               5

<210> SEQ ID NO 24
<211> LENGTH: 10
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(10)

<400> SEQUENCE: 24

His Gln Ser Thr Asp Asp Pro Pro Trp Thr
1               5                   10

<210> SEQ ID NO 25
<211> LENGTH: 120
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(120)

<400> SEQUENCE: 25

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Ser Gly Val Pro Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Phe Lys Asn Glu Asp Thr Ala Thr Tyr Phe Cys
                85                  90                  95

Ala Arg Phe Ser Tyr Tyr Gly Arg His Tyr Phe Asp Tyr Trp Gly Gln
            100                 105                 110

Gly Thr Ala Leu Thr Ala Ser Ser
        115                 120

<210> SEQ ID NO 26
<211> LENGTH: 5
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(5)

<400> SEQUENCE: 26

Asn Tyr Gly Met Asn
1               5

<210> SEQ ID NO 27
<211> LENGTH: 17
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(17)

<400> SEQUENCE: 27

Trp Ile Asn Thr Tyr Ser Gly Val Pro Thr Tyr Ala Asp Asp Phe Lys
1               5                   10                  15

Gly

<210> SEQ ID NO 28
<211> LENGTH: 11
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(11)

<400> SEQUENCE: 28

Phe Ser Tyr Tyr Gly Arg His Tyr Phe Asp Tyr
1               5                   10

<210> SEQ ID NO 29
<211> LENGTH: 112
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(112)

<400> SEQUENCE: 29

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Lys Ser Gly Ile Pro Ala

-continued

```
                     50                  55                  60
Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln Gln Thr Thr
                 85                  90                  95

Asp Asp Pro Pro Trp Thr Phe Gly Gly Thr Lys Leu Glu Ile Lys
            100                 105                 110
```

<210> SEQ ID NO 30
<211> LENGTH: 15
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(15)

<400> SEQUENCE: 30

```
Lys Ala Ser Gln Ser Val Asp Tyr Asp Gly Asp Ser Tyr Met Asn
 1               5                  10                  15
```

<210> SEQ ID NO 31
<211> LENGTH: 7
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(7)

<400> SEQUENCE: 31

```
Ala Ala Ser Asn Leu Lys Ser
 1               5
```

<210> SEQ ID NO 32
<211> LENGTH: 10
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(10)

<400> SEQUENCE: 32

```
Gln Gln Thr Thr Asp Asp Pro Pro Trp Thr
 1               5                  10
```

<210> SEQ ID NO 33
<211> LENGTH: 120
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(120)

<400> SEQUENCE: 33

```
Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Asn Tyr
                20                  25                  30

Gly Met Asn Trp Val Lys Gln Ala Pro Gly Lys Gly Leu Lys Trp Met
```

```
                35                  40                  45
Gly Trp Ile Asn Thr Tyr Ser Gly Val Pro Thr Tyr Thr Asp Asp Phe
        50                  55                  60

Lys Gly Arg Phe Ala Phe Ser Leu Glu Thr Ser Ala Ser Thr Ala Phe
 65                  70                  75                  80

Leu Gln Ile Asn Asn Leu Lys Asn Glu Asp Thr Ala Thr Tyr Phe Cys
                85                  90                  95

Ala Arg Phe Ser Tyr Tyr Gly Arg His Tyr Phe Asp Tyr Trp Gly Gln
            100                 105                 110

Gly Thr Thr Leu Thr Val Ser Ser
        115                 120

<210> SEQ ID NO 34
<211> LENGTH: 5
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(5)

<400> SEQUENCE: 34

Asn Tyr Gly Met Asn
 1               5

<210> SEQ ID NO 35
<211> LENGTH: 17
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(17)

<400> SEQUENCE: 35

Trp Ile Asn Thr Tyr Ser Gly Val Pro Thr Tyr Thr Asp Asp Phe Lys
 1               5                  10                  15

Gly

<210> SEQ ID NO 36
<211> LENGTH: 11
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(11)

<400> SEQUENCE: 36

Phe Ser Tyr Tyr Gly Arg His Tyr Phe Asp Tyr
 1               5                  10

<210> SEQ ID NO 37
<211> LENGTH: 112
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(112)

<400> SEQUENCE: 37
```

```
Asp Ile Val Leu Thr Gln Ser Pro Ala Ser Leu Ala Val Ser Leu Gly
 1               5                  10                  15

Gln Arg Ala Thr Ile Ser Cys Lys Ala Ser Gln Ser Val Asp Tyr Asp
                20                  25                  30

Gly Asp Ser Tyr Met His Trp Tyr Gln Gln Lys Pro Gly Gln Pro Pro
            35                  40                  45

Lys Leu Leu Ile Tyr Ala Ala Ser Asn Leu Glu Ser Gly Ile Pro Ala
        50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln Gln Thr Asn
                85                  90                  95

Asp Asp Pro Pro Trp Thr Phe Gly Gly Gly Thr Lys Leu Glu Ile Lys
            100                 105                 110
```

<210> SEQ ID NO 38
<211> LENGTH: 15
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(15)

<400> SEQUENCE: 38

```
Lys Ala Ser Gln Ser Val Asp Tyr Asp Gly Asp Ser Tyr Met His
 1               5                  10                  15
```

<210> SEQ ID NO 39
<211> LENGTH: 7
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(7)

<400> SEQUENCE: 39

```
Ala Ala Ser Asn Leu Glu Ser
 1               5
```

<210> SEQ ID NO 40
<211> LENGTH: 10
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(10)

<400> SEQUENCE: 40

```
Gln Gln Thr Asn Asp Asp Pro Pro Trp Thr
 1               5                  10
```

<210> SEQ ID NO 41
<211> LENGTH: 119
<212> TYPE: PRT
<213> ORGANISM: Unknown
<220> FEATURE:
<223> OTHER INFORMATION: mouse
<220> FEATURE:
<221> NAME/KEY: PROTEIN

```
<222> LOCATION: (1)..(119)

<400> SEQUENCE: 41

Glu Val Gln Leu Gln Gln Ser Gly Pro Glu Leu Leu Lys Pro Gly Ala
1               5                   10                  15

Ser Val Lys Ile Ser Cys Lys Ala Ser Gly Tyr Thr Phe Thr Asp Tyr
                20                  25                  30

Thr Met His Trp Val Lys Gln Ser His Gly Lys Ser Leu Glu Trp Ile
            35                  40                  45

Gly Gly Ile Asn Pro Tyr Tyr Gly Gly Thr Thr Tyr Asn Glu Lys Phe
        50                  55                  60

Lys Asp Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Lys Gly Asp Tyr Tyr Gly Gly Ser Tyr Asn Tyr Trp Gly Gln Gly
            100                 105                 110

Thr Thr Leu Thr Val Ser Ser
        115

<210> SEQ ID NO 42
<211> LENGTH: 5
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(5)

<400> SEQUENCE: 42

Asp Tyr Thr Met His
1               5

<210> SEQ ID NO 43
<211> LENGTH: 17
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(17)

<400> SEQUENCE: 43

Gly Ile Asn Pro Tyr Tyr Gly Gly Thr Thr Tyr Asn Glu Lys Phe Lys
1               5                   10                  15

Asp

<210> SEQ ID NO 44
<211> LENGTH: 10
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(10)

<400> SEQUENCE: 44

Gly Asp Tyr Tyr Gly Gly Ser Tyr Asn Tyr
1               5                   10
```

```
<210> SEQ ID NO 45
<211> LENGTH: 107
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(107)

<400> SEQUENCE: 45

Asp Ile Val Leu Thr Gln Ser Leu Ala Thr Leu Ser Val Thr Pro Gly
1               5                   10                  15

Asp Ser Val Ser Leu Ser Cys Arg Ala Ser Gln Asp Ile Ser Asn Ser
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro Tyr
                85                  90                  95

Thr Phe Gly Gly Gly Thr Lys Leu Glu Ile Lys
            100                 105

<210> SEQ ID NO 46
<211> LENGTH: 11
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(11)

<400> SEQUENCE: 46

Arg Ala Ser Gln Asp Ile Ser Asn Ser Leu His
1               5                   10

<210> SEQ ID NO 47
<211> LENGTH: 7
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(7)

<400> SEQUENCE: 47

Tyr Ala Ser Gln Ser Ile Ser
1               5

<210> SEQ ID NO 48
<211> LENGTH: 9
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(9)

<400> SEQUENCE: 48

Gln Gln Ser Asn Ser Trp Pro Tyr Thr
```

```
<210> SEQ ID NO 49
<211> LENGTH: 119
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(119)

<400> SEQUENCE: 49

Glu Val Gln Leu Gln Gln Ser Gly Pro Glu Leu Leu Lys Pro Gly Ala
1               5                   10                  15

Ser Val Lys Ile Ser Cys Lys Ala Ser Gly Tyr Thr Phe Thr Glu Tyr
            20                  25                  30

Thr Met His Trp Val Lys Gln Ser His Gly Lys Ser Leu Glu Trp Ile
        35                  40                  45

Gly Ser Ile Asn Pro Tyr Tyr Gly Gly Thr Ser Tyr Asn Glu Lys Phe
    50                  55                  60

Lys Asp Lys Ala Thr Leu Thr Val Asp Lys Ser Ser Asn Thr Ala Tyr
65                  70                  75                  80

Met Glu Phe Arg Ser Leu Thr Ser Glu Asp Cys Ala Val Tyr Tyr Cys
                85                  90                  95

Ala Arg Tyr Gly Asn Tyr Val Gly Tyr Phe Asp Tyr Trp Gly Gln Gly
            100                 105                 110

Thr Thr Leu Thr Val Ser Ser
        115

<210> SEQ ID NO 50
<211> LENGTH: 5
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(5)

<400> SEQUENCE: 50

Glu Tyr Thr Met His
1               5

<210> SEQ ID NO 51
<211> LENGTH: 17
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(17)

<400> SEQUENCE: 51

Ser Ile Asn Pro Tyr Tyr Gly Gly Thr Ser Tyr Asn Glu Lys Phe Lys
1               5                   10                  15

Asp

<210> SEQ ID NO 52
<211> LENGTH: 10
<212> TYPE: PRT
<213> ORGANISM: Unknown
<220> FEATURE:
```

```
<223> OTHER INFORMATION: mouse
<220> FEATURE:
<221> NAME/KEY: PROTEIN
<222> LOCATION: (1)..(10)

<400> SEQUENCE: 52

Tyr Gly Asn Tyr Val Gly Tyr Phe Asp Tyr
1               5                   10

<210> SEQ ID NO 53
<211> LENGTH: 106
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(106)

<400> SEQUENCE: 53

Glu Asn Val Leu Thr Gln Ser Pro Ala Ile Met Ser Ala Ser Leu Gly
1               5                   10                  15

Glu Lys Val Thr Met Ser Cys Arg Ala Ser Ser Ser Val His Tyr Met
                20                  25                  30

Tyr Trp Tyr Gln Gln Lys Ser Asp Ala Ser Pro Lys Leu Trp Ile Tyr
            35                  40                  45

Tyr Thr Ser Asn Leu Ala Pro Gly Val Pro Asp Arg Phe Ser Gly Ser
        50                  55                  60

Gly Ser Gly Asn Ser Tyr Ser Leu Thr Ile Ser Ser Met Glu Gly Glu
65                  70                  75                  80

Asp Ala Ala Thr Tyr Tyr Cys Gln Gln Phe Thr Ser Ser Pro Tyr Thr
                85                  90                  95

Phe Gly Gly Gly Thr Lys Leu Glu Ile Lys
            100                 105

<210> SEQ ID NO 54
<211> LENGTH: 10
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(10)

<400> SEQUENCE: 54

Arg Ala Ser Ser Ser Val His Tyr Met Tyr
1               5                   10

<210> SEQ ID NO 55
<211> LENGTH: 7
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(7)

<400> SEQUENCE: 55

Tyr Thr Ser Asn Leu Ala Pro
1               5

<210> SEQ ID NO 56
<211> LENGTH: 9
```

<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(9)

<400> SEQUENCE: 56

Gln Gln Phe Thr Ser Ser Pro Tyr Thr
1               5

<210> SEQ ID NO 57
<211> LENGTH: 120
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(120)

<400> SEQUENCE: 57

Glu Val Gln Leu Gln Gln Ser Gly Pro Glu Leu Leu Lys Pro Gly Ala
1               5                   10                  15

Ser Val Lys Ile Ser Cys Lys Ala Ser Gly Tyr Thr Phe Thr Asp Asn
                20                  25                  30

Thr Ile His Trp Val Lys Gln Ser His Gly Lys Ser Leu Glu Trp Ile
            35                  40                  45

Gly His Ile Asn Pro Tyr Tyr Gly Gly Thr Asn Asn Asn Glu Lys Phe
        50                  55                  60

Lys Asp Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Ile Tyr Tyr Cys
                85                  90                  95

Ala Arg Lys Gly Ile Tyr Tyr Ser Ser Pro Phe Asp Tyr Trp Gly Gln
                100                 105                 110

Gly Thr Thr Leu Thr Val Ser Ser
            115                 120

<210> SEQ ID NO 58
<211> LENGTH: 5
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(5)

<400> SEQUENCE: 58

Asp Asn Thr Ile His
1               5

<210> SEQ ID NO 59
<211> LENGTH: 17
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(17)

<400> SEQUENCE: 59

His Ile Asn Pro Tyr Tyr Gly Gly Thr Asn Asn Glu Lys Phe Lys
1               5                   10                  15

Asp

<210> SEQ ID NO 60
<211> LENGTH: 11
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(11)

<400> SEQUENCE: 60

Lys Gly Ile Tyr Tyr Ser Ser Pro Phe Asp Tyr
1               5                   10

<210> SEQ ID NO 61
<211> LENGTH: 107
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(107)

<400> SEQUENCE: 61

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Asn Asn Tyr
            20                  25                  30

Leu Asn Trp Tyr Gln Gln Lys Pro Asp Gly Thr Val Lys Leu Leu Ile
        35                  40                  45

Ser Tyr Thr Ser Lys Leu His Ser Gly Val Pro Ser Arg Phe Ser Gly
50                  55                  60

Ser Gly Ser Gly Thr Asp Tyr Ser Leu Thr Ile Ser Asn Leu Glu Arg
65                  70                  75                  80

Glu Asp Phe Ala Thr Tyr Phe Cys Gln Gln Gly Asn Thr Leu Pro Phe
                85                  90                  95

Thr Phe Gly Ser Gly Thr Asn Leu Glu Ile Lys
            100                 105

<210> SEQ ID NO 62
<211> LENGTH: 11
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(11)

<400> SEQUENCE: 62

Arg Ala Ser Gln Asp Ile Asn Asn Tyr Leu Asn
1               5                   10

<210> SEQ ID NO 63
<211> LENGTH: 7
<212> TYPE: PRT
<213> ORGANISM: Unknown
<220> FEATURE:
<223> OTHER INFORMATION: mouse
<220> FEATURE:

<221> NAME/KEY: PROTEIN
<222> LOCATION: (1)..(7)

<400> SEQUENCE: 63

Tyr Thr Ser Lys Leu His Ser
1               5

<210> SEQ ID NO 64
<211> LENGTH: 9
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(9)

<400> SEQUENCE: 64

Gln Gln Gly Asn Thr Leu Pro Phe Thr
1               5

<210> SEQ ID NO 65
<211> LENGTH: 122
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(122)

<400> SEQUENCE: 65

Asp Val Lys Leu Val Glu Ser Gly Gly Gly Leu Val Gln Pro Gly Gly
1               5                   10                  15

Ser Leu Lys Leu Ser Cys Thr Ala Ser Gly Phe Thr Phe Ser Gly Tyr
            20                  25                  30

Thr Met Ser Trp Val Arg Gln Thr Pro Glu Lys Arg Leu Glu Leu Val
        35                  40                  45

Ala Glu Ile Ser Phe Ala Arg Asp Arg Ala Phe Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Thr Arg Leu Gly Gly Arg Asn His Asp Tyr Trp Tyr Phe Asp Val Trp
            100                 105                 110

Gly Thr Gly Thr Thr Val Thr Val Ser Ser
        115                 120

<210> SEQ ID NO 66
<211> LENGTH: 5
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(5)

<400> SEQUENCE: 66

Gly Tyr Thr Met Ser
1               5

<210> SEQ ID NO 67

```
<211> LENGTH: 17
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(17)

<400> SEQUENCE: 67

Glu Ile Ser Phe Ala Arg Asp Arg Ala Phe Tyr Pro Asp Thr Val Lys
1               5                   10                  15

Gly

<210> SEQ ID NO 68
<211> LENGTH: 13
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(13)

<400> SEQUENCE: 68

Leu Gly Gly Arg Asn His Asp Tyr Trp Tyr Phe Asp Val
1               5                   10

<210> SEQ ID NO 69
<211> LENGTH: 111
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(111)

<400> SEQUENCE: 69

Asp Ile Val Leu Thr Gln Ser Pro Thr Ser Leu Ala Val Ser Pro Gly
1               5                   10                  15

Gln Arg Ala Thr Ile Ser Cys Arg Ala Ser Glu Ser Val Glu Tyr Tyr
            20                  25                  30

Gly Thr Ser Leu Met Gln Trp Tyr Gln Gln Lys Pro Gly Gln Arg Pro
        35                  40                  45

Gln Leu Leu Ile Tyr Ala Ala Ser Asn Val Glu Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Val Tyr Phe Cys Gln Gln Ser Trp
                85                  90                  95

Lys Val Pro Phe Thr Phe Gly Ser Gly Thr Lys Leu Glu Ile Lys
            100                 105                 110

<210> SEQ ID NO 70
<211> LENGTH: 15
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(15)

<400> SEQUENCE: 70
```

Arg Ala Ser Glu Ser Val Glu Tyr Tyr Gly Thr Ser Leu Met Gln
1               5                   10                  15

<210> SEQ ID NO 71
<211> LENGTH: 7
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(7)

<400> SEQUENCE: 71

Ala Ala Ser Asn Val Glu Ser
1               5

<210> SEQ ID NO 72
<211> LENGTH: 9
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(9)

<400> SEQUENCE: 72

Gln Gln Ser Trp Lys Val Pro Phe Thr
1               5

<210> SEQ ID NO 73
<211> LENGTH: 122
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(122)

<400> SEQUENCE: 73

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
                20                  25                  30

Thr Met Ser Trp Val Arg Gln Thr Pro Glu Lys Arg Leu Glu Leu Val
            35                  40                  45

Ala Glu Ile Ser Phe Thr Arg Ser Arg Ala Phe Tyr Pro Asp Thr Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Leu Gly Gly Asn Asn Tyr Asp Tyr Trp Tyr Phe Asp Val Trp
            100                 105                 110

Gly Thr Gly Thr Thr Val Thr Val Ser Ser
        115                 120

<210> SEQ ID NO 74
<211> LENGTH: 5
<212> TYPE: PRT
<213> ORGANISM: Unknown
<220> FEATURE:
<223> OTHER INFORMATION: mouse

```
<220> FEATURE:
<221> NAME/KEY: PROTEIN
<222> LOCATION: (1)..(5)

<400> SEQUENCE: 74

Ser Tyr Thr Met Ser
1               5

<210> SEQ ID NO 75
<211> LENGTH: 17
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(17)

<400> SEQUENCE: 75

Glu Ile Ser Phe Thr Arg Ser Arg Ala Phe Tyr Pro Asp Thr Val Lys
1               5                   10                  15

Gly

<210> SEQ ID NO 76
<211> LENGTH: 13
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(13)

<400> SEQUENCE: 76

Leu Gly Gly Asn Asn Tyr Asp Tyr Trp Tyr Phe Asp Val
1               5                   10

<210> SEQ ID NO 77
<211> LENGTH: 111
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(15)

<400> SEQUENCE: 77

Asp Ile Val Leu Thr Gln Ser Pro Thr Ser Leu Ala Val Ser Leu Gly
1               5                   10                  15

Gln Arg Ala Thr Ile Ser Cys Arg Ala Ser Glu Ser Val Glu Tyr Tyr
            20                  25                  30

Gly Thr Ser Leu Met Gln Trp Tyr Gln Gln Lys Pro Gly Gln Arg Pro
        35                  40                  45

Lys Leu Leu Ile Tyr Ala Ala Ser Asn Val Glu Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Met Tyr Phe Cys Gln Gln Ser Trp
                85                  90                  95

Lys Val Pro Phe Thr Phe Gly Ser Gly Thr Lys Leu Glu Ile Lys
            100                 105                 110

<210> SEQ ID NO 78
```

-continued

```
<211> LENGTH: 15
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(15)

<400> SEQUENCE: 78

Arg Ala Ser Glu Ser Val Glu Tyr Tyr Gly Thr Ser Leu Met Gln
1               5                   10                  15

<210> SEQ ID NO 79
<211> LENGTH: 7
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(7)

<400> SEQUENCE: 79

Ala Ala Ser Asn Val Glu Ser
1               5

<210> SEQ ID NO 80
<211> LENGTH: 9
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(9)

<400> SEQUENCE: 80

Gln Gln Ser Trp Lys Val Pro Phe Thr
1               5

<210> SEQ ID NO 81
<211> LENGTH: 119
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(119)

<400> SEQUENCE: 81

Gln Val Gln Leu Gln Gln Ser Gly Ala Glu Leu Val Lys Pro Gly Ala
1               5                   10                  15

Ser Val Arg Leu Ser Cys Lys Ala Ser Gly Tyr Thr Phe Thr Lys Tyr
                20                  25                  30

Thr Ile His Trp Val Lys Gln Arg Ser Gly Gln Gly Leu Glu Trp Ile
            35                  40                  45

Gly Trp Phe Tyr Pro Gly Ser Asp Ser Ile Lys Tyr Asn Glu Lys Phe
        50                  55                  60

Lys Asp Lys Ala Thr Leu Thr Ala Asp Lys Ser Ser Arg Thr Val Tyr
65                  70                  75                  80

Met Glu Leu Ser Arg Leu Thr Ser Glu Asp Ser Ala Val Tyr Phe Cys
                85                  90                  95

Ala Arg His Glu Glu Tyr Thr Asn Ser Leu Ala Tyr Trp Gly Gln Gly
                100                 105                 110
```

Thr Leu Val Thr Val Ser Ala
        115

<210> SEQ ID NO 82
<211> LENGTH: 5
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(5)

<400> SEQUENCE: 82

Lys Tyr Thr Ile His
1               5

<210> SEQ ID NO 83
<211> LENGTH: 17
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(17)

<400> SEQUENCE: 83

Trp Phe Tyr Pro Gly Ser Asp Ser Ile Lys Tyr Asn Glu Lys Phe Lys
1               5                   10                  15

Asp

<210> SEQ ID NO 84
<211> LENGTH: 10
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(10)

<400> SEQUENCE: 84

His Glu Glu Tyr Thr Asn Ser Leu Ala Tyr
1               5                   10

<210> SEQ ID NO 85
<211> LENGTH: 107
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(107)

<400> SEQUENCE: 85

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Gln Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

-continued

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Tyr Thr Leu Pro Trp
                85                  90                  95

Thr Phe Gly Gly Gly Thr Asn Leu Glu Ile Lys
            100                 105

<210> SEQ ID NO 86
<211> LENGTH: 11
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(11)

<400> SEQUENCE: 86

Arg Ala Ser Gln Asp Ile Ser Asn Tyr Leu Asn
1               5                   10

<210> SEQ ID NO 87
<211> LENGTH: 7
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(7)

<400> SEQUENCE: 87

Tyr Thr Ser Arg Leu His Ser
1               5

<210> SEQ ID NO 88
<211> LENGTH: 9
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(9)

<400> SEQUENCE: 88

Gln Gln Gly Tyr Thr Leu Pro Trp Thr
1               5

<210> SEQ ID NO 89
<211> LENGTH: 118
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(118)

<400> SEQUENCE: 89

Gln Val Gln Leu Gln Gln Pro Gly Ser Val Leu Val Arg Pro Gly Ala
1               5                   10                  15

Ser Val Lys Leu Ser Cys Lys Ala Ser Gly Tyr Thr Phe Thr Thr Tyr
                20                  25                  30

Trp Met His Trp Val Lys Gln Arg Pro Gly Gln Gly Leu Glu Trp Ile
            35                  40                  45

Gly Glu Ile His Pro Tyr Ser Gly Asn Asn Asn Asn Glu Lys Phe
            50                  55                  60

Lys Gly Lys Ala Thr Leu Thr Val Asp Thr Ser Ser Thr Ala Tyr
 65                  70                  75                  80

Val Asp Leu Ser Arg Leu Thr Ser Glu Asp Ser Ala Val Tyr Cys
                 85                  90                  95

Ala Arg Tyr Asp Ser Asn Tyr Val Phe Ala Tyr Trp Gly Gln Gly Thr
                100                 105                 110

Leu Val Thr Val Ser Ala
        115

<210> SEQ ID NO 90
<211> LENGTH: 5
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(5)

<400> SEQUENCE: 90

Thr Tyr Trp Met His
 1               5

<210> SEQ ID NO 91
<211> LENGTH: 17
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(17)

<400> SEQUENCE: 91

Glu Ile His Pro Tyr Ser Gly Asn Asn Asn Glu Lys Phe Lys
 1               5                  10                  15

Gly

<210> SEQ ID NO 92
<211> LENGTH: 9
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(9)

<400> SEQUENCE: 92

Tyr Asp Ser Asn Tyr Val Phe Ala Tyr
 1               5

<210> SEQ ID NO 93
<211> LENGTH: 105
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(105)

<400> SEQUENCE: 93

Gln Ile Val Leu Thr Gln Ser Pro Ala Ile Met Ser Ala Ser Pro Gly

-continued

```
1               5                   10                  15
Glu Gly Val Thr Ile Thr Cys Ser Ala Ser Ser Ser Val Ser Tyr Met
            20                  25                  30
His Trp Phe Gln Gln Lys Pro Gly Thr Ser Pro Lys Leu Trp Ile Tyr
        35                  40                  45
Ser Thr Ser Asn Leu Ala Ser Gly Val Pro Ala Arg Phe Ser Gly Ser
    50                  55                  60
Gly Ser Gly Thr Ser Tyr Ser Leu Thr Ile Ser Arg Met Glu Ala Glu
65                  70                  75                  80
Asp Ala Ala Thr Tyr Tyr Cys Gln Gln Arg Asp Ser Tyr Leu Thr Phe
                85                  90                  95
Gly Ser Gly Thr Lys Leu Glu Val Lys
                100                 105
```

```
<210> SEQ ID NO 94
<211> LENGTH: 10
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(10)

<400> SEQUENCE: 94

Ser Ala Ser Ser Ser Val Ser Tyr Met His
1               5                   10
```

```
<210> SEQ ID NO 95
<211> LENGTH: 7
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(7)

<400> SEQUENCE: 95

Ser Thr Ser Asn Leu Ala Ser
1               5
```

```
<210> SEQ ID NO 96
<211> LENGTH: 8
<212> TYPE: PRT
<213> ORGANISM: Unknown
<220> FEATURE:
<223> OTHER INFORMATION: mouse
<220> FEATURE:
<221> NAME/KEY: PROTEIN
<222> LOCATION: (1)..(8)

<400> SEQUENCE: 96

Gln Gln Arg Asp Ser Tyr Leu Thr
1               5
```

```
<210> SEQ ID NO 97
<211> LENGTH: 519
<212> TYPE: PRT
<213> ORGANISM: Artificial Sequence
<220> FEATURE:
<223> OTHER INFORMATION: Synthetic: chimera
<220> FEATURE:
<221> NAME/KEY: PROTEIN
<222> LOCATION: (1)..(519)
```

<400> SEQUENCE: 97

```
Met Ser Asn Ser Val Pro Leu Leu Cys Phe Trp Ser Leu Cys Tyr Cys
1               5                   10                  15

Phe Ala Ala Gly Ser Pro Val Pro Phe Gly Pro Glu Gly Arg Leu Glu
                20                  25                  30

Asp Lys Leu His Lys Pro Lys Ala Thr Gln Thr Glu Val Lys Pro Ser
            35                  40                  45

Val Arg Phe Asn Leu Arg Thr Ser Lys Asp Pro Glu His Glu Gly Cys
    50                  55                  60

Tyr Leu Ser Val Gly His Ser Gln Pro Leu Glu Asp Cys Ser Phe Asn
65                  70                  75                  80

Met Thr Ala Lys Thr Phe Phe Ile Ile His Gly Trp Thr Met Ser Gly
                85                  90                  95

Ile Phe Glu Asn Trp Leu His Lys Leu Val Ser Ala Leu His Thr Arg
                100                 105                 110

Glu Lys Asp Ala Asn Val Val Val Asp Trp Leu Pro Leu Ala His
                115                 120                 125

Gln Leu Tyr Thr Asp Ala Val Asn Asn Thr Arg Val Val Gly His Ser
    130                 135                 140

Ile Ala Arg Met Leu Asp Trp Leu Gln Glu Lys Asp Asp Phe Ser Leu
145                 150                 155                 160

Gly Asn Val His Leu Ile Gly Tyr Ser Leu Gly Ala His Val Ala Gly
                165                 170                 175

Tyr Ala Gly Asn Phe Val Lys Gly Thr Val Gly Arg Ile Thr Gly Leu
                180                 185                 190

Asp Pro Ala Gly Pro Met Phe Glu Gly Ala Asp Ile His Lys Arg Leu
                195                 200                 205

Ser Pro Asp Asp Ala Asp Phe Val Asp Val Leu His Thr Tyr Thr Arg
    210                 215                 220

Ser Phe Gly Leu Ser Ile Gly Ile Gln Met Pro Val Gly His Ile Asp
225                 230                 235                 240

Ile Tyr Pro Asn Gly Gly Asp Phe Gln Pro Gly Cys Gly Leu Asn Asp
                245                 250                 255

Val Leu Gly Ser Ile Ala Tyr Gly Thr Ile Thr Glu Val Val Lys Cys
                260                 265                 270

Glu His Glu Arg Ala Val His Leu Phe Val Asp Ser Leu Val Asn Gln
                275                 280                 285

Asp Lys Pro Ser Phe Ala Phe Gln Cys Thr Asp Ser Asn Arg Phe Lys
    290                 295                 300

Lys Gly Ile Cys Leu Ser Cys Arg Lys Asn Arg Cys Asn Asn Ile Gly
305                 310                 315                 320

Tyr Asn Ala Lys Lys Met Arg Lys Lys Arg Asn Ser Lys Met Tyr Leu
                325                 330                 335

Lys Thr Arg Ala Gly Met Pro Phe Lys Val Tyr His Tyr Gln Leu Lys
                340                 345                 350

Val His Met Phe Ser Tyr Asn Asn Ser Gly Asp Thr Gln Pro Thr Leu
    355                 360                 365

Tyr Ile Thr Leu Tyr Gly Ser Asn Ala Asp Ser Gln Asn Leu Pro Leu
    370                 375                 380

Glu Ile Val Glu Lys Ile Glu Leu Asn Ala Thr Asn Thr Phe Leu Val
385                 390                 395                 400

Tyr Thr Glu Glu Asp Leu Gly Asp Leu Leu Lys Met Arg Leu Thr Trp
                405                 410                 415
```

```
Glu Gly Val Ala His Ser Trp Tyr Asn Leu Trp Asn Glu Phe Arg Asn
            420                 425                 430

Tyr Leu Ser Gln Pro Ser Asn Pro Ser Arg Glu Leu Tyr Ile Arg Arg
            435                 440                 445

Ile Arg Val Lys Ser Gly Glu Thr Gln Arg Lys Val Thr Phe Cys Thr
450                 455                 460

Gln Asp Pro Thr Lys Ser Ser Ile Ser Pro Gly Gln Glu Leu Trp Phe
465                 470                 475                 480

His Lys Cys Gln Asp Gly Trp Lys Met Lys Asn Lys Thr Ser Pro Phe
                485                 490                 495

Val Asn Leu Ala Gly Glu Pro Gly Asp Asp Gly Pro Ser Gly Ala Glu
            500                 505                 510

Gly Pro Pro Gly Pro Gln Gly
            515

<210> SEQ ID NO 98
<211> LENGTH: 519
<212> TYPE: PRT
<213> ORGANISM: Artificial Sequence
<220> FEATURE:
<223> OTHER INFORMATION: Synthetic: chimera
<220> FEATURE:
<221> NAME/KEY: PROTEIN
<222> LOCATION: (1)..(519)

<400> SEQUENCE: 98

Met Arg Asn Thr Val Phe Leu Leu Gly Phe Trp Ser Val Tyr Cys Tyr
1               5                   10                  15

Phe Pro Ala Gly Ser Ile Thr Thr Leu Arg Pro Glu Gly Ser Leu Arg
            20                  25                  30

Asp Glu His His Lys Pro Thr Gly Val Pro Ala Thr Ala Arg Pro Ser
        35                  40                  45

Val Ala Phe Asn Ile Arg Thr Ser Lys Asp Pro Glu Gln Glu Gly Cys
50                  55                  60

Asn Leu Ser Leu Gly Asp Ser Lys Leu Leu Glu Asn Cys Gly Phe Asn
65                  70                  75                  80

Met Thr Ala Lys Thr Phe Ile Ile His Gly Trp Thr Met Ser Gly
                85                  90                  95

Met Phe Glu Ser Trp Leu His Lys Leu Val Ser Ala Leu Gln Met Arg
            100                 105                 110

Glu Lys Asp Ala Asn Val Val Val Asp Trp Leu Pro Leu Ala His
            115                 120                 125

Gln Leu Tyr Thr Asp Ala Val Asn Asn Thr Arg Val Val Gly Gln Arg
        130                 135                 140

Val Ala Gly Met Leu Asp Trp Leu Gln Glu Lys Glu Glu Phe Ser Leu
145                 150                 155                 160

Gly Asn Val His Leu Ile Gly Tyr Ser Leu Gly Ala His Val Ala Gly
                165                 170                 175

Tyr Ala Gly Asn Phe Val Lys Gly Thr Val Gly Arg Ile Thr Gly Leu
            180                 185                 190

Asp Pro Ala Gly Pro Met Phe Glu Gly Ala Asp Ile His Lys Arg Leu
        195                 200                 205

Ser Pro Asp Asp Ala Asp Phe Val Asp Val Leu His Thr Tyr Thr Arg
    210                 215                 220

Ser Phe Gly Leu Ser Ile Gly Ile Gln Met Pro Val Gly His Ile Asp
225                 230                 235                 240
```

-continued

Ile Tyr Pro Asn Gly Gly Asp Phe Gln Pro Gly Cys Gly Leu Asn Asp
                245                 250                 255

Val Leu Gly Ser Ile Ala Tyr Gly Thr Ile Thr Glu Val Val Lys Cys
            260                 265                 270

Glu His Glu Arg Ala Val His Leu Phe Val Asp Ser Leu Val Asn Gln
        275                 280                 285

Asp Lys Pro Ser Phe Ala Phe Gln Cys Thr Asp Ser Asn Arg Phe Lys
    290                 295                 300

Lys Gly Ile Cys Leu Ser Cys Arg Lys Asn Arg Cys Asn Ser Ile Gly
305                 310                 315                 320

Tyr Asn Ala Lys Lys Met Arg Asn Lys Asn Ser Lys Met Tyr Leu
                325                 330                 335

Lys Thr Arg Ala Gly Met Pro Phe Arg Val Tyr His Tyr Gln Met Lys
            340                 345                 350

Ile His Val Phe Ser Tyr Lys Asn Met Gly Glu Ile Glu Pro Thr Phe
        355                 360                 365

Tyr Val Thr Leu Tyr Gly Thr Asn Ala Asp Ser Gln Thr Leu Pro Leu
    370                 375                 380

Glu Ile Val Glu Arg Ile Glu Gln Asn Ala Thr Asn Thr Phe Leu Val
385                 390                 395                 400

Tyr Thr Glu Glu Asp Leu Gly Asp Leu Leu Lys Ile Gln Leu Thr Trp
                405                 410                 415

Glu Gly Ala Ser Gln Ser Trp Tyr Asn Leu Trp Lys Glu Phe Arg Ser
            420                 425                 430

Tyr Leu Ser Gln Pro Arg Asn Pro Gly Arg Glu Leu Asn Ile Arg Arg
        435                 440                 445

Ile Arg Val Lys Ser Gly Glu Thr Gln Arg Lys Leu Thr Phe Cys Thr
    450                 455                 460

Glu Asp Pro Glu Asn Thr Ser Ile Ser Pro Gly Gln Glu Leu Trp Phe
465                 470                 475                 480

Arg Lys Cys Arg Asp Gly Trp Arg Met Lys Asn Glu Thr Ser Pro Thr
                485                 490                 495

Val Glu Leu Pro Gly Pro Gly Asp Asp Gly Pro Ser Gly Ala Glu
            500                 505                 510

Gly Pro Pro Gly Pro Gln Gly
        515

<210> SEQ ID NO 99
<211> LENGTH: 116
<212> TYPE: PRT
<213> ORGANISM: Mus musculus
<220> FEATURE:
<221> NAME/KEY: PROTEIN
<222> LOCATION: (1)..(116)

<400> SEQUENCE: 99

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Thr Tyr
            20                  25                  30

Trp Ile Ala Trp Val Lys Gln Arg Pro Gly His Gly Leu Glu Trp Ile
        35                  40                  45

Gly Glu Ile Leu Pro Gly Ser Ala Lys Thr Lys Tyr Asn Lys Lys Phe
    50                  55                  60

Lys Gly Lys Ala Thr Phe Thr Ala Asp Thr Ser Ser Asn Thr Ala Tyr

```
                65                  70                  75                  80
Met Gln Leu Ser Ser Leu Thr Ser Glu Asp Ser Ala Val Tyr Tyr Cys
                        85                  90                  95

Ala Val Tyr Asp Tyr Gly Ala Asp Tyr Trp Gly Gln Gly Thr Ser Val
                100                 105                 110

Thr Val Ser Ser
        115

<210> SEQ ID NO 100
<211> LENGTH: 5
<212> TYPE: PRT
<213> ORGANISM: Mus musculus
<220> FEATURE:
<221> NAME/KEY: PROTEIN
<222> LOCATION: (1)..(5)

<400> SEQUENCE: 100

Thr Tyr Trp Ile Ala
1               5

<210> SEQ ID NO 101
<211> LENGTH: 17
<212> TYPE: PRT
<213> ORGANISM: Mus musculus
<220> FEATURE:
<221> NAME/KEY: PROTEIN
<222> LOCATION: (1)..(17)

<400> SEQUENCE: 101

Glu Ile Leu Pro Gly Ser Ala Lys Thr Lys Tyr Asn Lys Lys Phe Lys
1               5                   10                  15

Gly

<210> SEQ ID NO 102
<211> LENGTH: 7
<212> TYPE: PRT
<213> ORGANISM: Mus musculus
<220> FEATURE:
<221> NAME/KEY: PROTEIN
<222> LOCATION: (1)..(7)

<400> SEQUENCE: 102

Tyr Asp Tyr Gly Ala Asp Tyr
1               5

<210> SEQ ID NO 103
<211> LENGTH: 107
<212> TYPE: PRT
<213> ORGANISM: Mus musculus
<220> FEATURE:
<221> NAME/KEY: PROTEIN
<222> LOCATION: (1)..(107)

<400> SEQUENCE: 103

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Tyr Thr Ala
                20                  25                  30

Val Ala Trp Tyr Gln Gln Lys Pro Gly Gln Ser Pro Lys Leu Leu Ile
                35                  40                  45

Tyr Ser Ala Ser Tyr Arg Phe Thr Gly Val Pro Asp Arg Phe Thr Gly
        50                  55                  60

Ser Gly Ala Gly Thr Glu Phe Thr Phe Thr Ile Asn Ser Val Gln Ala
```

```
                65                  70                  75                  80
Glu Asp Leu Ala Val Tyr Tyr Cys Gln Gln His Tyr Ser Ile Pro Arg
                    85                  90                  95
Thr Phe Gly Gly Gly Thr Lys Leu Glu Ile Lys
            100                 105
```

<210> SEQ ID NO 104
<211> LENGTH: 11
<212> TYPE: PRT
<213> ORGANISM: Mus musculus
<220> FEATURE:
<221> NAME/KEY: PROTEIN
<222> LOCATION: (1)..(11)

<400> SEQUENCE: 104

```
Lys Ala Ser Gln Asp Val Tyr Thr Ala Val Ala
1               5                   10
```

<210> SEQ ID NO 105
<211> LENGTH: 7
<212> TYPE: PRT
<213> ORGANISM: Mus musculus
<220> FEATURE:
<221> NAME/KEY: PROTEIN
<222> LOCATION: (1)..(7)

<400> SEQUENCE: 105

```
Ser Ala Ser Tyr Arg Phe Thr
1               5
```

<210> SEQ ID NO 106
<211> LENGTH: 9
<212> TYPE: PRT
<213> ORGANISM: Mus musculus
<220> FEATURE:
<221> NAME/KEY: PROTEIN
<222> LOCATION: (1)..(9)

<400> SEQUENCE: 106

```
Gln Gln His Tyr Ser Ile Pro Arg Thr
1               5
```

<210> SEQ ID NO 107
<211> LENGTH: 17
<212> TYPE: PRT
<213> ORGANISM: Mus musculus
<220> FEATURE:
<221> NAME/KEY: misc_feature
<222> LOCATION: (12)..(12)
<223> OTHER INFORMATION: Xaa can be Ala or Thr
<220> FEATURE:
<221> NAME/KEY: misc_feature
<222> LOCATION: (13)..(13)
<223> OTHER INFORMATION: Xaa can be Gly or Asp

<400> SEQUENCE: 107

```
Trp Ile Asn Thr Tyr Ser Gly Val Pro Thr Tyr Xaa Xaa Asp Phe Lys
1               5                   10                  15
Gly
```

<210> SEQ ID NO 108
<211> LENGTH: 11
<212> TYPE: PRT
<213> ORGANISM: Mus musculus
<220> FEATURE:
<221> NAME/KEY: misc_feature
<222> LOCATION: (1)..(1)

```
<223> OTHER INFORMATION: Xaa can be Arg or Phe
<220> FEATURE:
<221> NAME/KEY: misc_feature
<222> LOCATION: (2)..(2)
<223> OTHER INFORMATION: Xaa can be Gly or Ser
<220> FEATURE:
<221> NAME/KEY: misc_feature
<222> LOCATION: (7)..(7)
<223> OTHER INFORMATION: Xaa can be Arg or His
<220> FEATURE:
<221> NAME/KEY: misc_feature
<222> LOCATION: (11)..(11)
<223> OTHER INFORMATION: Xaa can be Val or Tyr

<400> SEQUENCE: 108

Xaa Xaa Tyr Tyr Gly Arg Xaa Tyr Phe Asp Xaa
1               5                   10

<210> SEQ ID NO 109
<211> LENGTH: 15
<212> TYPE: PRT
<213> ORGANISM: Mus musculus
<220> FEATURE:
<221> NAME/KEY: misc_feature
<222> LOCATION: (10)..(10)
<223> OTHER INFORMATION: Xaa can be Val or Gly
<220> FEATURE:
<221> NAME/KEY: misc_feature
<222> LOCATION: (15)..(15)
<223> OTHER INFORMATION: Xaa can be His or Asn

<400> SEQUENCE: 109

Lys Ala Ser Gln Ser Val Asp Tyr Asp Xaa Asp Ser Tyr Met Xaa
1               5                   10                  15

<210> SEQ ID NO 110
<211> LENGTH: 7
<212> TYPE: PRT
<213> ORGANISM: Mus musculus
<220> FEATURE:
<221> NAME/KEY: misc_feature
<222> LOCATION: (6)..(6)
<223> OTHER INFORMATION: Xaa can be any naturally occurring amino acid

<400> SEQUENCE: 110

Ala Ala Ser Asn Leu Xaa Ser
1               5

<210> SEQ ID NO 111
<211> LENGTH: 10
<212> TYPE: PRT
<213> ORGANISM: Mus musculus
<220> FEATURE:
<221> NAME/KEY: misc_feature
<222> LOCATION: (1)..(1)
<223> OTHER INFORMATION: Xaa can be His or Gln
<220> FEATURE:
<221> NAME/KEY: misc_feature
<222> LOCATION: (3)..(3)
<223> OTHER INFORMATION: Xaa can be Thr or Ser
<220> FEATURE:
<221> NAME/KEY: misc_feature
<222> LOCATION: (4)..(4)
<223> OTHER INFORMATION: Xaa can be Ile or Thr or Asn
<220> FEATURE:
<221> NAME/KEY: misc_feature
<222> LOCATION: (5)..(5)
<223> OTHER INFORMATION: Xaa can be Glu or Asp
<220> FEATURE:
<221> NAME/KEY: misc_feature
<222> LOCATION: (9)..(9)
<223> OTHER INFORMATION: Xaa, if present, is Trp
```

<400> SEQUENCE: 111

Xaa Gln Xaa Xaa Xaa Asp Pro Pro Xaa Thr
1               5                   10

<210> SEQ ID NO 112
<211> LENGTH: 5
<212> TYPE: PRT
<213> ORGANISM: Mus musculus
<220> FEATURE:
<221> NAME/KEY: misc_feature
<222> LOCATION: (1)..(1)
<223> OTHER INFORMATION: Xaa can be Asp or Glu
<220> FEATURE:
<221> NAME/KEY: misc_feature
<222> LOCATION: (2)..(2)
<223> OTHER INFORMATION: Xaa can be Tyr or Asn
<220> FEATURE:
<221> NAME/KEY: misc_feature
<222> LOCATION: (4)..(4)
<223> OTHER INFORMATION: Xaa can be Met or Ile

<400> SEQUENCE: 112

Xaa Xaa Thr Xaa His
1               5

<210> SEQ ID NO 113
<211> LENGTH: 17
<212> TYPE: PRT
<213> ORGANISM: Mus musculus
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be Tyr or Asn

<400> SEQUENCE: 113

Xaa Ile Asn Pro Tyr Tyr Gly Gly Thr Xaa Xaa Asn Glu Lys Phe Lys
1               5                   10                  15

Asp

<210> SEQ ID NO 114
<211> LENGTH: 5
<212> TYPE: PRT
<213> ORGANISM: Mus musculus
<220> FEATURE:
<221> NAME/KEY: misc_feature
<222> LOCATION: (1)..(1)
<223> OTHER INFORMATION: Xaa can be Gly or Ser

<400> SEQUENCE: 114

Xaa Tyr Thr Met Ser
1               5

<210> SEQ ID NO 115
<211> LENGTH: 17
<212> TYPE: PRT
<213> ORGANISM: Mus musculus
<220> FEATURE:
<221> NAME/KEY: misc_feature
<222> LOCATION: (5)..(5)
<223> OTHER INFORMATION: Xaa can be Ala or Thr
<220> FEATURE:
<221> NAME/KEY: misc_feature

```
<222> LOCATION: (7)..(7)
<223> OTHER INFORMATION: Xaa can be Asp or Ser

<400> SEQUENCE: 115

Glu Ile Ser Phe Xaa Arg Xaa Arg Ala Phe Tyr Pro Asp Thr Val Lys
1               5                   10                  15

Gly

<210> SEQ ID NO 116
<211> LENGTH: 13
<212> TYPE: PRT
<213> ORGANISM: Mus musculus
<220> FEATURE:
<221> NAME/KEY: misc_feature
<222> LOCATION: (4)..(4)
<223> OTHER INFORMATION: Xaa can be Arg or Asn
<220> FEATURE:
<221> NAME/KEY: misc_feature
<222> LOCATION: (6)..(6)
<223> OTHER INFORMATION: Xaa can be His or Tyr

<400> SEQUENCE: 116

Leu Gly Gly Xaa Asn Xaa Asp Tyr Trp Tyr Phe Asp Val
1               5                   10
```